(12) United States Patent
Sakami et al.

(10) Patent No.: US 6,770,654 B2
(45) Date of Patent: Aug. 3, 2004

(54) INDOLE DERIVATIVES AND USE THEREOF IN MEDICINES

(75) Inventors: Satoshi Sakami, Kanagawa (JP); Koji Kawai, Kanagawa (JP); Masayuki Maeda, Kanagawa (JP); Takumi Aoki, Kanagawa (JP); Shinya Ueno, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 10/432,011

(22) PCT Filed: Nov. 22, 2001

(86) PCT No.: PCT/JP01/10249

§ 371 (c)(1),
(2), (4) Date: May 19, 2003

(87) PCT Pub. No.: WO02/42309

PCT Pub. Date: May 30, 2002

(65) Prior Publication Data

US 2004/0019071 A1 Jan. 29, 2004

(30) Foreign Application Priority Data

Nov. 22, 2000 (JP) ......................................... 2000-356382

(51) Int. Cl.$^7$ ..................... A61K 31/475; C07D 471/18
(52) U.S. Cl. ........................... 514/279; 546/35; 546/31; 546/28
(58) Field of Search ........................... 514/279; 546/35, 546/31, 28

(56) References Cited

U.S. PATENT DOCUMENTS 5,849,731 A * 12/1998 Nagase et al. .............. 514/183

FOREIGN PATENT DOCUMENTS

WO    WO 97/11948 A1    4/1997

* cited by examiner

Primary Examiner—Charanjit S. Aulakh
(74) Attorney, Agent, or Firm—Birch, Stewart, Kolasch & Birch, LLP

(57) ABSTRACT

This invention relates to: an indole derivative or a pharmaceutically acceptable salt thereof represented by formula (I):

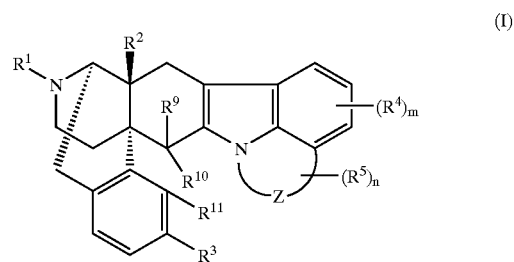

wherein $R^1$ is, for example, hydrogen or $C_{1-5}$ alkyl; $R^2$ is, for example, hydrogen or hydroxy; $R^3$ is, for example, hydrogen or hydroxy; —Z— is a crosslinkage having 2 to 5 carbon atoms; m is an integer from 0 to 3; n is an integer from 0 to 10; $R^4$ and $R^5$ are, for example, fluoro or hydroxy; $R^9$ is, for example, hydrogen or $C_{1-5}$ alkyl; and $R^{10}$ and $R^{11}$ are bound to each other to form, for example, —O—; and a pharmaceutical composition comprising the same, particularly a drug acting on δ opioid receptor.

14 Claims, No Drawings

INDOLE DERIVATIVES AND USE THEREOF IN MEDICINES

This application is the national phase under 35 U.S.C. §371 of PCT International Application No. PCT/JP01/10249 which has an International filing date of Nov. 22, 2001, which designated the United States of America.

TECHNICAL FIELD

The present invention relates to a novel indole derivative and medical applications thereof.

BACKGROUND ART

Nowadays, opioid receptors are classified into three types: $\mu$, $\delta$, and $\kappa$. Among these, research on the $\delta$ opioid receptor was behind that regarding receptors of other types. Recently, however, several ligands selective to the $\delta$ opioid receptor have been developed, and pharmacological actions relating to the $\delta$ opioid receptor have become elucidated. Examples of known pharmacological actions relating to the $\delta$ opioid receptor include analgesic, antitussive, immunosuppressive, and brain-cell-protecting actions.

Although $\mu$ opioid agonists, represented by morphine, have been used as analgesics, $\mu$ agonists have serious $\mu$ opioidergic side effects such as drug dependence, suppression of the CNS, respiratory depression, or constipation. Also, since codeine, which is known as a typical antitussive, is related to the $\mu$ opioid receptor, the aforementioned side effects are of serious concern. Antitussive actions of $\kappa$ opioid agonists are also known, although the $\kappa$ opioid agonists have side effects such as drug aversion or psychotomimetic effects. Although analgesic actions of the $\delta$ opioid agonists have been reported, they are highly unlikely to show serious side effects compared to those of $\mu$ and $\kappa$ opioid agonists.

As mentioned above, there are several known pharmacological actions relating to the $\delta$ opioid receptor. With the use of the $\delta$ receptor ligands as therapeutic agents for various diseases, separation from side effects such as drug dependence or psychotomimetic effects relating to $\mu$ and $\kappa$ opioid receptors can be expected. Under these circumstances, the development of ligands selective to $\delta$ opioid receptors has been proceeding, and agents that act on the $\delta$ opioid receptor with higher affinity and higher selectivity are desired.

Known $\delta$ ligand compounds are those described in WO 97/11948, etc. For example, WO 97/11948 describes a compound represented by general formula (I) according to the present invention, wherein $R^1$ represents cyclopropylmethyl, $R^2$ represents a hydroxy group, $R^3$ represents a methoxy group, $R^{10}$ and $R^{11}$ are bound to each other to form —O—, —Z— represents — $CH_2CH_2CH_2$—, and m and n are each 0. In the present invention, the introduction of hydroxy and/or oxo as $R^4$ and/or $R^5$ can lower metabolic rate. This enables excellent drug efficacy to be sustained for a long period of time, and thus, frequency of administration can be reduced.

DISCLOSURE OF THE INVENTION

An object of the present invention is to provide a $\delta$ opioid receptor-selective ligand that can be used as an analgesic, antitussive, immunosuppressive, or brain-cell-protecting agent without serious side effects such as drug dependence, suppression of the CNS, or drug aversion relating to the $\mu$ and $\kappa$ opioid receptors.

The present inventors have conducted concentrated studies in order to attain the above object. As a result, we have found an indole derivative that acts with high selectivity on the $\delta$ opioid receptor, thereby completing the present invention. More specifically, the present invention provides an indole derivative represented by general formula (I) or a pharmaceutically acceptable salt thereof, and a pharmaceutical comprising the same:

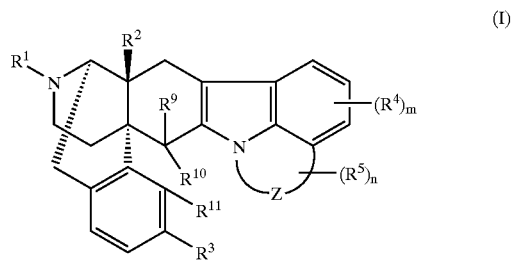

(I)

wherein $R^1$ is hydrogen, $C_{1-5}$ alkyl, $C_{4-7}$ cycloalkylalkyl, $C_{5-7}$ cycloalkenylalkyl, $C_{6-12}$ aryl, $C_{7-13}$ aralkyl, $C_{3-7}$ alkenyl, furan-2-yl-alkyl (wherein the alkyl moiety is $C_{1-5}$), or thiophen-2-yl-alkyl (wherein the alkyl moiety is $C_{1-5}$);

$R^2$ is hydrogen, hydroxy, $C_{1-5}$ alkoxy, or $C_{1-5}$ aliphatic acyloxy;

$R^3$ is hydrogen, hydroxy, $C_{2-5}$ alkoxy, $C_{1-5}$ aliphatic acyloxy, or $C_{7-13}$ aralkyloxy;

—Z— is a crosslinkage having 2 to 5 carbon atoms;

m is an integer from 0 to 3;

n is an integer from 0 to 10;

m number of $R^4$ groups and n number of $R^5$ groups are independently fluoro, chloro, bromo, iodo, nitro, $C_{1-5}$ alkyl, hydroxy, $C_{1-5}$ alkoxy, trifluoromethyl, trifluoromethoxy, cyano, phenyl, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH_2)_pN(R^7)COR^8$, (wherein p is an integer from 0 to 5; $R^6$ is hydrogen or $C_{1-5}$ alkyl; and $R^7$ and $R^8$ are independently hydrogen, $C_{1-5}$ alkyl, or $C_{4-7}$ cycloalkylalkyl), among the above n number of $R^5$ groups, two $R^5$ groups bound to the same carbon atom become an oxygen atom to form oxo, or among the above m number of $R^4$ groups and n number of $R^5$ groups, two adjacent $R^4$ groups, two adjacent $R^5$ groups, or one $R^4$ and one $R^5$ groups may be bound to each other to form a benzene, pyridine, cyclopentane, cyclohexane, or cycloheptane fused ring (wherein at least one of m number of $R^4$ groups and n number of $R^5$ groups should be hydroxy, or two $R^5$ groups bound to the same carbon atom should become an oxygen atom to form oxo);

$R^9$ is hydrogen, $C_{1-5}$ alkyl, $C_{2-5}$ alkenyl, $C_{7-13}$ aralkyl, $C_{1-3}$ hydroxyalkyl, $(CH_2)_pOR^6$, or $(CH_2)_pCO_2R^6$, wherein p and $R^6$ are as defined above; and $R^{10}$ and $R^{11}$ are bound to each other to form —O—, —S—, or —$CH_2$—, or $R^{10}$ is hydrogen while $R^{11}$ is independently hydrogen, hydroxy, $C_{1-5}$ alkoxy, or $C_{1-5}$ aliphatic acyloxy.

The present invention also provides a drug acting on $\delta$ opioid receptor that comprises, as an active ingredient, an indole derivative represented by general formula (I) or a pharmaceutically acceptable salt thereof. The "drug acting on $\delta$ opioid receptor" used herein refers to a $\delta$ opioid agonist or $\delta$ opioid antagonist.

Examples of $C_{1-5}$ alkyl used herein include methyl, ethyl, propyl, isopropyl, butyl, isobutyl, sec-butyl, t-butyl, and pentyl. Examples of $C_{4-7}$ cycloalkylalkyl include cyclopropylmethyl, 2-cyclopropylethyl, 3-cyclopropylpropyl, 4-cyclopropylbutyl, cyclobutylmethyl, and cyclohexylmethyl. Examples of $C_{5-7}$ cycloalkenylalkyl include cyclobutenylmethyl, 2-cyclobutenylethyl, and 3-cyclobutenylpropyl. Examples of $C_{6-12}$ aryl include phenyl, naphthyl, and tolyl. Examples of $C_{7-13}$ aralkyl include benzyl, phenethyl, naphthylmethyl, and 3-phenylpropyl. Examples of $C_{3-7}$ alkenyl include allyl, 3-butynyl, and phenyl. Examples of furan-2-yl-alkyl (wherein the alkyl moiety is $C_{1-5}$) include 2-furylmethyl, 2-(2-furyl)ethyl, 1-(2-furyl)ethyl, and 3-(2-furyl)propyl. Examples of thiophen-2-yl-alkyl (wherein the alkyl moiety is $C_{1-5}$) include 2-thienylmethyl, 2-(2-thienyl)ethyl, 1-(2-thienyl)ethyl, and 3-(2-thienyl)propyl. Examples of $C_{1-5}$ alkoxy include methoxy, ethoxy, propoxy, isopropoxy, butoxy, isobutoxy, sec-butoxy, t-butoxy, and pentyloxy. Examples of $C_{2-5}$ alkoxy are the examples of $C_{1-5}$ alkoxy except for methoxy. Examples of $C_{1-5}$ aliphatic acyloxy include formyloxy, acetoxy, propionoxy, and pentanoyloxy. Examples of $C_{7-13}$ aralkyloxy include benzyloxy, phenethyloxy, and naphthylmethoxy.

According to a preferred embodiment of the compound represented by general formula (I), $R^1$ is $C_{4-7}$ cycloalkylalkyl and $C_{3-7}$ alkenyl, and $C_{4-7}$ cycloalkylalkyl is more preferable. As another embodiment, $R^1$ is hydrogen, $C_{1-5}$ alkyl, $C_{7-13}$ aralkyl, furan-2-yl-alkyl (wherein the alkyl moiety is $C_{1-5}$), or thiophen-2-yl-alkyl (wherein the alkyl moiety is $C_{1-5}$).

Among these preferred examples, hydrogen, $C_{1-5}$ alkyl, $C_{4-7}$ cycloalkylmethyl, $C_{3-7}$ alkenyl, $C_{7-13}$ aralkyl, furan-2-yl-alkyl (wherein the alkyl moiety is $C_{1-5}$), or thiophen-2-yl-alkyl (wherein the alkyl moiety is $C_{1-5}$) is more preferable. Hydrogen, methyl, phenethyl, 2-(2-furyl)ethyl (furan-2-yl-ethyl), or 2-(2-thienyl)ethyl (thiophen-2-yl-ethyl) is particularly preferred, and cyclopropylmethyl is also particularly preferable.

$R^2$ is preferably hydrogen, hydroxy, acetoxy, propionoxy, methoxy, or ethoxy, and hydrogen, hydroxy, acetoxy, or methoxy is particularly preferred.

$R^3$ is preferably hydrogen, hydroxy, or acetoxy, and hydroxy is particularly preferred.

—Z— is preferably $C_{2-5}$ alkylene.

$R^4$ and $R^5$ are preferably fluoro, chloro, bromo, iodo, nitro, $C_{1-5}$ alkyl, hydroxy, $C_{1-5}$ alkoxy, trifluoromethyl, trifluoromethoxy, cyano, phenyl, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH_2)_pN(R^7)COR^8$ (wherein p is an integer from 0 to 5; $R^6$ is hydrogen or $C_{1-5}$ alkyl; and $R^7$ and $R^8$ are independently hydrogen, $C_{1-5}$ alkyl, or $C_{4-7}$ cycloalkylalkyl). Particularly preferred is fluoro, chloro, bromo, iodo, nitro, methyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, carboxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl, or amino. It is also preferable if two $R^5$ groups bound to the same carbon atom become an oxygen atom to form oxo. Two adjacent $R^4$ groups, two adjacent $R^5$ groups, or one $R^4$ and one $R^5$ groups may be preferably bound to each other to form at least one benzene, pyridine, cyclopentane, cyclohexane, or cycloheptane fused ring. Particularly preferred groups form a benzene fused ring.

$R^9$ is preferably hydrogen, $C_{1-5}$ alkyl, allyl, or benzyl, and hydrogen or methyl is particularly preferred.

$R^{10}$ and $R^{11}$ are preferably bound to each other to form —O—, or $R^{10}$ is preferably hydrogen while $R^{11}$ is hydrogen, hydroxy, or methoxy, and groups bound to each other to form —O— are particularly preferred.

The present invention, however, is not limited to these conditions.

The indole derivative represented by general formula (I) according to the present invention is a compound wherein at least one of m number of $R^4$ groups and n number of $R^5$ groups is hydroxy, or two $R^5$ groups bound to the same carbon atom become one oxygen atom to form oxo. Specific examples of compounds are represented by ①, ②, and ③ below.

① A compound as exemplified in Compound 13 wherein $R^1, R^2, R^3$, —Z—, $R^9, R^{10}$, and $R^{11}$ are as defined in general formula (I); and one $R^4$ group is hydroxy while the remaining 0 to 2 $R^4$ groups and 0 to 10 $R^5$ groups are independently fluoro, chloro, bromo, iodo, nitro, $C_{1-5}$ alkyl, hydroxy, $C_{1-5}$ alkoxy, trifluoromethyl, trifluoromethoxy, cyano, phenyl, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH_2)_pN(R^7)COR^8$ (wherein p is an integer from 0 to 5; $R^6$ is hydrogen or $C_{1-5}$ alkyl; and $R^7$ and $R^8$ are independently hydrogen, $C_{1-5}$ alkyl, or $C_{4-7}$ cycloalkylalkyl), two $R^5$ groups bound to the same carbon atom become an oxygen atom to form oxo, or two adjacent $R^4$ groups, two adjacent $R^5$ groups, or $R^4$ and $R^5$ are bound to each other to form a benzene, pyridine, cyclopentane, cyclohexane, or cycloheptane fused ring.

② A compound as exemplified in Compound 2 wherein $R^1, R^2, R^3$, —Z—, $R^9, R^{10}$, and $R^{11}$ are as defined in general formula (I); and one $R^5$ group is hydroxy while the remaining 0 to 9 $R^5$ groups and 0 to 3 $R^4$ groups are independently fluoro, chloro, bromo, iodo, nitro, $C_{1-5}$ alkyl, hydroxy, $C_{1-5}$ alkoxy, trifluoromethyl, trifluoromethoxy, cyano, phenyl, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH_2)_pN(R^7)COR^8$ (wherein p is an integer from 0 to 5; $R^6$ is hydrogen or $C_{1-5}$ alkyl; and $R^7$ and $R^8$ are independently hydrogen, $C_{1-5}$ alkyl, or $C_{4-7}$ cycloalkylalkyl), two $R^5$ groups bound to the same carbon atom become an oxygen atom to form oxo, or two adjacent $R^4$ groups, two adjacent $R^5$ groups, or $R^4$ and $R^5$ are bound to each other to form a benzene, pyridine, cyclopentane, cyclohexane, or cycloheptane fused ring.

③ A compound as exemplified in Compound 1 wherein $R^1, R^2, R^3$, —Z—, $R^9, R^{10}$, and $R^{11}$ are as defined in general formula (I); and two $R^5$ groups bound to the same carbon atom become an oxygen atom to form oxo while the remaining 0 to 8 $R^5$ groups and 0 to 3 $R^4$ groups are independently fluoro, chloro, bromo, iodo, nitro, $C_{1-5}$ alkyl, hydroxy, $C_{1-5}$ alkoxy, trifluoromethyl, trifluoromethoxy, cyano, phenyl, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH_2)_pN(R^7)COR^8$ (wherein p is an integer from 0 to 5; $R^6$ is hydrogen or $C_{1-5}$ alkyl; and $R^7$ and $R^8$ are independently hydrogen, $C_{1-5}$ alkyl, or $C_{4-7}$ cycloalkylalkyl), two $R^5$ groups bound to the same carbon atom become an oxygen atom to form oxo, or two adjacent $R^4$ groups, two adjacent $R^5$ groups, or $R^4$ and $R^5$ are bound to each other to form a benzene, pyridine, cyclopentane, cyclohexane, or cycloheptane fused ring.

A preferred example of ① above is a compound wherein $R^1$ is hydrogen, $C_{1-5}$ alkyl, $C_{4-7}$ cycloalkylalkyl, $C_{3-7}$ alkenyl, $C_{7-13}$ aralkyl, furan-2-yl-alkyl (wherein the alkyl moiety is $C_{1-5}$), or thiophen-2-yl-alkyl (wherein the alkyl moiety is $C_{1-5}$); $R^2$ is hydrogen, hydroxy, acetoxy, propionoxy, methoxy, or ethoxy; $R^3$ is hydrogen, hydroxy, or acetoxy; —Z— is $C_{2-5}$ alkylene; one $R^4$ group is hydroxy while the remaining 0 to 2 $R^4$ groups and 0 to 10 $R^5$ groups are independently fluoro, chloro, bromo, iodo, nitro, $C_{1-5}$ alkyl, hydroxy, $C_{1-5}$ alkoxy, trifluoromethyl, trifluoromethoxy, cyano, phenyl, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH_2)_pN(R^7)COR^8$ (wherein p is an integer from 0 to 5; $R^6$ is hydrogen or $C_{1-5}$ alkyl; and $R^7$ and $R^8$ are independently hydrogen, $C_{1-5}$ alkyl, or $C_{4-7}$ cycloalkylalkyl), two $R^5$ groups bound to the same carbon atom become an oxygen atom to form oxo, or two adjacent $R^4$ groups, two adjacent $R^5$ groups, or $R^4$ and $R^5$ are bound to each other to form at least one benzene, pyridine, cyclopentane, cyclohexane, or cycloheptane fused ring; $R^9$ is hydrogen, $C_{1-5}$ alkyl, allyl, or benzyl; and $R^{10}$ and $R^{11}$ are bound to each other to form —O— or $R^{10}$ is hydrogen while $R^{11}$ is hydrogen, hydroxy, or methoxy. An example of a particularly preferable compound is one wherein $R^1$ is hydrogen, methyl, cyclopropylmethyl, phenethyl, furan-2-yl-ethyl, or thiophen-2-yl-ethyl; $R^2$ is hydrogen, hydroxy, acetoxy, or methoxy; $R^3$ is hydroxy; —Z— is $C_{2-5}$ alkylene; one $R^4$ is hydroxy while the remaining 0 to 2 $R^4$ groups and 0 to 10 $R^5$ groups are independently fluoro, chloro, bromo, iodo, nitro, methyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, carboxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl, or amino, two $R^5$ groups bound to the same carbon atom become an oxygen atom to form oxo, or two adjacent $R^4$ groups, two adjacent $R^5$ groups, or $R^4$ and $R^5$ are bound to each other to form a benzene fused ring; $R^9$ is hydrogen or methyl; and $R^{10}$ and $R^{11}$ are bound to each other to form —O—.

A preferred example of ② above is a compound wherein $R^1$ is hydrogen, $C_{1-5}$ alkyl, $C_{4-7}$ cycloalkylalkyl, $C_{3-7}$ alkenyl, $C_{7-13}$ aralkyl, furan-2-yl-alkyl (wherein the alkyl moiety is $C_{1-5}$), or thiophen-2-yl-alkyl (wherein the alkyl moiety is $C_{1-5}$); $R^2$ is hydrogen, hydroxy, acetoxy, propionoxy, methoxy, or ethoxy; $R^3$ is hydrogen, hydroxy, or acetoxy; —Z— is $C_{2-5}$ alkylene; one $R^5$ group is hydroxy while the remaining 0 to 9 $R^5$ groups and 0 to 3 $R^4$ groups are independently fluoro, chloro, bromo, iodo, nitro, $C_{1-5}$ alkyl, hydroxy, $C_{1-5}$ alkoxy, trifluoromethyl, trifluoromethoxy, cyano, phenyl, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH_2)_pN(R^7)COR^8$ (wherein p is an integer from 0 to 5; $R^6$ is hydrogen or $C_{1-5}$ alkyl; and $R^7$ and $R^8$ are independently hydrogen, $C_{1-5}$ alkyl, or $C_{4-7}$ cycloalkylalkyl), two $R^5$ groups bound to the same carbon atom become an oxygen atom to form oxo, or two adjacent $R^4$ groups, two adjacent $R^5$ groups, or $R^4$ and $R^5$ are bound to each other to form at least one benzene, pyridine, cyclopentane, cyclohexane, or cycloheptane fused ring; $R^9$ is hydrogen, $C_{1-5}$ alkyl, allyl, or benzyl; and $R^{10}$ and $R^{11}$ are bound to each other to form —O— or $R^{10}$ is hydrogen while $R^{11}$ is hydrogen, hydroxy, or methoxy. An example of a particularly preferable compound is one wherein $R^1$ is hydrogen, methyl, cyclopropylmethyl, phenethyl, furan-2-ylethyl, or thiophen-2-ylethyl; $R^2$ is hydrogen, hydroxy, acetoxy, or methoxy; $R^3$ is hydroxy; —Z— is $C_{2-5}$ alkylene; one $R^5$ is hydroxy while the remaining 0 to 9 $R^5$ groups and 0 to 3 $R^4$ groups are independently fluoro, chloro, bromo, iodo, nitro, methyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, carboxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl, or amino, two $R^5$ groups bound to the same carbon atom become an oxygen atom to form oxo, or two adjacent $R^4$ groups, two adjacent $R^5$ groups, or $R^4$ and $R^5$ are bound to each other to form a benzene fused ring; $R^9$ is hydrogen or methyl; and $R^{10}$ and $R^{11}$ are bound to each other to form —O—.

A preferred example of ③ above is a compound wherein $R^1$ is hydrogen, $C_{1-5}$ alkyl, $C_{4-7}$ cycloalkylalkyl, $C_{3-7}$ alkenyl, $C_{7-13}$ aralkyl, furan-2-yl-alkyl (wherein the alkyl moiety is $C_{1-5}$), or thiophen-2-yl-alkyl (wherein the alkyl moiety is $C_{1-5}$); $R^2$ is hydrogen, hydroxy, acetoxy, propionoxy, methoxy, or ethoxy; $R^3$ is hydrogen, hydroxy, or acetoxy; —Z— is $C_{2-5}$ alkylene; two $R^5$ groups bound to the same carbon atom become an oxygen atom to form oxo while the remaining 0 to 8 $R^5$ groups and 0 to 3 $R^4$ groups are independently fluoro, chloro, bromo, iodo, nitro, $C_{1-5}$ alkyl, hydroxy, $C_{1-5}$ alkoxy, trifluoromethyl, trifluoromethoxy, cyano, phenyl, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH_2)_pN(R^7)COR^8$ (wherein p is an integer from 0 to 5; $R^6$ is hydrogen or $C_{1-5}$ alkyl; and $R^7$ and $R^8$ are independently hydrogen, $C_{1-5}$ alkyl, or $C_{4-7}$ cycloalkylalkyl), two $R^5$ groups bound to the same carbon atom become an oxygen atom to form oxo, or two adjacent $R^4$ groups, two adjacent $R^5$ groups, or $R^4$ and $R^5$ are bound to each other to form at least one benzene, pyridine, cyclopentane, cyclohexane, or cycloheptane fused ring; $R^9$ is hydrogen, $C_{1-5}$ alkyl, allyl, or benzyl; and $R^{10}$ and $R^{11}$ are bound to each other to form —O— or $R^{10}$ is hydrogen while $R^{11}$ is hydrogen, hydroxy, or methoxy. An example of a particularly preferable compound is one wherein $R^1$ is hydrogen, methyl, cyclopropylmethyl, phenethyl, furan-2-ylethyl, or thiophen-2-ylethyl; $R^2$ is hydrogen, hydroxy, acetoxy, or methoxy; $R^3$ is hydroxy; —Z— is $C_{2-5}$ alkylene; two $R^5$ groups bound to the same carbon atom become an oxygen atom to form oxo while the remaining 0 to 8 $R^5$ groups and 0 to 3 $R^4$ groups are independently fluoro, chloro, bromo, iodo, nitro, methyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, carboxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl, or amino, two $R^5$ groups bound to the same carbon atom become an oxygen atom to form oxo, or two adjacent $R^4$ groups, two adjacent $R^5$ groups, or $R^4$ and $R^5$ are bound to each other to form a benzene fused ring, $R^9$ is hydrogen or methyl; and $R^{10}$ and $R^{11}$ are bound to each other to form —O—.

It should be noted that the present invention is not limited to the above conditions.

Examples of pharmaceutically preferable salts include such acid addition salts as: inorganic acid salts such as hydrochloride, sulfate, nitrate, hydrobromide, hydroiodide, and phosphate; organic carboxylic acid salts such as acetate, lactate, citrate, oxalate, glutarate, malate, tartarate, fumarate, mandelate, maleate, benzoate, and phthalate; and organic sulfonic acid salts such as methanesulfonate, ethanesulfonate, benzenesulfonate, p-toluenesulfonate, and camphorsulfonate. Among them, hydrochloride, hydrobromide, phosphate, tartarate, methanesulfonate, or the like is preferably used, although salts are not limited to these examples. Further, the compound of the present invention can be used as alkali metal salt or organic ammonium salt when the compound has an acidic functional group such as carboxyl.

The metabolic rate of the compound according to the present invention is slow, and thus, excellent drug efficacy can be sustained for a long period of time.

Among compounds represented by general formula (I) according to the present invention, Compound (i) wherein $R^1$ is cyclopropylmethyl, $R^2$ is hydroxy, $R^3$ is hydroxy, —Z— is propano, m is 1, n is 0, $R^4$ is 7'-hydroxy, $R^9$ is hydrogen, and $R^{10}$ and $R^{11}$ are bound to each other to form —O—

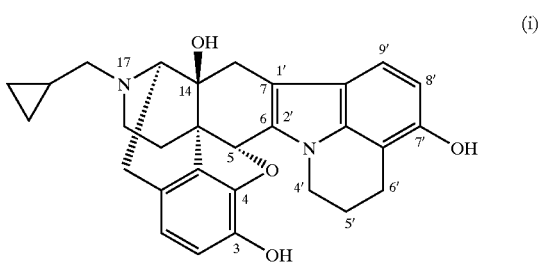

(i)

is designated as 17-cyclopropylmethyl-6,7-didehydro4,5α-epoxy-5',6'-dihydro-4'H-pyrrolo [3,2,1-ij]quinolino[2',1':6,7]morphinan-3,7',14β-triol.

Among compounds represented by general formula (I) according to the present invention, Compound (ii) wherein $R^1$ is cyclopropylmethyl, $R^2$ is hydroxy, $R^3$ is hydroxy, —Z— is propano, m is 0, n is 2, two $R^5$ groups are 6'-oxo, $R^9$ is hydrogen, and $R^{10}$ and $R^{11}$ are bound to each other to form —O—

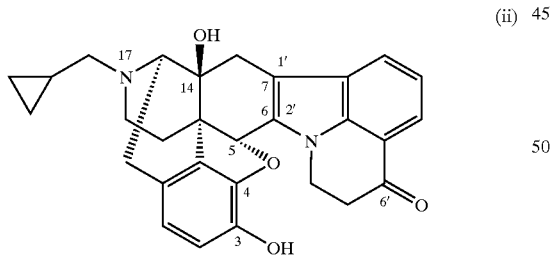

(ii)

is designated as 17-cyclopropylmethyl-6,7-didehydro-4,5α-epoxy-6'-oxo-5',6'-dihydro-4'H-pyrrolo[3,2,1-ij]quinolino[2',1':6,7]morphinan-3,14β-diol.

Among compounds represented by general formula (I) according to the present invention, Compound (iii) wherein $R^1$ is cyclopropylmethyl, $R^2$ is hydroxy, $R^3$ is hydroxy, —Z— is propano, m is 0, n is 1, $R^5$ is 6'α-hydroxy, $R^9$ is hydrogen, and $R^{10}$ and $R^{11}$ are bound to each other to form —O—

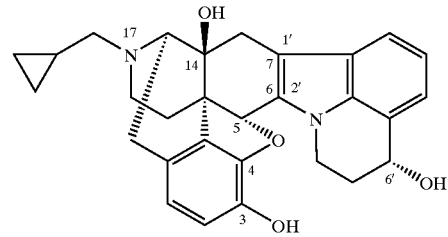

(iii)

is designated as 17-cyclopropylmethyl-6,7-didehydro-4,5α-epoxy-5',6'-dihydro-4'H-pyrrolo[3,2,1-ij]quinolino[2,'1':6,7]morphinan-3,6'α,14β-triol.

The compound of the present invention also includes a compound represented by general formula (IA):

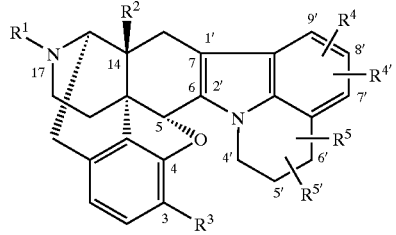

(IA)

wherein
$R^1$, $R^2$, and $R^3$ are as defined in general formula (I); $R^4$, $R^{4'}$, $R^5$, and $R^{5'}$ are independently hydrogen, fluoro, chloro, bromo, iodo, nitro, $C_{1-5}$ alkyl, hydroxy, $C_{1-5}$ alkoxy, trifluoromethyl, trifluoromethoxy, cyano, phenyl, isothiocyanato, $SR^6$, $SOR^6$, $SO_2R^6$, $(CH_2)_p OR^6$, $(CH_2)_p CO_2 R^6$, $SO_2NR^7R^8$, $CONR^7R^8$, $(CH_2)_p NR^7R^8$, or $(CH_2)_p N(R^7)COR^8$ (wherein p is an integer from 0 to 5; $R^6$ is hydrogen or $C_{1-5}$ alkyl; and $R^7$ and $R^8$ are independently hydrogen, $C_{1-5}$ alkyl, or $C_{4-7}$ cycloalkylalkyl); and $R^5$ and $R^{5'}$ bound to the same carbon atom become an oxygen atom to form oxo or two of $R^4$, $R^{4'}$, $R^5$, and $R^{5'}$ are bound to each other to form a benzene, pyridine, cyclopentane, cyclohexane, or cycloheptane fused ring wherein at least one of $R^4$, $R^{4'}$, $R^5$, and $R^{5'}$ should be hydroxy, or $R^5$ and $R^{5'}$ bound to the same carbon atom should become an oxygen atom to form oxo.

According to the present invention, metabolic rate can be lowered by introducing hydroxy and/or oxo as $R^4$ and/or $R^5$. This enables excellent drug efficacy to be sustained for a long period of time, and thus, the frequency of administration can be lowered.

Specific examples of compounds represented by general formula (IA) are shown in Tables 1 to 17.

TABLE 1

| R1 | R2 | R3 | R4 | R4' | R5 | R5' |
|---|---|---|---|---|---|---|
| Me | OH | OH | 7'-OH | H | H | H |
| Me | OH | OH | 7'-OH | 8'-F | H | H |
| Me | OH | OH | 7'-OH | 8'-Me | H | H |
| Me | OH | OH | 7'-OH | 8'-NH2 | H | H |
| Me | OH | OH | 7'-OH | 9'-CO2Et | H | H |
| Me | OH | OH | 8'-OH | H | H | H |
| Me | OH | OH | 8'-OH | 7'-F | H | H |
| Me | OH | OH | 8'-OH | 9'-Me | H | H |
| Me | OH | OH | 8'-OH | 9'-CO2Et | H | H |

TABLE 1-continued

| R1 | R2 | R3 | R4 | R4' | R5 | R5' |
|---|---|---|---|---|---|---|
| Me | OH | OH | 9'-OH | H | H | H |
| Me | OH | OH | 9'-OH | 8'-F | H | H |
| Me | OH | OH | 9'-OH | 7'-Me | H | H |
| Me | OH | OH | 9'-OH | 8'-NH2 | H | H |
| Me | OH | OH | 7'-OH | H | 6'-Me | 6'-Me |
| Me | OH | OH | 7'-OH | 8'-F | 6'-Me | 6'-Me |
| Me | OH | OH | 7'-OH | 8'-CO2Et | 6'-Me | 6'-Me |
| Me | OH | OH | 8'-OH | H | 6'-Me | 6'-Me |
| Me | OH | OH | 8'-OH | 9'-Me | 6'-Me | 6'-Me |
| Me | OH | OH | 9'-OH | H | 6'-Me | 6'-Me |
| Me | OH | OH | 9'-OH | 9'-NH2 | 6'-Me | 6'-Me |
| Me | OH | OH | 7'-OH | H | 5',6'-Benzo | |
| Me | OH | OH | 7'-OH | 8'-F | 5',6'-Benzo | |
| Me | OH | OH | 7'-OH | 8'-CO2Et | 5',6'-Benzo | |
| Me | OH | OH | 8'-OH | H | 5',6'-Benzo | |
| Me | OH | OH | 8'-OH | 9'-Me | 5',6'-Benzo | |
| Me | OH | OH | 9'-OH | H | 5',6'-Benzo | |
| Me | OH | OH | 9'-OH | 9'-NH2 | 5',6'-Benzo | |
| Me | OH | OH | H | H | 4'α-OH | H |
| Me | OH | OH | H | 8'-F | 4'α-OH | H |
| Me | OH | OH | 7'-OH | 8'-CO2Et | 4'α-OH | H |
| Me | OH | OH | 7'-Me | 9'-NH2 | 4'α-OH | H |
| Me | OH | OH | H | H | 4'β-OH | H |
| Me | OH | OH | H | 8'-F | 4'β-OH | H |
| Me | OH | OH | 7'-OH | 8'-CO2Et | 4'β-OH | H |
| Me | OH | OH | 7'-Me | 9'-NH2 | 4'β-OH | H |
| Me | OH | OH | H | H | 5'α-OH | H |
| Me | OH | OH | H | 8'-F | 5'α-OH | H |
| Me | OH | OH | 7'-OH | 8'-CO2Et | 5'α-OH | H |
| Me | OH | OH | 7'-Me | 9'-NH2 | 5'α-OH | H |
| Me | OH | OH | H | H | 5'β-OH | H |
| Me | OH | OH | H | 8'-F | 5'β-OH | H |
| Me | OH | OH | 7'-OH | 8'-CO2Et | 5'β-OH | H |
| Me | OH | OH | 7'-Me | 9'-NH2 | 5'β-OH | H |
| Me | OH | OH | H | H | 6'α-OH | H |
| Me | OH | OH | H | 8'-F | 6'α-OH | H |
| Me | OH | OH | 7'-OH | 8'-CO2Et | 6'α-OH | H |
| Me | OH | OH | 7'-Me | 9'-NH2 | 6'α-OH | H |
| Me | OH | OH | H | H | 6'β-OH | H |
| Me | OH | OH | H | 8'-F | 6'β-OH | H |
| Me | OH | OH | 7'-OH | 8'-CO2Et | 6'β-OH | H |
| Me | OH | OH | H | H | 6'α-OH | 6'β-Me |

TABLE 2

| R1 | R2 | R3 | R4 | R4' | R5 | R5' |
|---|---|---|---|---|---|---|
| Me | OH | OH | H | 8'-F | 6'α-OH | 6'β-Me |
| Me | OH | OH | 7'-OH | 8'-CO2Et | 6'α-OH | 6'β-Me |
| Me | OH | OH | 7'-Me | 9'-NH2 | 6'α-OH | 6'β-Me |
| Me | OH | OH | H | H | 6'β-OH | 6'α-Me |
| Me | OH | OH | H | 8'-F | 6'β-OH | 6'α-Me |
| Me | OH | OH | 7'-OH | 8'-CO2Et | 6'β-OH | 6'α-Me |
| Me | OH | OH | 7'-Me | 9'-NH2 | 6'β-OH | 6'α-Me |
| Me | OH | OH | H | H | 4'-Oxo | |
| Me | OH | OH | H | 8'-F | 4'-Oxo | |
| Me | OH | OH | 7'-OH | 8'-CO2Et | 4'-Oxo | |
| Me | OH | OH | 7'-Me | 9'-NH2 | 4'-Oxo | |
| Me | OH | OH | H | H | 5'-Oxo | |
| Me | OH | OH | H | 8'-F | 5'-Oxo | |
| Me | OH | OH | 7'-OH | 8'-CO2Et | 5'-Oxo | |
| Me | OH | OH | 7'-Me | 9'-NH2 | 5'-Oxo | |
| Me | OH | OH | H | H | 6'-Oxo | |
| Me | OH | OH | H | 8'-F | 6'-Oxo | |
| Me | OH | OH | 7'-OH | 8'-CO2Et | 6'-Oxo | |
| Me | OH | OH | 7'-Me | 9'-NH2 | 6'-Oxo | |
| Cyclopropyl-methyl | OH | OH | 7'-OH | H | H | H |
| Cyclopropyl-methyl | OH | OH | 7'-OH | 8'-F | H | H |
| Cyclopropyl-methyl | OH | OH | 7'-OH | 8'-Me | H | H |
| Cyclopropyl-methyl | OH | OH | 7'-OH | 8'-NH2 | H | H |
| Cyclopropyl-methyl | OH | OH | 7'-OH | 9'-CO2Et | H | H |
| Cyclopropyl-methyl | OH | OH | 8'-OH | H | H | H |
| Cyclopropyl-methyl | OH | OH | 8'-OH | 7'-F | H | H |
| Cyclopropyl-methyl | OH | OH | 8'-OH | 9'-Me | H | H |
| Cyclopropyl-methyl | OH | OH | 8'-OH | 9'-CO2Et | H | H |
| Cyclopropyl-methyl | OH | OH | 9'-OH | H | H | H |
| Cyclopropyl-methyl | OH | OH | 9'-OH | 8'-F | H | H |
| Cyclopropyl-methyl | OH | OH | 9'-OH | 7'-Me | H | H |
| Cyclopropyl-methyl | OH | OH | 9'-OH | 8'-NH2 | H | H |
| Cyclopropyl-methyl | OH | OH | 7'-OH | H | 6'-Me | 6'-Me |
| Cyclopropyl-methyl | OH | OH | 7'-OH | 8'-F | 6'-Me | 6'-Me |
| Cyclopropyl-methyl | OH | OH | 7'-OH | 8'-CO2Et | 6'-Me | 6'-Me |
| Cyclopropyl-methyl | OH | OH | 8'-OH | H | 6'-Me | 6'-Me |
| Cyclopropyl-methyl | OH | OH | 8'-OH | 9'-Me | 6'-Me | 6'-Me |
| Cyclopropyl-methyl | OH | OH | 9'-OH | H | 6'-Me | 6'-Me |
| Cyclopropyl-methyl | OH | OH | 9'-OH | 9'-NH2 | 6'-Me | 6'-Me |
| Cyclopropyl-methyl | OH | OH | 7'-OH | H | 5',6'-Benzo | |
| Cyclopropyl-methyl | OH | OH | 7'-OH | 8'-F | 5',6'-Benzo | |
| Cyclopropyl-methyl | OH | OH | 7'-OH | 8'-CO2Et | 5',6'-Benzo | |
| Cyclopropyl-methyl | OH | OH | 8'-OH | H | 5',6'-Benzo | |
| Cyclopropyl-methyl | OH | OH | 8'-OH | 9'-Me | 5',6'-Benzo | |
| Cyclopropyl-methyl | OH | OH | 9'-OH | H | 5',6'-Benzo | |
| Cyclopropyl-methyl | OH | OH | 9'-OH | 9'-NH2 | 5',6'-Benzo | |
| Cyclopropyl-methyl | OH | OH | H | H | 4'α-OH | H |
| Cyclopropyl-methyl | OH | OH | H | 8'-F | 4'α-OH | H |
| Cyclopropyl-methyl | OH | OH | 7'-OH | 8'-CO2Et | 4'α-OH | H |
| Cyclopropyl-methyl | OH | OH | 7'-Me | 9'-NH2 | 4'α-OH | H |
| Cyclopropyl-methyl | OH | OH | H | H | 4'β-OH | H |

TABLE 3

| R1 | R2 | R3 | R4 | R4' | R5 | R5' |
|---|---|---|---|---|---|---|
| Cyclopropyl-methyl | OH | OH | H | 8'-F | 4'β-OH | H |
| Cyclopropyl-methyl | OH | OH | 7'-OH | 8'-CO2Et | 4'β-OH | H |
| Cyclopropyl-methyl | OH | OH | 7'-Me | 9'-NH2 | 4'β-OH | H |
| Cyclopropyl-methyl | OH | OH | H | H | 5'α-OH | H |
| Cyclopropyl-methyl | OH | OH | H | 8'-F | 5'α-OH | H |
| Cyclopropyl-methyl | OH | OH | 7'-OH | 8'-CO2Et | 5'α-OH | H |
| Cyclopropyl-methyl | OH | OH | 7'-Me | 9'-NH2 | 5'α-OH | H |
| Cyclopropyl- | | | | | | |

TABLE 3-continued

| R1 | R2 | R3 | R4 | R4' | R5 | R5' |
|---|---|---|---|---|---|---|
| methyl | | | | | | |
| Cyclopropyl-methyl | OH | OH | H | H | 5'β-OH | H |
| Cyclopropyl-methyl | OH | OH | H | 8'-F | 5'β-OH | H |
| Cyclopropyl-methyl | OH | OH | 7'-OH | 8'-CO2Et | 5'β-OH | H |
| Cyclopropyl-methyl | OH | OH | 7'-Me | 9'-NH2 | 5'β-OH | H |
| Cyclopropyl-methyl | OH | OH | H | H | 6'α-OH | H |
| Cyclopropyl-methyl | OH | OH | H | 8'-F | 6'α-OH | H |
| Cyclopropyl-methyl | OH | OH | 7'-OH | 8'-CO2Et | 6'α-OH | H |
| Cyclopropyl-methyl | OH | OH | 7'-Me | 9'-NH2 | 6'α-OH | H |
| Cyclopropyl-methyl | OH | OH | H | H | 6'β-OH | H |
| Cyclopropyl-methyl | OH | OH | H | 8'-F | 6'β-OH | H |
| Cyclopropyl-methyl | OH | OH | 7'-OH | 8'-CO2Et | 6'β-OH | H |
| Cyclopropyl-methyl | OH | OH | H | H | 6'α-OH | 6'β-Me |
| Cyclopropyl-methyl | OH | OH | H | 8'-F | 6'α-OH | 6'β-Me |
| Cyclopropyl-methyl | OH | OH | 7'-OH | 8'-CO2Et | 6'α-OH | 6'β-Me |
| Cyclopropyl-methyl | OH | OH | 7'-Me | 9'-NH2 | 6'α-OH | 6'β-Me |
| Cyclopropyl-methyl | OH | OH | H | H | 6'β-OH | 6'α-Me |
| Cyclopropyl-methyl | OH | OH | H | 8'-F | 6'β-OH | 6'α-Me |
| Cyclopropyl-methyl | OH | OH | 7'-OH | 8'-CO2Et | 6'β-OH | 6'α-Me |
| Cyclopropyl-methyl | OH | OH | 7'-Me | 9'-NH2 | 6'β-OH | 6'α-Me |
| Cyclopropyl-methyl | OH | OH | H | H | 4'-Oxo | |
| Cyclopropyl-methyl | OH | OH | H | 8'-F | 4'-Oxo | |
| Cyclopropyl-methyl | OH | OH | 7'-OH | 8'-CO2Et | 4'-Oxo | |
| Cyclopropyl-methyl | OH | OH | 7'-Me | 9'-NH2 | 4'-Oxo | |
| Cyclopropyl-methyl | OH | OH | H | H | 5'-Oxo | |
| Cyclopropyl-methyl | OH | OH | H | 8'-F | 5'-Oxo | |
| Cyclopropyl-methyl | OH | OH | 7'-OH | 8'-CO2Et | 5'-Oxo | |
| Cyclopropyl-methyl | OH | OH | 7'-Me | 9'-NH2 | 5'-Oxo | |
| Cyclopropyl-methyl | OH | OH | H | H | 6'-Oxo | |
| Cyclopropyl-methyl | OH | OH | H | 8'-F | 6'-Oxo | |
| Cyclopropyl-methyl | OH | OH | 7'-OH | 8'-CO2Et | 6'-Oxo | |
| Cyclopropyl-methyl | OH | OH | 7'-Me | 9'-NH2 | 6'-Oxo | |
| H | OH | OH | 7'-OH | H | H | H |
| H | OH | OH | 7'-OH | 8'-F | H | H |
| H | OH | OH | 7'-OH | 8'-Me | H | H |
| H | OH | OH | 7'-OH | 8'-NH2 | H | H |
| H | OH | OH | 7'-OH | 9'-CO2Et | H | H |
| H | OH | OH | 8'-OH | H | H | H |
| H | OH | OH | 8'-OH | 7'-F | H | H |
| H | OH | OH | 8'-OH | 9'-Me | H | H |
| H | OH | OH | 8'-OH | 9'-CO2Et | H | H |
| H | OH | OH | 9'-OH | H | H | H |
| H | OH | OH | 9'-OH | 8'-F | H | H |
| H | OH | OH | 9'-OH | 7'-Me | H | H |
| H | OH | OH | 9'-OH | 8'-NH2 | H | H |

TABLE 4

| R1 | R2 | R3 | R4 | R4' | R5 | R5' |
|---|---|---|---|---|---|---|
| H | OH | OH | 7'-OH | H | 6'-Me | 6'-Me |
| H | OH | OH | 7'-OH | 8'-F | 6'-Me | 6'-Me |
| H | OH | OH | 7'-OH | 8'-CO2Et | 6'-Me | 6'-Me |
| H | OH | OH | 8'-OH | H | 6'-Me | 6'-Me |
| H | OH | OH | 8'-OH | 9'-Me | 6'-Me | 6'-Me |
| H | OH | OH | 9'-OH | H | 6'-Me | 6'-Me |
| H | OH | OH | 9'-OH | 9'-NH2 | 6'-Me | 6'-Me |
| H | OH | OH | 7'-OH | H | 5',6'-Benzo | |
| H | OH | OH | 7'-OH | 8'-F | 5',6'-Benzo | |
| H | OH | OH | 7'-OH | 8'-CO2Et | 5',6'-Benzo | |
| H | OH | OH | 8'-OH | H | 5',6'-Benzo | |
| H | OH | OH | 8'-OH | 9'-Me | 5',6'-Benzo | |
| H | OH | OH | 9'-OH | H | 5',6'-Benzo | |
| H | OH | OH | 9'-OH | 9'-NH2 | 5',6'-Benzo | |
| H | OH | OH | H | H | 4'α-OH | H |
| H | OH | OH | H | 8'-F | 4'α-OH | H |
| H | OH | OH | 7'-OH | 8'-CO2Et | 4'α-OH | H |
| H | OH | OH | 7'-Me | 9'-NH2 | 4'α-OH | H |
| H | OH | OH | H | H | 4'β-OH | H |
| H | OH | OH | H | 8'-F | 4'β-OH | H |
| H | OH | OH | 7'-OH | 8'-CO2Et | 4'β-OH | H |
| H | OH | OH | 7'-Me | 9'-NH2 | 4'β-OH | H |
| H | OH | OH | H | H | 5'α-OH | H |
| H | OH | OH | H | 8'-F | 5'α-OH | H |
| H | OH | OH | 7'-OH | 8'-CO2Et | 5'α-OH | H |
| H | OH | OH | 7'-Me | 9'-NH2 | 5'α-OH | H |
| H | OH | OH | H | H | 5'β-OH | H |
| H | OH | OH | H | 8'-F | 5'β-OH | H |
| H | OH | OH | 7'-OH | 8'-CO2Et | 5'β-OH | H |
| H | OH | OH | 7'-Me | 9'-NH2 | 5'β-OH | H |
| H | OH | OH | H | H | 6'α-OH | H |
| H | OH | OH | H | 8'-F | 6'α-OH | H |
| H | OH | OH | 7'-OH | 8'-CO2Et | 6'α-OH | H |
| H | OH | OH | 7'-Me | 9'-NH2 | 6'α-OH | H |
| H | OH | OH | H | H | 6'β-OH | H |
| H | OH | OH | H | 8'-F | 6'β-OH | H |
| H | OH | OH | 7'-OH | 8'-CO2Et | 6'β-OH | H |
| H | OH | OH | H | H | 6'α-OH | 6'β-Me |
| H | OH | OH | H | 8'-F | 6'α-OH | 6'β-Me |
| H | OH | OH | 7'-OH | 8'-CO2Et | 6'α-OH | 6'β-Me |
| H | OH | OH | 7'-Me | 9'-NH2 | 6'α-OH | 6'β-Me |
| H | OH | OH | H | H | 6'β-OH | 6'α-Me |
| H | OH | OH | H | 8'-F | 6'β-OH | 6'α-Me |
| H | OH | OH | 7'-OH | 8'-CO2Et | 6'β-OH | 6'α-Me |
| H | OH | OH | 7'-Me | 9'-NH2 | 6'β-OH | 6'α-Me |
| H | OH | OH | H | H | 4'-Oxo | |
| H | OH | OH | H | 8'-F | 4'-Oxo | |
| H | OH | OH | 7'-OH | 8'-CO2Et | 4'-Oxo | |
| H | OH | OH | 7'-Me | 9'-NH2 | 4'-Oxo | |
| H | OH | OH | H | H | 5'-Oxo | |
| H | OH | OH | H | 8'-F | 5'-Oxo | |

TABLE 5

| R1 | R2 | R3 | R4 | R4' | R5 | R5' |
|---|---|---|---|---|---|---|
| H | OH | OH | 7'-OH | 8'-CO2Et | 5'-Oxo | |
| H | OH | OH | 7'-Me | 9'-NH2 | 5'-Oxo | |
| H | OH | OH | H | H | 6'-Oxo | |
| H | OH | OH | H | 8'-F | 6'-Oxo | |
| H | OH | OH | 7'-OH | 8'-CO2Et | 6'-Oxo | |
| H | OH | OH | 7'-Me | 9'-NH2 | 6'-Oxo | |
| CH2CH2Ph | OH | OH | 7'-OH | H | H | H |
| CH2CH2Ph | OH | OH | 7'-OH | 8'-F | H | H |
| CH2CH2Ph | OH | OH | 7'-OH | 8'-Me | H | H |
| CH2CH2Ph | OH | OH | 7'-OH | 8'-NH2 | H | H |
| CH2CH2Ph | OH | OH | 7'-OH | 9'-CO2Et | H | H |
| CH2CH2Ph | OH | OH | 8'-OH | H | H | H |
| CH2CH2Ph | OH | OH | 8'-OH | 7'-F | H | H |
| CH2CH2Ph | OH | OH | 8'-OH | 9'-Me | H | H |
| CH2CH2Ph | OH | OH | 8'-OH | 9'-CO2Et | H | H |
| CH2CH2Ph | OH | OH | 9'-OH | H | H | H |
| CH2CH2Ph | OH | OH | 9'-OH | 8'-F | H | H |
| CH2CH2Ph | OH | OH | 9'-OH | 7'-Me | H | H |

TABLE 5-continued

| R1 | R2 | R3 | R4 | R4' | R5 | R5' |
|---|---|---|---|---|---|---|
| CH2CH2Ph | OH | OH | 9'-OH | 8'-NH2 | H | H |
| CH2CH2Ph | OH | OH | 7'-OH | H | 6'-Me | 6'-Me |
| CH2CH2Ph | OH | OH | 7'-OH | 8'-F | 6'-Me | 6'-Me |
| CH2CH2Ph | OH | OH | 7'-OH | 8'-CO2Et | 6'-Me | 6'-Me |
| CH2CH2Ph | OH | OH | 8'-OH | H | 6'-Me | 6'-Me |
| CH2CH2Ph | OH | OH | 8'-OH | 9'-Me | 6'-Me | 6'-Me |
| CH2CH2Ph | OH | OH | 9'-OH | H | 6'-Me | 6'-Me |
| CH2CH2Ph | OH | OH | 9'-OH | 9'-NH2 | 6'-Me | 6'-Me |
| CH2CH2Ph | OH | OH | 7'-OH | H | 5',6'-Benzo | |
| CH2CH2Ph | OH | OH | 7'-OH | 8'-F | 5',6'-Benzo | |
| CH2CH2Ph | OH | OH | 7'-OH | 8'-CO2Et | 5',6'-Benzo | |
| CH2CH2Ph | OH | OH | 8'-OH | H | 5',6'-Benzo | |
| CH2CH2Ph | OH | OH | 8'-OH | 9'-Me | 5',6'-Benzo | |
| CH2CH2Ph | OH | OH | 9'-OH | H | 5',6'-Benzo | |
| CH2CH2Ph | OH | OH | 9'-OH | 9'-NH2 | 5',6'-Benzo | |
| CH2CH2Ph | OH | OH | H | H | 4'α-OH | H |
| CH2CH2Ph | OH | OH | H | 8'-F | 4'α-OH | H |
| CH2CH2Ph | OH | OH | 7'-OH | 8'-CO2Et | 4'α-OH | H |
| CH2CH2Ph | OH | OH | 7'-Me | 9'-NH2 | 4'α-OH | H |
| CH2CH2Ph | OH | OH | H | H | 4'β-OH | H |
| CH2CH2Ph | OH | OH | H | 8'-F | 4'β-OH | H |
| CH2CH2Ph | OH | OH | 7'-OH | 8'-CO2Et | 4'β-OH | H |
| CH2CH2Ph | OH | OH | 7'-Me | 9'-NH2 | 4'β-OH | H |
| CH2CH2Ph | OH | OH | H | H | 5'α-OH | H |
| CH2CH2Ph | OH | OH | H | 8'-F | 5'α-OH | H |
| CH2CH2Ph | OH | OH | 7'-OH | 8'-CO2Et | 5'α-OH | H |
| CH2CH2Ph | OH | OH | 7'-Me | 9'-NH2 | 5'α-OH | H |
| CH2CH2Ph | OH | OH | H | H | 5'β-OH | H |
| CH2CH2Ph | OH | OH | H | 8'-F | 5'β-OH | H |
| CH2CH2Ph | OH | OH | 7'-OH | 8'-CO2Et | 5'β-OH | H |
| CH2CH2Ph | OH | OH | 7'-Me | 9'-NH2 | 5'β-OH | H |
| CH2CH2Ph | OH | OH | H | H | 6'α-OH | H |
| CH2CH2Ph | OH | OH | H | 8'-F | 6'α-OH | H |

TABLE 6

| R1 | R2 | R3 | R4 | R4' | R5 | R5' |
|---|---|---|---|---|---|---|
| CH2CH2Ph | OH | OH | 7'-OH | 8'-CO2Et | 6'α-OH | H |
| CH2CH2Ph | OH | OH | 7'-Me | 9'-NH2 | 6'α-OH | H |
| CH2CH2Ph | OH | OH | H | H | 6'β-OH | H |
| CH2CH2Ph | OH | OH | H | 8'-F | 6'β-OH | H |
| CH2CH2Ph | OH | OH | 7'-OH | 8'-CO2Et | 6'β-OH | H |
| CH2CH2Ph | OH | OH | H | H | 6'α-OH | 6'β-Me |
| CH2CH2Ph | OH | OH | H | 8'-F | 6'α-OH | 6'β-Me |
| CH2CH2Ph | OH | OH | 7'-OH | 8'-CO2Et | 6'α-OH | 6'β-Me |
| CH2CH2Ph | OH | OH | 7'-Me | 9'-NH2 | 6'α-OH | 6'β-Me |
| CH2CH2Ph | OH | OH | H | H | 6'β-OH | 6'α-Me |
| CH2CH2Ph | OH | OH | H | 8'-F | 6'β-OH | 6'α-Me |
| CH2CH2Ph | OH | OH | 7'-OH | 8'-CO2Et | 6'β-OH | 6'α-Me |
| CH2CH2Ph | OH | OH | 7'-Me | 9'-NH2 | 6'β-OH | 6'α-Me |
| CH2CH2Ph | OH | OH | H | H | 4'-Oxo | |
| CH2CH2Ph | OH | OH | H | 8'-F | 4'-Oxo | |
| CH2CH2Ph | OH | OH | 7'-OH | 8'-CO2Et | 4'-Oxo | |
| CH2CH2Ph | OH | OH | 7'-Me | 9'-NH2 | 4'-Oxo | |
| CH2CH2Ph | OH | OH | H | H | 5'-Oxo | |
| CH2CH2Ph | OH | OH | H | 8'-F | 5'-Oxo | |
| CH2CH2Ph | OH | OH | 7'-OH | 8'-CO2Et | 5'-Oxo | |
| CH2CH2Ph | OH | OH | 7'-Me | 9'-NH2 | 5'-Oxo | |
| CH2CH2Ph | OH | OH | H | H | 6'-Oxo | |
| CH2CH2Ph | OH | OH | H | 8'-F | 6'-Oxo | |
| CH2CH2Ph | OH | OH | 7'-OH | 8'-CO2Et | 6'-Oxo | |
| CH2CH2Ph | OH | OH | 7'-Me | 9'-NH2 | 6'-Oxo | |
| Allyl | OH | OH | 7'-OH | H | H | H |
| Allyl | OH | OH | 7'-OH | 8'-F | H | H |
| Allyl | OH | OH | 7'-OH | 8'-Me | H | H |
| Allyl | OH | OH | 7'-OH | 8'-CO2Et | H | H |
| Allyl | OH | OH | 8'-OH | H | H | H |
| Allyl | OH | OH | 8'-OH | 9'-Me | H | H |
| Allyl | OH | OH | 8'-OH | 9'-NH2 | H | H |
| Allyl | OH | OH | 9'-OH | H | H | H |
| Allyl | OH | OH | 9'-OH | 8'-F | H | H |
| Allyl | OH | OH | 7'-OH | H | 6'-Me | 6'-Me |
| Allyl | OH | OH | 7'-OH | 8'-F | 6'-Me | 6'-Me |

TABLE 6-continued

| R1 | R2 | R3 | R4 | R4' | R5 | R5' |
|---|---|---|---|---|---|---|
| Allyl | OH | OH | 7'-OH | 8'-CO2Et | 6'-Me | 6'-Me |
| Allyl | OH | OH | 8'-OH | H | 6'-Me | 6'-Me |
| Allyl | OH | OH | 8'-OH | 9'-Me | 6'-Me | 6'-Me |
| Allyl | OH | OH | 9'-OH | H | 6'-Me | 6'-Me |
| Allyl | OH | OH | 9'-OH | 9'-NH2 | 6'-Me | 6'-Me |
| Allyl | OH | OH | 7'-OH | H | 5',6'-Benzo | |
| Allyl | OH | OH | 7'-OH | 8'-F | 5',6'-Benzo | |
| Allyl | OH | OH | 7'-OH | 8'-CO2Et | 5',6'-Benzo | |
| Allyl | OH | OH | 8'-OH | H | 5',6'-Benzo | |
| Allyl | OH | OH | 8'-OH | 9'-Me | 5',6'-Benzo | |
| Allyl | OH | OH | 9'-OH | H | 5',6'-Benzo | |
| Allyl | OH | OH | 9'-OH | 9'-NH2 | 5',6'-Benzo | |
| Allyl | OH | OH | H | H | 4'α-OH | H |
| Allyl | OH | OH | H | 8'-F | 4'α-OH | H |
| Allyl | OH | OH | 7'-OH | 8'-CO2Et | 4'α-OH | H |

TABLE 7

| R1 | R2 | R3 | R4 | R4' | R5 | R5' |
|---|---|---|---|---|---|---|
| Allyl | OH | OH | 7'-Me | 9'-NH2 | 4'β-OH | H |
| Allyl | OH | OH | H | H | 4'β-OH | H |
| Allyl | OH | OH | H | 8'-F | 4'β-OH | H |
| Allyl | OH | OH | 7'-OH | 8'-CO2Et | 4'β-OH | H |
| Allyl | OH | OH | 7'-Me | 9'-NH2 | 4'β-OH | H |
| Allyl | OH | OH | H | H | 5'α-OH | H |
| Allyl | OH | OH | H | 8'-F | 5'α-OH | H |
| Allyl | OH | OH | H | H | 5'β-OH | H |
| Allyl | OH | OH | H | 8'-F | 5'β-OH | H |
| Allyl | OH | OH | H | H | 6'α-OH | H |
| Allyl | OH | OH | H | 8'-F | 6'α-OH | H |
| Allyl | OH | OH | H | H | 6'β-OH | H |
| Allyl | OH | OH | H | 8'-F | 6'β-OH | H |
| Allyl | OH | OH | H | H | 6'α-OH | 6'β-Me |
| Allyl | OH | OH | H | 8'-F | 6'α-OH | 6'β-Me |
| Allyl | OH | OH | 7'-OH | 8'-CO2Et | 6'α-OH | 6'β-Me |
| Allyl | OH | OH | 7'-Me | 9'-NH2 | 6'α-OH | 6'β-Me |
| Allyl | OH | OH | H | H | 6'β-OH | 6'α-Me |
| Allyl | OH | OH | H | 8'-F | 6'β-OH | 6'α-Me |
| Allyl | OH | OH | 7'-OH | 8'-CO2Et | 6'β-OH | 6'α-Me |
| Allyl | OH | OH | 7'-Me | 9'-NH2 | 6'β-OH | 6'α-Me |
| Allyl | OH | OH | H | H | 4'-Oxo | |
| Allyl | OH | OH | H | 8'-F | 4'-Oxo | |
| Allyl | OH | OH | H | H | 5'-Oxo | |
| Allyl | OH | OH | H | H | 6'-Oxo | |
| Allyl | OH | OH | H | 8'-F | 6'-Oxo | |
| Benzyl | OH | OH | 7'-OH | H | H | H |
| Benzyl | OH | OH | 7'-OH | 8'-F | H | H |
| Benzyl | OH | OH | 7'-OH | 8'-Me | H | H |
| Benzyl | OH | OH | 7'-OH | 8'-CO2Et | H | H |
| Benzyl | OH | OH | 8'-OH | H | H | H |
| Benzyl | OH | OH | 8'-OH | 9'-Me | H | H |
| Benzyl | OH | OH | 8'-OH | 9'-NH2 | H | H |
| Benzyl | OH | OH | 9'-OH | H | H | H |
| Benzyl | OH | OH | 9'-OH | 8'-F | H | H |
| Benzyl | OH | OH | 7'-OH | H | 6'-Me | 6'-Me |
| Benzyl | OH | OH | 7'-OH | 8'-F | 6'-Me | 6'-Me |
| Benzyl | OH | OH | 7'-OH | 8'-CO2Et | 6'-Me | 6'-Me |
| Benzyl | OH | OH | 8'-OH | H | 6'-Me | 6'-Me |
| Benzyl | OH | OH | 8'-OH | 9'-Me | 6'-Me | 6'-Me |
| Benzyl | OH | OH | 9'-OH | H | 6'-Me | 6'-Me |
| Benzyl | OH | OH | 9'-OH | 9'-NH2 | 6'-Me | 6'-Me |
| Benzyl | OH | OH | 7'-OH | H | 5',6'-Benzo | |
| Benzyl | OH | OH | 7'-OH | 8'-F | 5',6'-Benzo | |
| Benzyl | OH | OH | 7'-OH | 8'-CO2Et | 5',6'-Benzo | |
| Benzyl | OH | OH | 8'-OH | H | 5',6'-Benzo | |
| Benzyl | OH | OH | 8'-OH | 9'-Me | 5',6'-Benzo | |
| Benzyl | OH | OH | 9'-OH | H | 5',6'-Benzo | |
| Benzyl | OH | OH | 9'-OH | 9'-NH2 | 5',6'-Benzo | |
| Benzyl | OH | OH | H | H | 4'α-OH | H |
| Benzyl | OH | H | H | 8'-F | 4'α-OH | H |

TABLE 8

| R1 | R2 | R3 | R4 | R4' | R5 | R5' |
|---|---|---|---|---|---|---|
| Benzyl | OH | OH | 7'-OH | 8'-CO2Et | 4'α-OH | H |
| Benzyl | OH | OH | 7'-Me | 9'-NH2 | 4'α-OH | H |
| Benzyl | OH | OH | H | H | 4'β-OH | H |
| Benzyl | OH | OH | H | 8'-F | 4'β-OH | H |
| Benzyl | OH | OH | 7'-OH | 8'-CO2Et | 4'β-OH | H |
| Benzyl | OH | OH | 7'-Me | 9'-NH2 | 4'β-OH | H |
| Benzyl | OH | OH | H | H | 5'α-OH | H |
| Benzyl | OH | OH | H | 8'-F | 5'α-OH | H |
| Benzyl | OH | OH | H | H | 5'β-OH | H |
| Benzyl | OH | OH | H | 8'-F | 5'β-OH | H |
| Benzyl | OH | OH | H | H | 6'α-OH | H |
| Benzyl | OH | OH | H | 8'-F | 6'α-OH | H |
| Benzyl | OH | OH | H | H | 6'β-OH | H |
| Benzyl | OH | OH | H | 8'-F | 6'β-OH | H |
| Benzyl | OH | OH | H | H | 6'α-OH | 6'β-Me |
| Benzyl | OH | OH | H | 8'-F | 6'α-OH | 6'β-Me |
| Benzyl | OH | OH | 7'-OH | 8'-CO2Et | 6'α-OH | 6'β-Me |
| Benzyl | OH | OH | 7'-Me | 9'-NH2 | 6'α-OH | 6'β-Me |
| Benzyl | OH | OH | H | H | 6'β-OH | 6'α-Me |
| Benzyl | OH | OH | H | 8'-F | 6'β-OH | 6'α-Me |
| Benzyl | OH | OH | 7'-OH | 8'-CO2Et | 6'β-OH | 6'α-Me |
| Benzyl | OH | OH | 7'-Me | 9'-NH2 | 6'β-OH | 6'α-Me |
| Benzyl | OH | OH | H | H | 4'-Oxo | |
| Benzyl | OH | OH | H | 8'-F | 4'-Oxo | |
| Benzyl | OH | OH | H | 8'-F | 5'-Oxo | |
| Benzyl | OH | OH | H | H | 6'-Oxo | |
| Benzyl | OH | OH | H | 8'-F | 6'-Oxo | |
| 2-Thienylethyl | OH | OH | 7'-OH | H | H | H |
| 2-Thienylethyl | OH | OH | 7'-OH | 8'-F | H | H |
| 2-Thienylethyl | OH | OH | 7'-OH | 8'-Me | H | H |
| 2-Thienylethyl | OH | OH | 7'-OH | 8'-CO2Et | H | H |
| 2-Thienylethyl | OH | OH | 8'-OH | H | H | H |
| 2-Thienylethyl | OH | OH | 8'-OH | 9'-Me | H | H |
| 2-Thienylethyl | OH | OH | 8'-OH | 9'-NH2 | H | H |
| 2-Thienylethyl | OH | OH | 9'-OH | H | H | H |
| 2-Thienylethyl | OH | OH | 9'-OH | 8'-F | H | H |
| 2-Thienylethyl | OH | OH | 7'-OH | H | 6'-Me | 6'-Me |
| 2-Thienylethyl | OH | OH | 7'-OH | 8'-F | 6'-Me | 6'-Me |
| 2-Thienylethyl | OH | OH | 7'-OH | 8'-CO2Et | 6'-Me | 6'-Me |
| 2-Thienylethyl | OH | OH | 8'-OH | H | 6'-Me | 6'-Me |
| 2-Thienylethyl | OH | OH | 8'-OH | 9'-Me | 6'-Me | 6'-Me |
| 2-Thienylethyl | OH | OH | 9'-OH | H | 6'-Me | 6'-Me |
| 2-Thienylethyl | OH | OH | 9'-OH | 9'-NH2 | 6'-Me | 6'-Me |
| 2-Thienylethyl | OH | OH | 7'-OH | H | 5',6'-Benzo | |
| 2-Thienylethyl | OH | OH | 7'-OH | 8'-F | 5',6'-Benzo | |
| 2-Thienylethyl | OH | OH | 7'-OH | 8'-CO2Et | 5',6'-Benzo | |
| 2-Thienylethyl | OH | OH | 8'-OH | H | 5',6'-Benzo | |
| 2-Thienylethyl | OH | OH | 8'-OH | 9'-Me | 5',6'-Benzo | |
| 2-Thienylethyl | OH | OH | 9'-OH | H | 5',6'-Benzo | |
| 2-Thienylethyl | OH | OH | 9'-OH | 9'-NH2 | 5',6'-Benzo | |
| 2-Thienylethyl | OH | OH | H | H | 4'α-OH | H |

TABLE 9

| R1 | R2 | R3 | R4 | R4' | R5 | R5' |
|---|---|---|---|---|---|---|
| 2-Thienylethyl | OH | OH | H | 8'-F | 4'α-OH | H |
| 2-Thienylethyl | OH | OH | 7'-OH | 8'-CO2Et | 4'α-OH | H |
| 2-Thienylethyl | OH | OH | 7'-Me | 9'-NH2 | 4'α-OH | H |
| 2-Thienylethyl | OH | OH | H | H | 4'β-OH | H |
| 2-Thienylethyl | OH | OH | H | 8'-F | 4'β-OH | H |
| 2-Thienylethyl | OH | OH | 7'-OH | 8'-CO2Et | 4'β-OH | H |
| 2-Thienylethyl | OH | OH | 7'-Me | 9'-NH2 | 4'β-OH | H |
| 2-Thienylethyl | OH | OH | H | H | 5'α-OH | H |
| 2-Thienylethyl | OH | OH | H | 8'-F | 5'α-OH | H |
| 2-Thienylethyl | OH | OH | H | H | 5'β-OH | H |
| 2-Thienylethyl | OH | OH | H | 8'-F | 5'β-OH | H |
| 2-Thienylethyl | OH | OH | H | H | 6'α-OH | H |
| 2-Thienylethyl | OH | OH | H | 8'-F | 6'α-OH | H |
| 2-Thienylethyl | OH | OH | H | H | 6'β-OH | H |
| 2-Thienylethyl | OH | OH | H | 8'-F | 6'β-OH | H |
| 2-Thienylethyl | OH | OH | H | H | 6'α-OH | 6'β-Me |
| 2-Thienylethyl | OH | OH | H | 8'-F | 6'α-OH | 6'β-Me |
| 2-Thienylethyl | OH | OH | 7'-OH | 8'-CO2Et | 6'α-OH | 6'β-Me |
| 2-Thienylethyl | OH | OH | 7'-Me | 9'-NH2 | 6'α-OH | 6'β-Me |
| 2-Thienylethyl | OH | OH | H | H | 6'β-OH | 6'α-Me |
| 2-Thienylethyl | OH | OH | H | 8'-F | 6'β-OH | 6'α-Me |
| 2-Thienylethyl | OH | OH | 7'-OH | 8'-CO2Et | 6'β-OH | 6'α-Me |
| 2-Thienylethyl | OH | OH | 7'-Me | 9'-NH2 | 6'β-OH | 6'α-Me |
| 2-Thienylethyl | OH | OH | H | H | 4'-Oxo | |
| 2-Thienylethyl | OH | OH | H | 8'-F | 4'-Oxo | |
| 2-Thienylethyl | OH | OH | H | 8'-F | 5'-Oxo | |
| 2-Thienylethyl | OH | OH | H | H | 6'-Oxo | |
| 2-Thienylethyl | OH | OH | H | 8'-F | 6'-Oxo | |
| Me | OMe | OH | 7'-OH | H | H | H |
| Me | OMe | OH | 7'-OH | 8'-F | H | H |
| Me | OMe | OH | 7'-OH | 8'-Me | H | H |
| Me | OMe | OH | 7'-OH | 8'-NH2 | H | H |
| Me | OMe | OH | 7'-OH | 9'-CO2Et | H | H |
| Me | OMe | OH | 8'-OH | H | H | H |
| Me | OMe | OH | 8'-OH | 7'-F | H | H |
| Me | OMe | OH | 8'-OH | 9'-Me | H | H |
| Me | OMe | OH | 8'-OH | 9'-CO2Et | H | H |
| Me | OMe | OH | 9'-OH | H | H | H |
| Me | OMe | OH | 9'-OH | 8'-F | H | H |
| Me | OMe | OH | 9'-OH | 7'-Me | H | H |
| Me | OMe | OH | 9'-OH | 8'-NH2 | H | H |
| Me | OMe | OH | 7'-OH | H | 6'-Me | 6'-Me |
| Me | OMe | OH | 7'-OH | 8'-F | 6'-Me | 6'-Me |
| Me | OMe | OH | 7'-OH | 8'-CO2Et | 6'-Me | 6'-Me |
| Me | OMe | OH | 8'-OH | H | 6'-Me | 6'-Me |
| Me | OMe | OH | 8'-OH | 9'-Me | 6'-Me | 6'-Me |
| Me | OMe | OH | 9'-OH | H | 6'-Me | 6'-Me |
| Me | OMe | OH | 9'-OH | 9'-NH2 | 6'-Me | 6'-Me |
| Me | OMe | OH | 7'-OH | H | 5',6'-Benzo | |
| Me | OMe | OH | 7'-OH | 8'-F | 5',6'-Benzo | |
| Me | OMe | OH | 7'-OH | 8'-CO2Et | 5',6'-Benzo | |

TABLE 10

| R1 | R2 | R3 | R4 | R4' | R5 | R5' |
|---|---|---|---|---|---|---|
| Me | OMe | OH | 8'-OH | H | 5',6'-Benzo | |
| Me | OMe | OH | 8'-OH | 9'-Me | 5',6'-Benzo | |
| Me | OMe | OH | 9'-OH | H | 5',6'-Benzo | |
| Me | OMe | OH | 9'-OH | 9'-NH2 | 5',6'-Benzo | |
| Me | OMe | OH | H | H | 4'α-OH | H |
| Me | OMe | OH | H | 8'-F | 4'α-OH | H |
| Me | OMe | OH | 7'-OH | 8'-CO2Et | 4'α-OH | H |
| Me | OMe | OH | 7'-Me | 9'-NH2 | 4'α-OH | H |
| Me | OMe | OH | H | H | 4'β-OH | H |
| Me | OMe | OH | H | 8'-F | 4'β-OH | H |
| Me | OMe | OH | 7'-OH | 8'-CO2Et | 4'β-OH | H |
| Me | OMe | OH | 7'-Me | 9'-NH2 | 4'β-OH | H |
| Me | OMe | OH | H | H | 5'α-OH | H |
| Me | OMe | OH | H | 8'-F | 5'α-OH | H |
| Me | OMe | OH | 7'-OH | 8'-CO2Et | 5'α-OH | H |
| Me | OMe | OH | 7'-Me | 9'-NH2 | 5'α-OH | H |
| Me | OMe | OH | H | H | 5'β-OH | H |
| Me | OMe | OH | H | 8'-F | 5'β-OH | H |
| Me | OMe | OH | 7'-OH | 8'-CO2Et | 5'β-OH | H |
| Me | OMe | OH | 7'-Me | 9'-NH2 | 5'β-OH | H |
| Me | OMe | OH | H | H | 6'α-OH | H |
| Me | OMe | OH | H | 8'-F | 6'α-OH | H |
| Me | OMe | OH | 7'-OH | 8'-CO2Et | 6'α-OH | H |
| Me | OMe | OH | 7'-Me | 9'-NH2 | 6'α-OH | H |
| Me | OMe | OH | H | H | 6'β-OH | H |
| Me | OMe | OH | H | 8'-F | 6'β-OH | H |
| Me | OMe | OH | 7'-OH | 8'-CO2Et | 6'β-OH | H |
| Me | OMe | OH | H | H | 6'α-OH | 6'β-Me |
| Me | OMe | OH | H | 8'-F | 6'α-OH | 6'β-Me |
| Me | OMe | OH | 7'-OH | 8'-CO2Et | 6'α-OH | 6'β-Me |
| Me | OMe | OH | 7'-Me | 9'-NH2 | 6'α-OH | 6'β-Me |
| Me | OMe | OH | H | H | 6'β-OH | 6'α-Me |
| Me | OMe | OH | H | 8'-F | 6'β-OH | 6'α-Me |
| Me | OMe | OH | 7'-OH | 8'-CO2Et | 6'β-OH | 6'α-Me |
| Me | OMe | OH | 7'-Me | 9'-NH2 | 6'β-OH | 6'α-Me |
| Me | OMe | OH | H | H | 4'-Oxo | |

TABLE 10-continued

| R1 | R2 | R3 | R4 | R4' | R5 | R5' |
|---|---|---|---|---|---|---|
| Me | OMe | OH | H | 8'-F | 4'-Oxo | |
| Me | OMe | OH | 7'-OH | 8'-CO2Et | 4'-Oxo | |
| Me | OMe | OH | 7'-Me | 9'-NH2 | 4'-Oxo | |
| Me | OMe | OH | H | H | 5'-Oxo | |
| Me | OMe | OH | H | 8'-F | 5'-Oxo | |
| Me | OMe | OH | 7'-OH | 8'-CO2Et | 5'-Oxo | |
| Me | OMe | OH | 7'-Me | 9'-NH2 | 5'-Oxo | |
| Me | OMe | OH | H | H | 6'-Oxo | |
| Me | OMe | OH | H | 8'-F | 6'-Oxo | |
| Me | OMe | OH | 7'-OH | 8'-CO2Et | 6'-Oxo | |
| Me | OMe | OH | 7'-Me | 9'-NH2 | 6'-Oxo | |
| Cyclopropyl-methyl | OMe | OH | 7'-OH | H | H | H |
| Cyclopropyl-methyl | OMe | OH | 7'-OH | 8'-F | H | H |
| Cyclopropyl-methyl | OMe | OH | 7'-OH | 8'-Me | H | H |
| Cyclopropyl-methyl | OMe | OH | 7'-OH | 8'-NH2 | H | H |

TABLE 11

| R1 | R2 | R3 | R4 | R4' | R5 | R5' |
|---|---|---|---|---|---|---|
| Cyclopropyl-methyl | OMe | OH | 7'-OH | 9'-CO2Et | H | H |
| Cyclopropyl-methyl | OMe | OH | 8'-OH | H | H | H |
| Cyclopropyl-methyl | OMe | OH | 8'-OH | 7'-F | H | H |
| Cyclopropyl-methyl | OMe | OH | 8'-OH | 9'-Me | H | H |
| Cyclopropyl-methyl | OMe | OH | 8'-OH | 9'-CO2Et | H | H |
| Cyclopropyl-methyl | OMe | OH | 9'-OH | H | H | H |
| Cyclopropyl-methyl | OMe | OH | 9'-OH | 8'-F | H | H |
| Cyclopropyl-methyl | OMe | OH | 9'-OH | 7'-Me | H | H |
| Cyclopropyl-methyl | OMe | OH | 9'-OH | 8'-NH2 | H | H |
| Cyclopropyl-methyl | OMe | OH | 7'-OH | H | 6'-Me | 6'-Me |
| Cyclopropyl-methyl | OMe | OH | 7'-OH | 8'-F | 6'-Me | 6'-Me |
| Cyclopropyl-methyl | OMe | OH | 7'-OH | 8'-CO2Et | 6'-Me | 6'-Me |
| Cyclopropyl-methyl | OMe | OH | 8'-OH | H | 6'-Me | 6'-Me |
| Cyclopropyl-methyl | OMe | OH | 8'-OH | 9'-Me | 6'-Me | 6'-Me |
| Cyclopropyl-methyl | OMe | OH | 9'-OH | H | 6'-Me | 6'-Me |
| Cyclopropyl-methyl | OMe | OH | 9'-OH | 9'-NH2 | 6'-Me | 6'-Me |
| Cyclopropyl-methyl | OMe | OH | 7'-OH | H | 5',6'-Benzo | |
| Cyclopropyl-methyl | OMe | OH | 7'-OH | 8'-F | 5',6'-Benzo | |
| Cyclopropyl-methyl | OMe | OH | 7'-OH | 8'-CO2Et | 5',6'-Benzo | |
| Cyclopropyl-methyl | OMe | OH | 8'-OH | H | 5',6'-Benzo | |
| Cyclopropyl-methyl | OMe | OH | 8'-OH | 9'-Me | 5',6'-Benzo | |
| Cyclopropyl-methyl | OMe | OH | 9'-OH | H | 5',6'-Benzo | |
| Cyclopropyl-methyl | OMe | OH | 9'-OH | 9'-NH2 | 5',6'-Benzo | |
| Cyclopropyl-methyl | OMe | OH | H | H | 4'α-OH | H |
| Cyclopropyl-methyl | OMe | OH | H | 8'-F | 4'α-OH | H |

TABLE 11-continued

| R1 | R2 | R3 | R4 | R4' | R5 | R5' |
|---|---|---|---|---|---|---|
| Cyclopropyl-methyl | OMe | OH | 7'-OH | 8'-CO2Et | 4'α-OH | H |
| Cyclopropyl-methyl | OMe | OH | 7'-Me | 9'-NH2 | 4'α-OH | H |
| Cyclopropyl-methyl | OMe | OH | H | H | 4'β-OH | H |
| Cyclopropyl-methyl | OMe | OH | H | 8'-F | 4'β-OH | H |
| Cyclopropyl-methyl | OMe | OH | 7'-OH | 8'-CO2Et | 4'β-OH | H |
| Cyclopropyl-methyl | OMe | OH | 7'-Me | 9'-NH2 | 4'β-OH | H |
| Cyclopropyl-methyl | OMe | OH | H | H | 5'α-OH | H |
| Cyclopropyl-methyl | OMe | OH | H | 8'-F | 5'α-OH | H |
| Cyclopropyl-methyl | OMe | OH | 7'-OH | 8'-CO2Et | 5'α-OH | H |
| Cyclopropyl-methyl | OMe | OH | 7'-Me | 9'-NH2 | 5'α-OH | H |
| Cyclopropyl-methyl | OMe | OH | H | H | 5'β-OH | H |
| Cyclopropyl-methyl | OMe | OH | H | 8'-F | 5'β-OH | H |
| Cyclopropyl-methyl | OMe | OH | 7'-OH | 8'-CO2Et | 5'β-OH | H |
| Cyclopropyl-methyl | OMe | OH | 7'-Me | 9'-NH2 | 5'β-OH | H |
| Cyclopropyl-methyl | OMe | OH | H | H | 6'α-OH | H |
| Cyclopropyl-methyl | OMe | OH | H | 8'-F | 6'α-OH | H |
| Cyclopropyl-methyl | OMe | OH | 7'-OH | 8'-CO2Et | 6'α-OH | H |
| Cyclopropyl-methyl | OMe | OH | 7'-Me | 9'-NH2 | 6'α-OH | H |
| Cyclopropyl-methyl | OMe | OH | H | H | 6'β-OH | H |
| Cyclopropyl-methyl | OMe | OH | H | 8'-F | 6'β-OH | H |
| Cyclopropyl-methyl | OMe | OH | 7'-OH | 8'-CO2Et | 6'β-OH | H |
| Cyclopropyl-methyl | OMe | OH | H | H | 6'α-OH | 6'β-Me |
| Cyclopropyl-methyl | OMe | OH | H | 8'-F | 6'α-OH | 6'β-Me |
| Cyclopropyl-methyl | OMe | OH | 7'-OH | 8'-CO2Et | 6'α-OH | 6'β-Me |
| Cyclopropyl-methyl | OMe | OH | 7'-Me | 9'-NH2 | 6'α-OH | 6'β-Me |
| Cyclopropyl-methyl | OMe | OH | H | H | 6'β-OH | 6'α-Me |

TABLE 12

| R1 | R2 | R3 | R4 | R4' | R5 | R5' |
|---|---|---|---|---|---|---|
| Cyclopropyl-methyl | OMe | OH | H | 8'-F | 6'β-OH | 6'α-Me |
| Cyclopropyl-methyl | OMe | OH | 7'-OH | 8'-CO2Et | 6'β-OH | 6'α-Me |
| Cyclopropyl-methyl | OMe | OH | 7'-Me | 9'-NH2 | 6'β-OH | 6'α-Me |
| Cyclopropyl-methyl | OMe | OH | H | H | 4'-Oxo | |
| Cyclopropyl-methyl | OMe | OH | H | 8'-F | 4'-Oxo | |
| Cyclopropyl-methyl | OMe | OH | 7'-OH | 8'-CO2Et | 4'-Oxo | |
| Cyclopropyl-methyl | OMe | OH | 7'-Me | 9'-NH2 | 4'-Oxo | |
| Cyclopropyl-methyl | OMe | OH | H | H | 5'-Oxo | |
| Cyclopropyl-methyl | OMe | OH | H | 8'-F | 5'-Oxo | |
| Cyclopropyl-methyl | | | | | | |

TABLE 12-continued

| R1 | R2 | R3 | R4 | R4' | R5 | R5' |
|---|---|---|---|---|---|---|
| methyl | | | | | | |
| Cyclopropyl-methyl | OMe | OH | 7'-OH | 8'-CO2Et | 5'-Oxo | |
| Cyclopropyl-methyl | OMe | OH | 7'-Me | 9'-NH2 | 5'-Oxo | |
| Cyclopropyl-methyl | OMe | OH | H | H | 6'-Oxo | |
| Cyclopropyl-methyl | OMe | OH | H | 8'-F | 6'-Oxo | |
| Cyclopropyl-methyl | OMe | OH | 7'-OH | 8'-CO2Et | 6'-Oxo | |
| Cyclopropyl-methyl | OMe | OH | 7'-Me | 9'-NH2 | 6'-Oxo | |
| H | OMe | OH | 7'-OH | H | H | H |
| H | OMe | OH | 7'-OH | 8'-F | H | H |
| H | OMe | OH | 7'-OH | 8'-Me | H | H |
| H | OMe | OH | 7'-OH | 8'-NH2 | H | H |
| H | OMe | OH | 7'-OH | 9'-CO2Et | H | H |
| H | OMe | OH | 8'-OH | H | H | H |
| H | OMe | OH | 8'-OH | 7'-F | H | H |
| H | OMe | OH | 8'-OH | 9'-Me | H | H |
| H | OMe | OH | 8'-OH | 9'-CO2Et | H | H |
| H | OMe | OH | 9'-OH | H | H | H |
| H | OMe | OH | 9'-OH | 8'-F | H | H |
| H | OMe | OH | 9'-OH | 7'-Me | H | H |
| H | OMe | OH | 9'-OH | 8'-NH2 | H | H |
| H | OMe | OH | 7'-OH | H | 6'-Me | 6'-Me |
| H | OMe | OH | 7'-OH | 8'-F | 6'-Me | 6'-Me |
| H | OMe | OH | 7'-OH | 8'-CO2Et | 6'-Me | 6'-Me |
| H | OMe | OH | 8'-OH | H | 6'-Me | 6'-Me |
| H | OMe | OH | 8'-OH | 9'-Me | 6'-Me | 6'-Me |
| H | OMe | OH | 9'-OH | H | 6'-Me | 6'-Me |
| H | OMe | OH | 9'-OH | 9'-NH2 | 6'-Me | 6'-Me |
| H | OMe | OH | 7'-OH | H | 5',6'-Benzo | |
| H | OMe | OH | 7'-OH | 8'-F | 5',6'-Benzo | |
| H | OMe | OH | 7'-OH | 8'-CO2Et | 5',6'-Benzo | |
| H | OMe | OH | 8'-OH | H | 5',6'-Benzo | |
| H | OMe | OH | 8'-OH | 9'-Me | 5',6'-Benzo | |
| H | OMe | OH | 9'-OH | H | 5',6'-Benzo | |
| H | OMe | OH | 9'-OH | 9'-NH2 | 5',6'-Benzo | |
| H | OMe | OH | H | H | 4'α-OH | H |
| H | OMe | OH | H | 8'-F | 4'α-OH | H |
| H | OMe | OH | 7'-OH | 8'-CO2Et | 4'α-OH | H |
| H | OMe | OH | 7'-Me | 9'-NH2 | 4'α-OH | H |
| H | OMe | OH | H | H | 4'β-OH | H |
| H | OMe | OH | H | 8'-F | 4'β-OH | H |
| H | OMe | OH | 7'-OH | 8'-CO2Et | 4'β-OH | H |
| H | OMe | OH | 7'-Me | 9'-NH2 | 4'β-OH | H |
| H | OMe | OH | H | H | 5'α-OH | H |

TABLE 13

| R1 | R2 | R3 | R4 | R4' | R5 | R5' |
|---|---|---|---|---|---|---|
| H | OMe | OH | H | 8'-F | 5'α-OH | H |
| H | OMe | OH | 7'-OH | 8'-CO2Et | 5'α-OH | H |
| H | OMe | OH | 7'-Me | 9'-NH2 | 5'α-OH | H |
| H | OMe | OH | H | H | 5'β-OH | H |
| H | OMe | OH | H | 8'-F | 5'β-OH | H |
| H | OMe | OH | 7'-OH | 8'-CO2Et | 5'β-OH | H |
| H | OMe | OH | 7'-Me | 9'-NH2 | 5'β-OH | H |
| H | OMe | OH | H | H | 6'α-OH | H |
| H | OMe | OH | H | 8'-F | 6'α-OH | H |
| H | OMe | OH | 7'-OH | 8'-CO2Et | 6'α-OH | H |
| H | OMe | OH | 7'-Me | 9'-NH2 | 6'α-OH | H |
| H | OMe | OH | H | H | 6'β-OH | H |
| H | OMe | OH | H | 8'-F | 6'β-OH | H |
| H | OMe | OH | 7'-OH | 8'-CO2Et | 6'β-OH | H |
| H | OMe | OH | H | H | 6'α-OH | 6'β-Me |
| H | OMe | OH | H | 8'-F | 6'α-OH | 6'β-Me |
| H | OMe | OH | 7'-OH | 8'-CO2Et | 6'α-OH | 6'β-Me |
| H | OMe | OH | 7'-Me | 9'-NH2 | 6'α-OH | 6'β-Me |
| H | OMe | OH | H | H | 6'β-OH | 6'α-Me |
| H | OMe | OH | H | 8'-F | 6'β-OH | 6'α-Me |
| H | OMe | OH | 7'-OH | 8'-CO2Et | 6'β-OH | 6'α-Me |
| H | OMe | OH | 7'-Me | 9'-NH2 | 6'β-OH | 6'α-Me |
| H | OMe | OH | H | H | 4'-Oxo | |
| H | OMe | OH | H | 8'-F | 4'-Oxo | |
| H | OMe | OH | 7'-OH | 8'-CO2Et | 4'-Oxo | |
| H | OMe | OH | 7'-Me | 9'-NH2 | 4'-Oxo | |
| H | OMe | OH | H | H | 5'-Oxo | |
| H | OMe | OH | H | 8'-F | 5'-Oxo | |
| H | OMe | OH | 7'-OH | 8'-CO2Et | 5'-Oxo | |
| H | OMe | OH | 7'-Me | 9'-NH2 | 5'-Oxo | |
| H | OMe | OH | H | H | 6'-Oxo | |
| H | OMe | OH | H | 8'-F | 6'-Oxo | |
| H | OMe | OH | 7'-OH | 8'-CO2Et | 6'-Oxo | |
| H | OMe | OH | 7'-Me | 9'-NH2 | 6'-Oxo | |
| CH2CH2Ph | OMe | OH | 7'-OH | H | H | H |
| CH2CH2Ph | OMe | OH | 7'-OH | 8'-F | H | H |
| CH2CH2Ph | OMe | OH | 7'-OH | 8'-Me | H | H |
| CH2CH2Ph | OMe | OH | 7'-OH | 8'-NH2 | H | H |
| CH2CH2Ph | OMe | OH | 7'-OH | 9'-CO2Et | H | H |
| CH2CH2Ph | OMe | OH | 8'-OH | H | H | H |
| CH2CH2Ph | OMe | OH | 8'-OH | 7'-F | H | H |
| CH2CH2Ph | OMe | OH | 8'-OH | 9'-Me | H | H |
| CH2CH2Ph | OMe | OH | 8'-OH | 9'-CO2Et | H | H |
| CH2CH2Ph | OMe | OH | 9'-OH | H | H | H |
| CH2CH2Ph | OMe | OH | 9'-OH | 8'-F | H | H |
| CH2CH2Ph | OMe | OH | 9'-OH | 7'-Me | H | H |
| CH2CH2Ph | OMe | OH | 9'-OH | 8'-NH2 | H | H |
| CH2CH2Ph | OMe | OH | 7'-OH | H | 6'-Me | 6'-Me |
| CH2CH2Ph | OMe | OH | 7'-OH | 8'-F | 6'-Me | 6'-Me |
| CH2CH2Ph | OMe | OH | 7'-OH | 8'-CO2Et | 6'-Me | 6'-Me |
| CH2CH2Ph | OMe | OH | 8'-OH | H | 6'-Me | 6'-Me |

TABLE 14

| R1 | R2 | R3 | R4 | R4' | R5 | R5' |
|---|---|---|---|---|---|---|
| CH2CH2Ph | OMe | OH | 8'-OH | 9'-Me | 6'-Me | 6'-Me |
| CH2CH2Ph | OMe | OH | 9'-OH | H | 6'-Me | 6'-Me |
| CH2CH2Ph | OMe | OH | 9'-OH | 9'-NH2 | 6'-Me | 6'-Me |
| CH2CH2Ph | OMe | OH | 7'-OH | H | 5',6'-Benzo | |
| CH2CH2Ph | OMe | OH | 7'-OH | 8'-F | 5',6'-Benzo | |
| CH2CH2Ph | OMe | OH | 7'-OH | 8'-CO2Et | 5',6'-Benzo | |
| CH2CH2Ph | OMe | OH | 8'-OH | H | 5',6'-Benzo | |
| CH2CH2Ph | OMe | OH | 8'-OH | 9'-Me | 5',6'-Benzo | |
| CH2CH2Ph | OMe | OH | 9'-OH | H | 5',6'-Benzo | |
| CH2CH2Ph | OMe | OH | 9'-OH | 9'-NH2 | 5',6'-Benzo | |
| CH2CH2Ph | OMe | OH | H | H | 4'α-OH | H |
| CH2CH2Ph | OMe | OH | H | 8'-F | 4'α-OH | H |
| CH2CH2Ph | OMe | OH | 7'-OH | 8'-CO2Et | 4'α-OH | H |
| CH2CH2Ph | OMe | OH | 7'-Me | 9'-NH2 | 4'α-OH | H |
| CH2CH2Ph | OMe | OH | H | H | 4'β-OH | H |
| CH2CH2Ph | OMe | OH | H | 8'-F | 4'β-OH | H |
| CH2CH2Ph | OMe | OH | 7'-OH | 8'-CO2Et | 4'β-OH | H |
| CH2CH2Ph | OMe | OH | 7'-Me | 9'-NH2 | 4'β-OH | H |
| CH2CH2Ph | OMe | OH | H | H | 5'α-OH | H |
| CH2CH2Ph | OMe | OH | H | 8'-F | 5'α-OH | H |
| CH2CH2Ph | OMe | OH | 7'-OH | 8'-CO2Et | 5'α-OH | H |
| CH2CH2Ph | OMe | OH | 7'-Me | 9'-NH2 | 5'α-OH | H |
| CH2CH2Ph | OMe | OH | H | H | 5'β-OH | H |
| CH2CH2Ph | OMe | OH | H | 8'-F | 5'β-OH | H |
| CH2CH2Ph | OMe | OH | 7'-OH | 8'-CO2Et | 5'β-OH | H |
| CH2CH2Ph | OMe | OH | 7'-Me | 9'-NH2 | 5'β-OH | H |
| CH2CH2Ph | OMe | OH | H | H | 6'α-OH | H |
| CH2CH2Ph | OMe | OH | H | 8'-F | 6'α-OH | H |
| CH2CH2Ph | OMe | OH | 7'-OH | 8'-CO2Et | 6'α-OH | H |
| CH2CH2Ph | OMe | OH | 7'-Me | 9'-NH2 | 6'α-OH | H |
| CH2CH2Ph | OMe | OH | H | H | 6'β-OH | H |
| CH2CH2Ph | OMe | OH | H | 8'-F | 6'β-OH | H |
| CH2CH2Ph | OMe | OH | 7'-OH | 8'-CO2Et | 6'β-OH | H |
| CH2CH2Ph | OMe | OH | H | H | 6'α-OH | 6'β-Me |
| CH2CH2Ph | OMe | OH | H | 8'-F | 6'α-OH | 6'β-Me |
| CH2CH2Ph | OMe | OH | 7'-OH | 8'-CO2Et | 6'α-OH | 6'β-Me |
| CH2CH2Ph | OMe | OH | 7'-Me | 9'-NH2 | 6'α-OH | 6'β-Me |
| CH2CH2Ph | OMe | OH | H | H | 6'β-OH | 6'α-Me |

TABLE 14-continued

| R1 | R2 | R3 | R4 | R4' | R5 | R5' |
|---|---|---|---|---|---|---|
| CH2CH2Ph | OMe | OH | H | 8'-F | 6'β-OH | 6'α-Me |
| CH2CH2Ph | OMe | OH | 7'-OH | 8'-CO2Et | 6'β-OH | 6'α-Me |
| CH2CH2Ph | OMe | OH | 7'-Me | 9'-NH2 | 6'β-OH | 6'α-Me |
| CH2CH2Ph | OMe | OH | H | H | 4'-Oxo | |
| CH2CH2Ph | OMe | OH | H | 8'-F | 4'-Oxo | |
| CH2CH2Ph | OMe | OH | 7'-OH | 8'-CO2Et | 4'-Oxo | |
| CH2CH2Ph | OMe | OH | 7'-Me | 9'-NH2 | 4'-Oxo | |
| CH2CH2Ph | OMe | OH | H | H | 5'-Oxo | |
| CH2CH2Ph | OMe | OH | H | 8'-F | 5'-Oxo | |
| CH2CH2Ph | OMe | OH | 7'-OH | 8'-CO2Et | 5'-Oxo | |
| CH2CH2Ph | OMe | OH | 7'-Me | 9'-NH2 | 5'-Oxo | |
| CH2CH2Ph | OMe | OH | H | H | 6'-Oxo | |
| CH2CH2Ph | OMe | OH | H | 8'-F | 6'-Oxo | |

TABLE 15

| R1 | R2 | R3 | R4 | R4' | R5 | R5' |
|---|---|---|---|---|---|---|
| CH2CH2Ph | OMe | OH | 7'-OH | 8'-NH2 | 6'-Oxo | |
| CH2CH2Ph | OMe | OH | 7'-Me | 9'-NH2 | 6'-Oxo | |
| Allyl | OMe | OH | 7'-OH | H | H | H |
| Allyl | OMe | OH | 7'-OH | 8'-F | H | H |
| Allyl | OMe | OH | 7'-OH | 8'-Me | H | H |
| Allyl | OMe | OH | 7'-OH | 8'-CO2Et | H | H |
| Allyl | OMe | OH | 8'-OH | H | H | H |
| Allyl | OMe | OH | 8'-OH | 9'-Me | H | H |
| Allyl | OMe | OH | 8'-OH | 9'-NH2 | H | H |
| Allyl | OMe | OH | 9'-OH | H | H | H |
| Allyl | OMe | OH | 9'-OH | 8'-F | H | H |
| Allyl | OMe | OH | 7'-OH | H | 6'-Me | 6'-Me |
| Allyl | OMe | OH | 7'-OH | 8'-F | 6'-Me | 6'-Me |
| Allyl | OMe | OH | 7'-OH | 8'-CO2Et | 6'-Me | 6'-Me |
| Allyl | OMe | OH | 8'-OH | H | 6'-Me | 6'-Me |
| Allyl | OMe | OH | 8'-OH | 9'-Me | 6'-Me | 6'-Me |
| Allyl | OMe | OH | 9'-OH | H | 6'-Me | 6'-Me |
| Allyl | OMe | OH | 9'-OH | 9'-NH2 | 6'-Me | 6'-Me |
| Allyl | OMe | OH | 7'-OH | H | 5',6'-Benzo | |
| Allyl | OMe | OH | 7'-OH | 8'-F | 5',6'-Benzo | |
| Allyl | OMe | OH | 7'-OH | 8'-CO2Et | 5',6'-Benzo | |
| Allyl | OMe | OH | 8'-OH | H | 5',6'-Benzo | |
| Allyl | OMe | OH | 8'-OH | 9'-Me | 5',6'-Benzo | |
| Allyl | OMe | OH | 9'-OH | H | 5',6'-Benzo | |
| Allyl | OMe | OH | 9'-OH | 9'-NH2 | 5',6'-Benzo | |
| Allyl | OMe | OH | H | H | 4'α-OH | H |
| Allyl | OMe | OH | H | 8'-F | 4'α-OH | H |
| Allyl | OMe | OH | 7'-OH | 8'-CO2Et | 4'α-OH | H |
| Allyl | OMe | OH | 7'-Me | 9'-NH2 | 4'α-OH | H |
| Allyl | OMe | OH | H | H | 4'β-OH | H |
| Allyl | OMe | OH | H | 8'-F | 4'β-OH | H |
| Allyl | OMe | OH | 7'-OH | 8'-CO2Et | 4'β-OH | H |
| Allyl | OMe | OH | 7'-Me | 9'-NH2 | 4'β-OH | H |
| Allyl | OMe | OH | H | H | 5'α-OH | H |
| Allyl | OMe | OH | H | 8'-F | 5'α-OH | H |
| Allyl | OMe | OH | H | H | 5'β-OH | H |
| Allyl | OMe | OH | H | 8'-F | 5'β-OH | H |
| Allyl | OMe | OH | H | H | 6'α-OH | H |
| Allyl | OMe | OH | H | 8'-F | 6'α-OH | H |
| Allyl | OMe | OH | H | H | 6'β-OH | H |
| Allyl | OMe | OH | H | 8'-F | 6'β-OH | H |
| Allyl | OMe | OH | H | H | 6'α-OH | 6'β-Me |
| Allyl | OMe | OH | H | 8'-F | 6'α-OH | 6'β-Me |
| Allyl | OMe | OH | 7'-OH | 8'-CO2Et | 6'α-OH | 6'β-Me |
| Allyl | OMe | OH | 7'-Me | 9'-NH2 | 6'α-OH | 6'β-Me |
| Allyl | OMe | OH | H | H | 6'β-OH | 6'α-Me |
| Allyl | OMe | OH | H | 8'-F | 6'β-OH | 6'α-Me |
| Allyl | OMe | OH | 7'-OH | 8'-CO2Et | 6'β-OH | 6'α-Me |
| Allyl | OMe | OH | 7'-Me | 9'-NH2 | 6'β-OH | 6'α-Me |
| Allyl | OMe | OH | H | H | 4'-Oxo | |
| Allyl | OMe | OH | H | 8'-F | 4'-Oxo | |

TABLE 16

| R1 | R2 | R3 | R4 | R4' | R5 | R5' |
|---|---|---|---|---|---|---|
| Allyl | OMe | OH | H | 8'-F | 5'-Oxo | |
| Allyl | OMe | OH | H | H | 6'-Oxo | |
| Allyl | OMe | OH | H | 8'-F | 6'-Oxo | |
| 2-Thienylethyl | OMe | OH | 7'-OH | H | H | H |
| 2-Thienylethyl | OMe | OH | 7'-OH | 8'-F | H | H |
| 2-Thienylethyl | OMe | OH | 7'-OH | 8'-Me | H | H |
| 2-Thienylethyl | OMe | OH | 7'-OH | 8'-CO2Et | H | H |
| 2-Thienylethyl | OMe | OH | 8'-OH | H | H | H |
| 2-Thienylethyl | OMe | OH | 8'-OH | 9'-Me | H | H |
| 2-Thienylethyl | OMe | OH | 8'-OH | 9'-NH2 | H | H |
| 2-Thienylethyl | OMe | OH | 9'-OH | H | H | H |
| 2-Thienylethyl | OMe | OH | 9'-OH | 8'-F | H | H |
| 2-Thienylethyl | OMe | OH | 7'-OH | H | 6'-Me | 6'-Me |
| 2-Thienylethyl | OMe | OH | 7'-OH | 8'-F | 6'-Me | 6'-Me |
| 2-Thienylethyl | OMe | OH | 7'-OH | 8'-CO2Et | 6'-Me | 6'-Me |
| 2-Thienylethyl | OMe | OH | 8'-OH | H | 6'-Me | 6'-Me |
| 2-Thienylethyl | OMe | OH | 8'-OH | 9'-Me | 6'-Me | 6'-Me |
| 2-Thienylethyl | OMe | OH | 9'-OH | H | 6'-Me | 6'-Me |
| 2-Thienylethyl | OMe | OH | 9'-OH | 9'-NH2 | 6'-Me | 6'-Me |
| 2-Thienylethyl | OMe | OH | 7'-OH | H | 5',6'-Benzo | |
| 2-Thienylethyl | OMe | OH | 7'-OH | 8'-F | 5',6'-Benzo | |
| 2-Thienylethyl | OMe | OH | 7'-OH | 8'-CO2Et | 5',6'-Benzo | |
| 2-Thienylethyl | OMe | OH | 8'-OH | H | 5',6'-Benzo | |
| 2-Thienylethyl | OMe | OH | 8'-OH | 9'-Me | 5',6'-Benzo | |
| 2-Thienylethyl | OMe | OH | 9'-OH | H | 5',6'-Benzo | |
| 2-Thienylethyl | OMe | OH | 9'-OH | 9'-NH2 | 5',6'-Benzo | |
| 2-Thienylethyl | OMe | OH | H | H | 4'α-OH | H |
| 2-Thienylethyl | OMe | OH | H | 8'-F | 4'α-OH | H |
| 2-Thienylethyl | OMe | OH | 7'-OH | 8'-CO2Et | 4'α-OH | H |
| 2-Thienylethyl | OMe | OH | 7'-Me | 9'-NH2 | 4'α-OH | H |
| 2-Thienylethyl | OMe | OH | H | H | 4'β-OH | H |
| 2-Thienylethyl | OMe | OH | H | 8'-F | 4'β-OH | H |
| 2-Thienylethyl | OMe | OH | 7'-OH | 8'-CO2Et | 4'β-OH | H |
| 2-Thienylethyl | OMe | OH | 7'-Me | 9'-NH2 | 4'β-OH | H |
| 2-Thienylethyl | OMe | OH | H | H | 5'α-OH | H |
| 2-Thienylethyl | OMe | OH | H | 8'-F | 5'α-OH | H |
| 2-Thienylethyl | OMe | OH | H | H | 5'β-OH | H |
| 2-Thienylethyl | OMe | OH | H | 8'-F | 5'β-OH | H |
| 2-Thienylethyl | OMe | OH | H | H | 6'α-OH | H |
| 2-Thienylethyl | OMe | OH | H | 8'-F | 6'α-OH | H |
| 2-Thienylethyl | OMe | OH | H | H | 6'β-OH | H |
| 2-Thienylethyl | OMe | OH | H | 8'-F | 6'β-OH | H |
| 2-Thienylethyl | OMe | OH | H | H | 6'α-OH | 6'β-Me |
| 2-Thienylethyl | OMe | OH | H | 8'-F | 6'α-OH | 6'β-Me |
| 2-Thienylethyl | OMe | OH | 7'-OH | 8'-CO2Et | 6'α-OH | 6'β-Me |
| 2-Thienylethyl | OMe | OH | 7'-Me | 9'-NH2 | 6'α-OH | 6'β-Me |
| 2-Thienylethyl | OMe | OH | H | H | 6'β-OH | 6'α-Me |
| 2-Thienylethyl | OMe | OH | H | 8'-F | 6'β-OH | 6'α-Me |
| 2-Thienylethyl | OMe | OH | 7'-OH | 8'-CO2Et | 6'β-OH | 6'α-Me |
| 2-Thienylethyl | OMe | OH | 7'-Me | 9'-NH2 | 6'β-OH | 6'α-Me |
| 2-Thienylethyl | OMe | OH | H | H | 4'-Oxo | |

TABLE 17

| R1 | R2 | R3 | R4 | R4' | R5 | R5' |
|---|---|---|---|---|---|---|
| 2-Thienylethyl | OMe | OH | H | 8'-F | 4'-Oxo | |
| 2-Thienylethyl | OMe | OH | H | 8'-F | 5'-Oxo | |
| 2-Thienylethyl | OMe | OH | H | H | 6'-Oxo | |
| 2-Thienylethyl | OMe | OH | H | 8'-F | 6'-Oxo | |

2-Thienylethyl as shown in Tables 8, 9, 16, and 17 indicates 2-(2-thienyl)ethyl.

The compound of the present invention also includes a compound represented by general formula (IB):

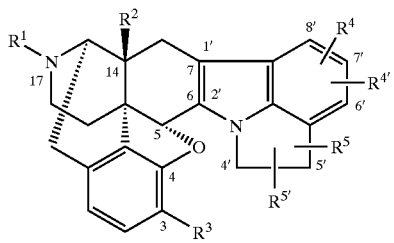

(IB)

wherein $R^1, R^2, R^3, R^4, R^{4'}, R^5$, and $R^{5'}$ are as defined above.

Specific examples of compounds represented by general formula (IB) are shown in Tables 18 to 21.

TABLE 18

| R1 | R2 | R3 | R4 | R4' | R5 | R5' |
|---|---|---|---|---|---|---|
| Me | OH | OH | 6'-OH | H | H | H |
| Me | OH | OH | 6'-OH | 7'-F | H | H |
| Me | OH | OH | 6'-OH | 7'-Me | H | H |
| Me | OH | OH | 6'-OH | 7'-CO2Et | H | H |
| Me | OH | OH | 7'-OH | H | H | H |
| Me | OH | OH | 7'-OH | 8'-Me | H | H |
| Me | OH | OH | 7'-OH | 8'-NH2 | H | H |
| Me | OH | OH | 8'-OH | H | H | H |
| Me | OH | OH | 8'-OH | 7'-F | H | H |
| Me | OH | OH | H | H | 4'α-OH | H |
| Me | OH | OH | H | 7'-F | 4'α-OH | H |
| Me | OH | OH | 6'-OH | 7'-CO2Et | 4'α-OH | H |
| Me | OH | OH | 6'-Me | 8'-NH2 | 4'α-OH | H |
| Me | OH | OH | H | H | 4'β-OH | H |
| Me | OH | OH | H | 7'-F | 4'β-OH | H |
| Me | OH | OH | 6'-OH | 7'-CO2Et | 4'β-OH | H |
| Me | OH | OH | 6'-Me | 8'-NH2 | 4'β-OH | H |
| Me | OH | OH | H | H | 5'α-OH | H |
| Me | OH | OH | H | 7'-F | 5'α-OH | H |
| Me | OH | OH | 6'-OH | 7'-CO2Et | 5'α-OH | H |
| Me | OH | OH | 6'-Me | 8'-NH2 | 5'α-OH | H |
| Me | OH | OH | H | H | 5'β-OH | H |
| Me | OH | OH | H | 7'-F | 5'β-OH | H |
| Me | OH | OH | 6'-OH | 7'-CO2Et | 5'β-OH | H |
| Me | OH | OH | 6'-Me | 8'-NH2 | 5'β-OH | H |
| Me | OH | OH | H | H | 5'α-OH | 5'β-Me |
| Me | OH | OH | H | 7'-F | 5'α-OH | 5'β-Me |
| Me | OH | OH | 6'-OH | 7'-CO2Et | 5'α-OH | 5'β-Me |
| Me | OH | OH | 6'-Me | 8'-NH2 | 5'α-OH | 5'β-Me |
| Me | OH | OH | H | H | 5'β-OH | 5'α-Me |
| Me | OH | OH | H | 7'-F | 5'β-OH | 5'α-Me |
| Me | OH | OH | 6'-OH | 7'-CO2Et | 5'β-OH | 5'α-Me |
| Me | OH | OH | 6'-Me | 8'-NH2 | 5'β-OH | 5'α-Me |
| Me | OH | OH | H | H | 4'-Oxo | |
| Me | OH | OH | H | 7'-F | 4'-Oxo | |
| Me | OH | OH | H | H | 5'-Oxo | |
| Me | OH | OH | H | 7'-F | 5'-Oxo | |
| Cyclopropyl-methyl | OH | OH | 6'-OH | H | H | H |
| Cyclopropyl-methyl | OH | OH | 6'-OH | 7'-F | H | H |
| Cyclopropyl-methyl | OH | OH | 6'-OH | 7'-Me | H | H |
| Cyclopropyl-methyl | OH | OH | 6'-OH | 7'-CO2Et | H | H |
| Cyclopropyl-methyl | OH | OH | 7'-OH | H | H | H |
| Cyclopropyl-methyl | OH | OH | 7'-OH | 8'-Me | H | H |
| Cyclopropyl-methyl | OH | OH | 7'-OH | 8'-NH2 | H | H |
| Cyclopropyl-methyl | OH | OH | 8'-OH | H | H | H |
| Cyclopropyl-methyl | OH | OH | 8'-OH | 7'-F | H | H |
| Cyclopropyl-methyl | OH | OH | H | H | 4'α-OH | H |

TABLE 18-continued

| R1 | R2 | R3 | R4 | R4' | R5 | R5' |
|---|---|---|---|---|---|---|
| Cyclopropyl-methyl | OH | OH | H | 7'-F | 4'α-OH | H |
| Cyclopropyl-methyl | OH | OH | 6'-OH | 7'-CO2Et | 4'α-OH | H |
| Cyclopropyl-methyl | OH | OH | 6'-Me | 8'-NH2 | 4'α-OH | H |
| Cyclopropyl-methyl | OH | OH | H | H | 4'β-OH | H |

TABLE 19

| R1 | R2 | R3 | R4 | R4' | R5 | R5' |
|---|---|---|---|---|---|---|
| Cyclopropyl-methyl | OH | OH | H | 7'-F | 4'β-OH | H |
| Cyclopropyl-methyl | OH | OH | 6'-OH | 7'-CO2Et | 4'β-OH | H |
| Cyclopropyl-methyl | OH | OH | 6'-Me | 8'-NH2 | 4'β-OH | H |
| Cyclopropyl-methyl | OH | OH | H | H | 5'α-OH | H |
| Cyclopropyl-methyl | OH | OH | H | 7'-F | 5'α-OH | H |
| Cyclopropyl-methyl | OH | OH | 6'-OH | 7'-CO2Et | 5'α-OH | H |
| Cyclopropyl-methyl | OH | OH | 6'-Me | 8'-NH2 | 5'α-OH | H |
| Cyclopropyl-methyl | OH | OH | H | H | 5'β-OH | H |
| Cyclopropyl-methyl | OH | OH | H | 7'-F | 5'β-OH | H |
| Cyclopropyl-methyl | OH | OH | 6'-OH | 7'-CO2Et | 5'β-OH | H |
| Cyclopropyl-methyl | OH | OH | 6'-Me | 8'-NH2 | 5'β-OH | H |
| Cyclopropyl-methyl | OH | OH | H | H | 5'α-OH | 5'β-Me |
| Cyclopropyl-methyl | OH | OH | H | 7'-F | 5'α-OH | 5'β-Me |
| Cyclopropyl-methyl | OH | OH | 6'-OH | 7'-CO2Et | 5'α-OH | 5'β-Me |
| Cyclopropyl-methyl | OH | OH | 6'-Me | 8'-NH2 | 5'α-OH | 5'β-Me |
| Cyclopropyl-methyl | OH | OH | H | H | 5'β-OH | 5'α-Me |
| Cyclopropyl-methyl | OH | OH | H | 7'-F | 5'β-OH | 5'α-Me |
| Cyclopropyl-methyl | OH | OH | 6'-OH | 7'-CO2Et | 5'β-OH | 5'α-Me |
| Cyclopropyl-methyl | OH | OH | 6'-Me | 8'-NH2 | 5'β-OH | 5'α-Me |
| Cyclopropyl-methyl | OH | OH | H | H | 4'-Oxo | |
| Cyclopropyl-methyl | OH | OH | H | 7'-F | 4'-Oxo | |
| Cyclopropyl-methyl | OH | OH | H | H | 5'-Oxo | |
| Cyclopropyl-methyl | OH | OH | H | 7'-F | 5'-Oxo | |
| CH2CH2Ph | OH | OH | 6'-OH | H | H | H |
| CH2CH2Ph | OH | OH | 6'-OH | 7'-F | H | H |
| CH2CH2Ph | OH | OH | 6'-OH | 7'-Me | H | H |
| CH2CH2Ph | OH | OH | 6'-OH | 7'-CO2Et | H | H |
| CH2CH2Ph | OH | OH | 7'-OH | H | H | H |
| CH2CH2Ph | OH | OH | 7'-OH | 8'-Me | H | H |
| CH2CH2Ph | OH | OH | 7'-OH | 8'-NH2 | H | H |
| CH2CH2Ph | OH | OH | 8'-OH | H | H | H |
| CH2CH2Ph | OH | OH | 8'-OH | 7'-F | H | H |
| CH2CH2Ph | OH | OH | H | H | 4'α-OH | H |
| CH2CH2Ph | OH | OH | H | 7'-F | 4'α-OH | H |
| CH2CH2Ph | OH | OH | 6'-OH | 7'-CO2Et | 4'α-OH | H |
| CH2CH2Ph | OH | OH | 6'-Me | 8'-NH2 | 4'α-OH | H |
| CH2CH2Ph | OH | OH | H | H | 4'β-OH | H |
| CH2CH2Ph | OH | OH | H | 7'-F | 4'β-OH | H |

TABLE 19-continued

| R1 | R2 | R3 | R4 | R4' | R5 | R5' |
|---|---|---|---|---|---|---|
| CH2CH2Ph | OH | OH | 6'-OH | 7'-CO2Et | 4'β-OH | H |
| CH2CH2Ph | OH | OH | 6'-Me | 8'-NH2 | 4'β-OH | H |
| CH2CH2Ph | OH | OH | H | H | 5'α-OH | H |
| CH2CH2Ph | OH | OH | H | 7'-F | 5'α-OH | H |
| CH2CH2Ph | OH | OH | 6'-OH | 7'-CO2Et | 5'α-OH | H |
| CH2CH2Ph | OH | OH | 6'-Me | 8'-NH2 | 5'α-OH | H |
| CH2CH2Ph | OH | OH | H | H | 5'β-OH | H |
| CH2CH2Ph | OH | OH | H | 7'-F | 5'β-OH | H |
| CH2CH2Ph | OH | OH | 6'-OH | 7'-CO2Et | 5'β-OH | H |
| CH2CH2Ph | OH | OH | 6'-Me | 8'-NH2 | 5'β-OH | H |
| CH2CH2Ph | OH | OH | H | H | 5'α-OH | 5'β-Me |
| CH2CH2Ph | OH | OH | H | 7'-F | 5'α-OH | 5'β-Me |
| CH2CH2Ph | OH | OH | 6'-OH | 7'-CO2Et | 5'α-OH | 5'β-Me |

TABLE 20

| R1 | R2 | R3 | R4 | R4' | R5 | R5' |
|---|---|---|---|---|---|---|
| CH2CH2Ph | OH | OH | 6'-Me | 8'-NH2 | 5'α-OH | 5'β-Me |
| CH2CH2Ph | OH | OH | H | H | 5'β-OH | 5'α-Me |
| CH2CH2Ph | OH | OH | H | 7'-F | 5'β-OH | 5'α-Me |
| CH2CH2Ph | OH | OH | 6'-OH | 7'-CO2Et | 5'β-OH | 5'α-Me |
| CH2CH2Ph | OH | OH | 6'-Me | 8'-NH2 | 5'β-OH | 5'α-Me |
| CH2CH2Ph | OH | OH | H | H | 4'-Oxo | |
| CH2CH2Ph | OH | OH | H | 7'-F | 4'-Oxo | |
| CH2CH2Ph | OH | OH | H | H | 5'-Oxo | |
| CH2CH2Ph | OH | OH | H | 7'-F | 5'-Oxo | |
| Me | OMe | OH | 6'-OH | H | H | H |
| Me | OMe | OH | 6'-OH | 7'-F | H | H |
| Me | OMe | OH | 6'-OH | 7'-Me | H | H |
| Me | OMe | OH | 6'-OH | 7'-CO2Et | H | H |
| Me | OMe | OH | 7'-OH | H | H | H |
| Me | OMe | OH | 7'-OH | 8'-Me | H | H |
| Me | OMe | OH | 7'-OH | 8'-NH2 | H | H |
| Me | OMe | OH | 8'-OH | H | H | H |
| Me | OMe | OH | 8'-OH | 7'-F | H | H |
| Me | OMe | OH | H | H | 4'α-OH | H |
| Me | OMe | OH | H | 7'-F | 4'α-OH | H |
| Me | OMe | OH | 6'-OH | 7'-CO2Et | 4'α-OH | H |
| Me | OMe | OH | 6'-Me | 8'-NH2 | 4'α-OH | H |
| Me | OMe | OH | H | H | 4'β-OH | H |
| Me | OMe | OH | H | 7'-F | 4'β-OH | H |
| Me | OMe | OH | 6'-OH | 7'-CO2Et | 4'β-OH | H |
| Me | OMe | OH | 6'-Me | 8'-NH2 | 4'β-OH | H |
| Me | OMe | OH | H | H | 5'α-OH | H |
| Me | OMe | OH | H | 7'-F | 5'α-OH | H |
| Me | OMe | OH | 6'-OH | 7'-CO2Et | 5'α-OH | H |
| Me | OMe | OH | 6'-Me | 8'-NH2 | 5'α-OH | H |
| Me | OMe | OH | H | H | 5'β-OH | H |
| Me | OMe | OH | H | 7'-F | 5'β-OH | H |
| Me | OMe | OH | 6'-OH | 7'-CO2Et | 5'β-OH | H |
| Me | OMe | OH | 6'-Me | 8'-NH2 | 5'β-OH | H |
| Me | OMe | OH | H | H | 5'α-OH | 5'β-Me |
| Me | OMe | OH | H | 7'-F | 5'α-OH | 5'β-Me |
| Me | OMe | OH | 6'-OH | 7'-CO2Et | 5'α-OH | 5'β-Me |
| Me | OMe | OH | 6'-Me | 8'-NH2 | 5'α-OH | 5'β-Me |
| Me | OMe | OH | H | H | 5'β-OH | 5'α-Me |
| Me | OMe | OH | H | 7'-F | 5'β-OH | 5'α-Me |
| Me | OMe | OH | 6'-OH | 7'-CO2Et | 5'β-OH | 5'α-Me |
| Me | OMe | OH | 6'-Me | 8'-NH2 | 5'β-OH | 5'α-Me |
| Me | OMe | OH | H | H | 4'-Oxo | |
| Me | OMe | OH | H | 7'-F | 4'-Oxo | |
| Me | OMe | OH | H | H | 5'-Oxo | |
| Me | OMe | OH | H | 7'-F | 5'-Oxo | |
| Cyclopropyl-methyl | OMe | OH | 6'-OH | H | H | H |
| Cyclopropyl-methyl | OMe | OH | 6'-OH | 7'-F | H | H |
| Cyclopropyl-methyl | OMe | OH | 6'-OH | 7'-Me | H | H |
| Cyclopropyl-methyl | OMe | OH | 6'-OH | 7'-CO2Et | H | H |
| Cyclopropyl-methyl | OMe | OH | 7'-OH | H | H | H |

TABLE 21

| R1 | R2 | R3 | R4 | R4' | R5 | R5' |
|---|---|---|---|---|---|---|
| Cyclopropyl-methyl | OMe | OH | 7'-OH | 8'-Me | H | H |
| Cyclopropyl-methyl | OMe | OH | 7'-OH | 8'-NH2 | H | H |
| Cyclopropyl-methyl | OMe | OH | 8'-OH | H | H | H |
| Cyclopropyl-methyl | OMe | OH | 8'-OH | 7'-F | H | H |
| Cyclopropyl-methyl | OMe | OH | H | H | 4'α-OH | H |
| Cyclopropyl-methyl | OMe | OH | H | 7'-F | 4'α-OH | H |
| Cyclopropyl-methyl | OMe | OH | 6'-OH | 7'-CO2Et | 4'α-OH | H |
| Cyclopropyl-methyl | OMe | OH | 6'-Me | 8'-NH2 | 4'α-OH | H |
| Cyclopropyl-methyl | OMe | OH | H | H | 4'β-OH | H |
| Cyclopropyl-methyl | OMe | OH | H | 7'-F | 4'β-OH | H |
| Cyclopropyl-methyl | OMe | OH | 6'-OH | 7'-CO2Et | 4'β-OH | H |
| Cyclopropyl-methyl | OMe | OH | 6'-Me | 8'-NH2 | 4'β-OH | H |
| Cyclopropyl-methyl | OMe | OH | H | H | 5'α-OH | H |
| Cyclopropyl-methyl | OMe | OH | H | 7'-F | 5'α-OH | H |
| Cyclopropyl-methyl | OMe | OH | 6'-OH | 7'-CO2Et | 5'α-OH | H |
| Cyclopropyl-methyl | OMe | OH | 6'-Me | 8'-NH2 | 5'α-OH | H |
| Cyclopropyl-methyl | OMe | OH | H | H | 5'β-OH | H |
| Cyclopropyl-methyl | OMe | OH | H | 7'-F | 5'β-OH | H |
| Cyclopropyl-methyl | OMe | OH | 6'-OH | 7'-CO2Et | 5'β-OH | H |
| Cyclopropyl-methyl | OMe | OH | 6'-Me | 8'-NH2 | 5'β-OH | H |
| Cyclopropyl-methyl | OMe | OH | H | H | 5'α-OH | 5'β-Me |
| Cyclopropyl-methyl | OMe | OH | H | 7'-F | 5'α-OH | 5'β-Me |
| Cyclopropyl-methyl | OMe | OH | 6'-OH | 7'-CO2Et | 5'α-OH | 5'β-Me |
| Cyclopropyl-methyl | OMe | OH | 6'-Me | 8'-NH2 | 5'α-OH | 5'β-Me |
| Cyclopropyl-methyl | OMe | OH | H | H | 5'β-OH | 5'α-Me |
| Cyclopropyl-methyl | OMe | OH | H | 7'-F | 5'β-OH | 5'α-Me |
| Cyclopropyl-methyl | OMe | OH | 6'-OH | 7'-CO2Et | 5'β-OH | 5'α-Me |
| Cyclopropyl-methyl | OMe | OH | 6'-Me | 8'-NH2 | 5'β-OH | 5'α-Me |
| Cyclopropyl-methyl | OMe | OH | H | H | 4'-Oxo | |
| Cyclopropyl-methyl | OMe | OH | H | 7'-F | 4'-Oxo | |
| Cyclopropyl-methyl | OMe | OH | H | H | 5'-Oxo | |
| Cyclopropyl-methyl | OMe | OH | H | 7'-F | 5'-Oxo | |

The compound according to the present invention includes a compound represented by general formula (I)

wherein $R^4$ and $R^5$ are bound to each other to form a fused ring and also includes a compound represented by general formula (IC):

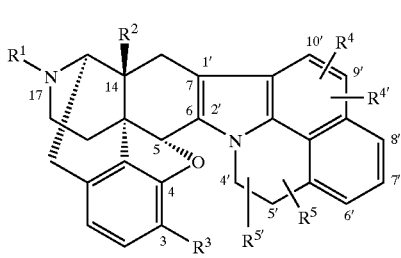

wherein $R^1$, $R^2$, $R^3$, $R^4$, $R^{4'}$, $R^5$, and $R^{5'}$ are as defined above.

Specific examples of compounds represented by general formula (IC) are shown in Tables 22 to 25.

TABLE 22

| R1 | R2 | R3 | R4 | R4' | R5 | R5' |
|---|---|---|---|---|---|---|
| Me | OH | OH | 9'-OH | H | H | H |
| Me | OH | OH | 9'-OH | 10'-F | H | H |
| Me | OH | OH | 9'-OH | 10'-CO2Et | H | H |
| Me | OH | OH | 10'-OH | H | H | H |
| Me | OH | OH | 10'-OH | 9'-Me | H | H |
| Me | OH | OH | 10'-OH | 9'-NH2 | H | H |
| Me | OH | OH | H | H | 4'α-OH | H |
| Me | OH | OH | H | 9'-F | 4'α-OH | H |
| Me | OH | OH | 9'-OH | 10'-CO2Et | 4'α-OH | H |
| Me | OH | OH | 9'-Me | 10'-NH2 | 4'α-OH | H |
| Me | OH | OH | H | H | 4'β-OH | H |
| Me | OH | OH | H | 9'-F | 4'β-OH | H |
| Me | OH | OH | 9'-OH | 10'-CO2Et | 4'β-OH | H |
| Me | OH | OH | 9'-Me | 10'-NH2 | 4'β-OH | H |
| Me | OH | OH | H | H | 5'α-OH | H |
| Me | OH | OH | H | 9'-F | 5'α-OH | H |
| Me | OH | OH | 9'-OH | 10'-CO2Et | 5'α-OH | H |
| Me | OH | OH | 9'-Me | 10'-NH2 | 5'α-OH | H |
| Me | OH | OH | H | H | 5'β-OH | H |
| Me | OH | OH | H | 9'-F | 5'β-OH | H |
| Me | OH | OH | 9'-OH | 10'-CO2Et | 5'β-OH | H |
| Me | OH | OH | 9'-Me | 10'-NH2 | 5'β-OH | H |
| Me | OH | OH | H | H | 5'α-OH | 5'β-Me |
| Me | OH | OH | H | 9'-F | 5'α-OH | 5'β-Me |
| Me | OH | OH | 9'-OH | 10'-CO2Et | 5'α-OH | 5'β-Me |
| Me | OH | OH | 9'-Me | 10'-NH2 | 5'α-OH | 5'β-Me |
| Me | OH | OH | H | H | 5'β-OH | 5'α-Me |
| Me | OH | OH | H | 9'-F | 5'β-OH | 5'α-Me |
| Me | OH | OH | 9'-OH | 10'-CO2Et | 5'β-OH | 5'α-Me |
| Me | OH | OH | 9'-Me | 10'-NH2 | 5'β-OH | 5'α-Me |
| Me | OH | OH | H | H | 4'-Oxo | |
| Me | OH | OH | H | 9'-F | 4'-Oxo | |
| Me | OH | OH | H | H | 5'-Oxo | |
| Me | OH | OH | H | 9'-F | 5'-Oxo | |
| Cyclopropyl-methyl | OH | OH | 9'-OH | H | H | H |
| Cyclopropyl-methyl | OH | OH | 9'-OH | 10'-F | H | H |
| Cyclopropyl-methyl | OH | OH | 9'-OH | 10'-CO2Et | H | H |
| Cyclopropyl-methyl | OH | OH | 10'-OH | H | H | H |
| Cyclopropyl-methyl | OH | OH | 10'-OH | 9'-Me | H | H |
| Cyclopropyl-methyl | OH | OH | 10'-OH | 9'-NH2 | H | H |
| Cyclopropyl-methyl | OH | OH | H | H | 4'α-OH | H |
| Cyclopropyl-methyl | OH | OH | H | 9'-F | 4'α-OH | H |
| Cyclopropyl-methyl | OH | OH | 9'-OH | 10'-CO2Et | 4'α-OH | H |
| Cyclopropyl-methyl | OH | OH | 9'-Me | 10'-NH2 | 4'α-OH | H |

TABLE 22-continued

| R1 | R2 | R3 | R4 | R4' | R5 | R5' |
|---|---|---|---|---|---|---|
| Cyclopropyl-methyl | OH | OH | H | H | 4'β-OH | H |
| Cyclopropyl-methyl | OH | OH | H | 9'-F | 4'β-OH | H |
| Cyclopropyl-methyl | OH | OH | 9'-OH | 10'-CO2Et | 4'β-OH | H |
| Cyclopropyl-methyl | OH | OH | 9'-Me | 10'-NH2 | 4'β-OH | H |
| Cyclopropyl-methyl | OH | OH | H | H | 5'α-OH | H |
| Cyclopropyl-methyl | OH | OH | H | 9'-F | 5'α-OH | H |
| Cyclopropyl-methyl | OH | OH | 9'-OH | 10'-CO2Et | 5'α-OH | H |

TABLE 23

| R1 | R2 | R3 | R4 | R4' | R5 | R5' |
|---|---|---|---|---|---|---|
| Cyclopropyl-methyl | OH | OH | 9'-Me | 10'-NH2 | 5'α-OH | H |
| Cyclopropyl-methyl | OH | OH | H | H | 5'β-OH | H |
| Cyclopropyl-methyl | OH | OH | H | 9'-F | 5'β-OH | H |
| Cyclopropyl-methyl | OH | OH | 9'-OH | 10'-CO2Et | 5'β-OH | H |
| Cyclopropyl-methyl | OH | OH | 9'-Me | 10'-NH2 | 5'β-OH | H |
| Cyclopropyl-methyl | OH | OH | H | H | 5'α-OH | 5'β-Me |
| Cyclopropyl-methyl | OH | OH | H | 9'-F | 5'α-OH | 5'β-Me |
| Cyclopropyl-methyl | OH | OH | 9'-OH | 10'-CO2Et | 5'α-OH | 5'β-Me |
| Cyclopropyl-methyl | OH | OH | 9'-Me | 10'-NH2 | 5'α-OH | 5'β-Me |
| Cyclopropyl-methyl | OH | OH | H | H | 5'β-OH | 5'α-Me |
| Cyclopropyl-methyl | OH | OH | H | 9'-F | 5'β-OH | 5'α-Me |
| Cyclopropyl-methyl | OH | OH | 9'-OH | 10'-CO2Et | 5'β-OH | 5'α-Me |
| Cyclopropyl-methyl | OH | OH | 9'-Me | 10'-NH2 | 5'β-OH | 5'α-Me |
| Cyclopropyl-methyl | OH | OH | H | H | 4'-Oxo | |
| Cyclopropyl-methyl | OH | OH | H | 9'-F | 4'-Oxo | |
| Cyclopropyl-methyl | OH | OH | H | H | 5'-Oxo | |
| Cyclopropyl-methyl | OH | OH | H | 9'-F | 5'-Oxo | |
| CH2CH2Ph | OH | OH | 9'-OH | H | H | H |
| CH2CH2Ph | OH | OH | 9'-OH | 10'-F | H | H |
| CH2CH2Ph | OH | OH | 9'-OH | 10'-CO2Et | H | H |
| CH2CH2Ph | OH | OH | 10'-OH | H | H | H |
| CH2CH2Ph | OH | OH | 10'-OH | 9'-Me | H | H |
| CH2CH2Ph | OH | OH | 10'-OH | 9'-NH2 | H | H |
| CH2CH2Ph | OH | OH | H | H | 4'α-OH | H |
| CH2CH2Ph | OH | OH | H | 9'-F | 4'α-OH | H |
| CH2CH2Ph | OH | OH | 9'-OH | 10'-CO2Et | 4'α-OH | H |
| CH2CH2Ph | OH | OH | 9'-Me | 10'-NH2 | 4'α-OH | H |
| CH2CH2Ph | OH | OH | H | H | 4'β-OH | H |
| CH2CH2Ph | OH | OH | H | 9'-F | 4'β-OH | H |
| CH2CH2Ph | OH | OH | 9'-OH | 10'-CO2Et | 4'β-OH | H |
| CH2CH2Ph | OH | OH | 9'-Me | 10'-NH2 | 4'β-OH | H |
| CH2CH2Ph | OH | OH | H | H | 5'α-OH | H |
| CH2CH2Ph | OH | OH | H | 9'-F | 5'α-OH | H |
| CH2CH2Ph | OH | OH | 9'-OH | 10'-CO2Et | 5'α-OH | H |
| CH2CH2Ph | OH | OH | 9'-Me | 10'-NH2 | 5'α-OH | H |
| CH2CH2Ph | OH | OH | H | H | 5'β-OH | H |
| CH2CH2Ph | OH | OH | H | 9'-F | 5'β-OH | H |
| CH2CH2Ph | OH | OH | 9'-OH | 10'-CO2Et | 5'β-OH | H |

TABLE 23-continued

| R1 | R2 | R3 | R4 | R4' | R5 | R5' |
|---|---|---|---|---|---|---|
| CH2CH2Ph | OH | OH | 9'-Me | 10'-NH2 | 5'β-OH | H |
| CH2CH2Ph | OH | OH | H | H | 5'α-OH | 5'β-Me |
| CH2CH2Ph | OH | OH | H | 9'-F | 5'α-OH | 5'β-Me |
| CH2CH2Ph | OH | OH | 9'-OH | 10'-CO2Et | 5'α-OH | 5'β-Me |
| CH2CH2Ph | OH | OH | 9'-Me | 10'-NH2 | 5'α-OH | 5'β-Me |
| CH2CH2Ph | OH | OH | H | H | 5'β-OH | 5'α-Me |
| CH2CH2Ph | OH | OH | H | 9'-F | 5'β-OH | 5'α-Me |
| CH2CH2Ph | OH | OH | 9'-OH | 10'-CO2Et | 5'β-OH | 5'α-Me |
| CH2CH2Ph | OH | OH | 9'-Me | 10'-NH2 | 5'β-OH | 5'α-Me |
| CH2CH2Ph | OH | OH | H | H | | 4'-Oxo |
| CH2CH2Ph | OH | OH | H | 9'-F | | 4'-Oxo |
| CH2CH2Ph | OH | OH | H | H | | 5'-Oxo |
| CH2CH2Ph | OH | OH | H | 9'-F | | 5'-Oxo |

TABLE 24

| R1 | R2 | R3 | R4 | R4' | R5 | R5' |
|---|---|---|---|---|---|---|
| Me | OMe | OH | 9'-OH | H | H | H |
| Me | OMe | OH | 9'-OH | 10'-F | H | H |
| Me | OMe | OH | 9'-OH | 10'-CO2Et | H | H |
| Me | OMe | OH | 10'-OH | H | H | H |
| Me | OMe | OH | 10'-OH | 9'-Me | H | H |
| Me | OMe | OH | 10'-OH | 9'-NH2 | H | H |
| Me | OMe | OH | H | H | 4'α-OH | H |
| Me | OMe | OH | H | 9'-F | 4'α-OH | H |
| Me | OMe | OH | 9'-OH | 10'-CO2Et | 4'α-OH | H |
| Me | OMe | OH | 9'-Me | 10'-NH2 | 4'α-OH | H |
| Me | OMe | OH | H | H | 4'β-OH | H |
| Me | OMe | OH | H | 9'-F | 4'β-OH | H |
| Me | OMe | OH | 9'-OH | 10'-CO2Et | 4'β-OH | H |
| Me | OMe | OH | 9'-Me | 10'-NH2 | 4'β-OH | H |
| Me | OMe | OH | H | H | 5'α-OH | H |
| Me | OMe | OH | H | 9'-F | 5'α-OH | H |
| Me | OMe | OH | 9'-OH | 10'-CO2Et | 5'α-OH | H |
| Me | OMe | OH | 9'-Me | 10'-NH2 | 5'α-OH | H |
| Me | OMe | OH | H | H | 5'β-OH | H |
| Me | OMe | OH | H | 9'-F | 5'β-OH | H |
| Me | OMe | OH | 9'-OH | 10'-CO2Et | 5'β-OH | H |
| Me | OMe | OH | 9'-Me | 10'-NH2 | 5'β-OH | H |
| Me | OMe | OH | H | H | 5'α-OH | 5'β-Me |
| Me | OMe | OH | H | 9'-F | 5'α-OH | 5'β-Me |
| Me | OMe | OH | 9'-OH | 10'-CO2Et | 5'α-OH | 5'β-Me |
| Me | OMe | OH | 9'-Me | 10'-NH2 | 5'α-OH | 5'β-Me |
| Me | OMe | OH | H | H | 5'β-OH | 5'α-Me |
| Me | OMe | OH | H | 9'-F | 5'β-OH | 5'α-Me |
| Me | OMe | OH | 9'-OH | 10'-CO2Et | 5'β-OH | 5'α-Me |
| Me | OMe | OH | 9'-Me | 10'-NH2 | 5'β-OH | 5'α-Me |
| Me | OMe | OH | H | H | | 4'-Oxo |
| Me | OMe | OH | H | 9'-F | | 4'-Oxo |
| Me | OMe | OH | H | H | | 5'-Oxo |
| Me | OMe | OH | H | 9'-F | | 5'-Oxo |
| Cyclopropyl-methyl | OMe | OH | 9'-OH | H | H | H |
| Cyclopropyl-methyl | OMe | OH | 9'-OH | 10'-F | H | H |
| Cyclopropyl-methyl | OMe | OH | 9'-OH | 10'-CO2Et | H | H |
| Cyclopropyl-methyl | OMe | OH | 10'-OH | H | H | H |
| Cyclopropyl-methyl | OMe | OH | 10'-OH | 9'-Me | H | H |
| Cyclopropyl-methyl | OMe | OH | 10'-OH | 9'-NH2 | H | H |
| Cyclopropyl-methyl | OMe | OH | H | H | 4'α-OH | H |
| Cyclopropyl-methyl | OMe | OH | H | 9'-F | 4'α-OH | H |
| Cyclopropyl-methyl | OMe | OH | 9'-OH | 10'-CO2Et | 4'α-OH | H |
| Cyclopropyl-methyl | OMe | OH | 9'-Me | 10'-NH2 | 4'α-OH | H |
| Cyclopropyl-methyl | OMe | OH | H | H | 4'β-OH | H |
| Cyclopropyl-methyl | OMe | OH | H | 9'-F | 4'β-OH | H |
| Cyclopropyl-methyl | OMe | OH | 9'-OH | 10'-CO2Et | 4'β-OH | H |
| Cyclopropyl-methyl | OMe | OH | 9'-Me | 10'-NH2 | 4'β-OH | H |
| Cyclopropyl-methyl | OMe | OH | H | H | 5'α-OH | H |
| Cyclopropyl-methyl | OMe | OH | H | 9'-F | 5'α-OH | H |
| Cyclopropyl-methyl | OMe | OH | 9'-OH | 10'-CO2Et | 5'α-OH | H |

TABLE 25

| R1 | R2 | R3 | R4 | R4' | R5 | R5' |
|---|---|---|---|---|---|---|
| Cyclopropyl-methyl | OMe | OH | 9'-Me | 10'-NH2 | 5'α-OH | H |
| Cyclopropyl-methyl | OMe | OH | H | H | 5'β-OH | H |
| Cyclopropyl-methyl | OMe | OH | H | 9'-F | 5'β-OH | H |
| Cyclopropyl-methyl | OMe | OH | 9'-OH | 10'-CO2Et | 5'β-OH | H |
| Cyclopropyl-methyl | OMe | OH | 9'-Me | 10'-NH2 | 5'β-OH | H |
| Cyclopropyl-methyl | OMe | OH | H | H | 5'α-OH | 5'β-Me |
| Cyclopropyl-methyl | OMe | OH | H | 9'-F | 5'α-OH | 5'β-Me |
| Cyclopropyl-methyl | OMe | OH | 9'-OH | 10'-CO2Et | 5'α-OH | 5'β-Me |
| Cyclopropyl-methyl | OMe | OH | 9'-Me | 10'-NH2 | 5'α-OH | 5'β-Me |
| Cyclopropyl-methyl | OMe | OH | H | H | 5'β-OH | 5'α-Me |
| Cyclopropyl-methyl | OMe | OH | H | 9'-F | 5'β-OH | 5'α-Me |
| Cyclopropyl-methyl | OMe | OH | 9'-OH | 10'-CO2Et | 5'β-OH | 5'α-Me |
| Cyclopropyl-methyl | OMe | OH | 9'-Me | 10'-NH2 | 5'β-OH | 5'α-Me |
| Cyclopropyl-methyl | OMe | OH | H | H | | 4'-Oxo |
| Cyclopropyl-methyl | OMe | OH | H | 9'-F | | 4'-Oxo |
| Cyclopropyl-methyl | OMe | OH | H | H | | 5'-Oxo |
| Cyclopropyl-methyl | OMe | OH | H | 9'-F | | 5'-Oxo |

Specifically, the compound represented by general formula (I) according to the present invention can be produced by the method shown in Scheme 1.

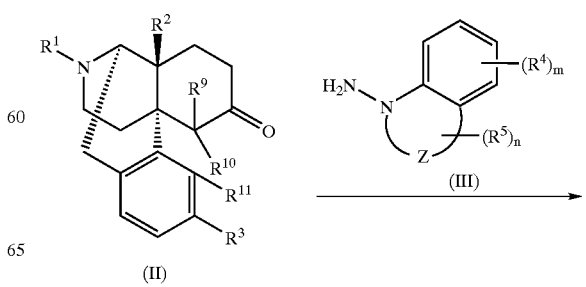

Scheme 1

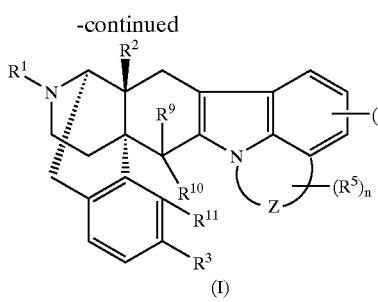

(I)

Specifically, the compound can be obtained by allowing a morphinan derivative represented by general formula (II) wherein $R^1$, $R^2$, $R^3$, $R^9$, $R^{10}$, and $R^{11}$ are as defined in general formula (I) to react with a hydrazine derivative represented by general formula (III) wherein —Z—, m, n, $R^4$, and $R^5$ are as defined in general formula (I) in a solvent in the presence of an acid catalyst.

Examples of solvents which can be used herein include: alcoholic solvents such as methanol, ethanol, 1-propanol, and 2-propanol; aprotic dipolar solvents such as DMF and DMSO; aromatic hydrocarbon solvents such as benzene, toluene, and xylene; ether solvents such as diethyl ether, THF, and DME; halogenated solvents such as dichloromethane, chloroform, carbon tetrachloride, and 1,2-dichloroethane; and organic acids that can be used as solvents such as acetic acid and propionic acid. Among these solvents, preferred are alcoholic solvents such as methanol, ethanol, 1-propanol, and 2-propanol; aprotic dipolar solvents such as DMF and DMSO; organic acids that can be used as solvents such as acetic acid and propionic acid. Methanol, ethanol, DMF, and acetic acid are particularly preferred.

Examples of acid catalysts which can be used include: inorganic acids such as hydrochloric acid, sulfuric acid, nitric acid, hydrobromic acid, and hydroiodic acid; organic sulfonic acids such as methanesulfonic acid, ethanesulfonic acid, benzenesulfonic acid, p-toluenesulfonic acid, and camphorsulfonic acid; organic carboxylic acids such as acetic acid, lactic acid, citric acid, oxalic acid, glutaric acid, malic acid, tartaric acid, fumaric acid, mandelic acid, maleic acid, benzoic acid, and phthalic acid (incidentally, although the reaction may not smoothly progress with organic calboxylic acid alone, a strong acid may be optionally added as a cocatalyst in such a case); and acidic ion-exchange resin. Among these acid catalysts, hydrochloric acid, sulfuric acid, methanesulfonic acid, p-toluenesulfonic acid, and acidic ion-exchange resin are preferably used. Furthermore, the equivalent ratio of the acid catalyst to be used relative to the total amount of base present in the reaction system is from 1 to 30, and preferably from 1 to 10. The acid catalyst may be added after converting the base component into salt, or may be added into the reaction mixture in a desired amount. The reaction temperature can be from 0° C. to 300° C., and preferably from 0° C. to 170° C. A range of 25° C. to 120° C. is particularly preferable.

Among the compounds represented by general formula (I) according to the present invention, a compound represented by general formula (Ia), wherein two $R^5$ groups are bound to the same carbon atom to form oxo (wherein $R^1$, $R^2$, $R^3$, $R^4$, $R^9$, $R^{10}$, $R^{11}$, and m are as defined in general formula (I); n is an integer from 0 to 8; —$Z_1$— and —$Z_2$— are independently a crosslinkage having 0 to 4 carbon atoms (wherein the total number of crosslinked carbons of —$Z_1$— and —$Z_2$— is 1 to 4)), and a compound represented by general formula (Ib) wherein one $R^5$ group is hydroxy;

(wherein $R^1$, $R^2$, $R^3$, $R^4$, $R^9$, $R^{10}$, $R^{11}$, m, n, —$Z_1$—, and —$Z_2$— are as defined above) can also be produced by the method shown in Scheme 2.

Scheme 2

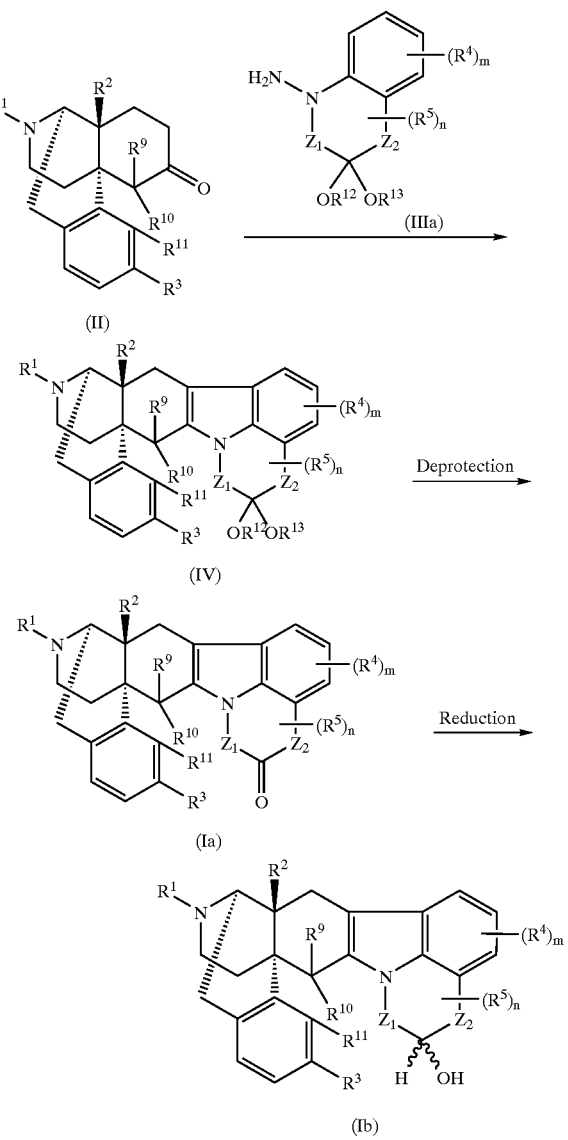

Specifically, a morphinan derivative represented by general formula (II) wherein $R^1$, $R^2$, $R^3$, $R^9$, $R^{10}$, and $R^{11}$ are as defined above is reacted with a hydrazine derivative represented by general formula (IIIa) wherein —$Z_1$—, —$Z_2$—, m, n, $R^4$, and $R^5$ are as defined above; and $R^{12}$ and $R^{13}$ may be a carbonyl protecting group wherein both are methyl or acetyl, or $R^{12}$ and $R^{13}$ may be bound to each other to form a 1,3-dioxolan or 1,3-dioxane ring under the same reaction condition as in Scheme 1 to be converted into a compound represented by general formula (W) wherein $R^1$, $R^2$, $R^3$, $R^4$, $R^5$, $R^9$, $R^{10}$, $R^{11}$, $R^{12}$, $R^{13}$, m, n, —$Z_1$—, and —$Z_2$— are as defined above, followed by deprotection of carbonyl that is commonly performed. Thus, Compound (Ia) can be obtained. When $R^{12}$ and $R^{13}$ are both methyl or a 1,3-dioxolan or 1,3-dioxane ring is formed through a $R^{12}$—$R^{13}$ bond, deprotection can be carried out by allowing a reaction to proceed in the presence of an acid catalyst in a solvent with, for example, water or acetone. When $R^{12}$ and $R^{13}$ are both acetyl, deprotection can be carried out by allowing a base to act in a solvent.

Compound (Ib) can be produced by causing a commonly used reducing agent in a solvent to act on Compound (Ia) obtained above, thereby converting carbonyl into hydroxy. Examples of a reducing agent include sodium borohydride, sodium cyanoborohydride, lithium aluminum hydride, and LS-selectride. Compound (Ib) can be obtained as a mixture of α-hydroxy and β-hydroxy, and they can be separated from each other by chromatography, recrystallization, or the like.

Among the compounds represented by general formula (I) according to the present invention, a compound represented by general formula (Ic), wherein two $R^5$ groups are bound to a carbon atom adjacent to a benzene ring of indole to form oxo (wherein $R^1$, $R^2$, $R^3$, $R^4$, $R^5$, $R^9$, $R^{10}$, $R^{11}$, and m are as defined in general formula (I); n is an integer from 0 to 8; —$Z_3$— is a $C_{1-4}$ crosslinkage), and a compound represented by general formula (Id), wherein one $R^5$ group bound to a carbon atom adjacent to a benzene ring of indole is hydroxy, (wherein $R^1$, $R^2$, $R^3$, $R^4$, $R^5$, $R^9$, $R^{10}$, $R^{11}$, m, n, and —$Z_3$— is as defined above) can also be produced by the method shown in Scheme 3.

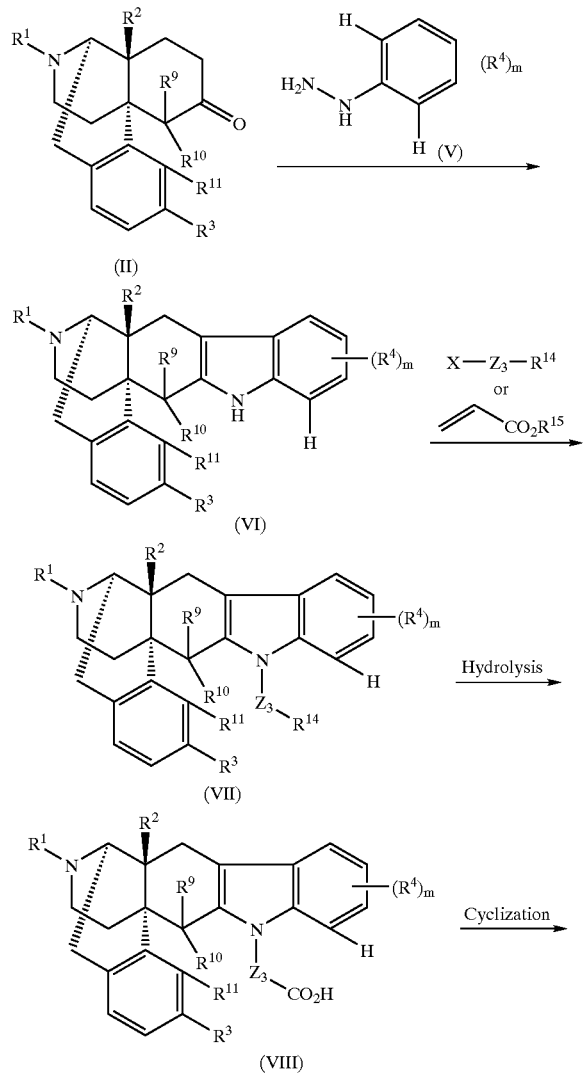

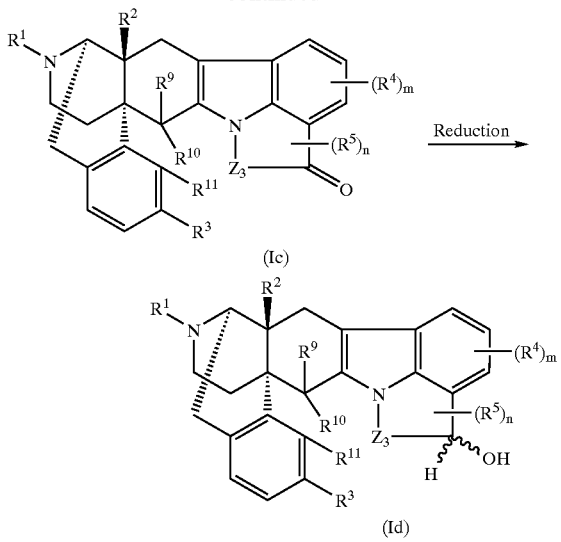

Specifically, a morphinan derivative represented by general formula (II) wherein $R^1$, $R^2$, $R^3$, $R^9$, $R^{10}$, and $R^{11}$ are as defined above is reacted with a hydrazine derivative represented by general formula (V) wherein m and $R^4$ are as defined above under the same reaction condition as in Scheme 1. Thus, a compound represented by general formula (VI) wherein $R^1$, $R^2$, $R^3$, $R^4$, $R^9$, $R^{10}$, $R^{11}$, and m are as defined above can be produced.

A compound represented by general formula (VII) wherein $R^1$, $R^2$, $R^3$, $R^4$, $R^9$, $R^{10}$, $R^{11}$, —$Z_3$—, and m are as defined above, $R^{14}$ is nitrile or $CO_2R^{15}$ wherein $R^{15}$ is $C_{1-5}$ alkyl can be synthesized by performing common alkylation of amino groups to Compound (VI). Examples of alkylation include a method wherein an alkylating agent represented by X—$Z_3$—$R^{14}$ wherein $R^{14}$ is as defined above; —$Z_3$— is a crosslinkage having 1 to 4 carbon atoms that may be optionally substituted with n number of $R^5$ groups; and X is chloro, bromo, iodo, TsO, or MsO, or acrylic ester ($CH_2$=CH—$CO_2R^{15}$ wherein $R^{15}$ is as defined above) is reacted with a base in a solvent. In such a reaction, a reaction time can be shortened with the addition of phase-transfer catalysts such as tetrabutylammonium chloride or triethylbenzylammonium chloride.

$R^{14}$ in a compound represented by general formula (VII) can be converted into carboxylic acid by hydrolyzing nitrile or ester, thereby obtaining a compound represented by general formula (VIII) wherein $R^1$, $R^2$, $R^3$, $R^4$, $R^9$, $R^{10}$, $R^{11}$, —$Z_3$—, and m are as defined above.

Compound (Ic) can be produced by cyclization of Compound (VIII). Cyclization can be carried out by common Friedel-Crafts acylation, and examples include the following two methods. Specific examples include (1) a method that is carried out by causing methanesulfonic acid and phosphorus pentoxide to act on Compound (VIII) and (2) a method that is carried out by converting the carboxylic compound (VIII) into an acid chloride using oxalyl chloride, thionyl chloride, or the like, and then causing acids such as aluminum chloride to act on the acid chloride.

Further, Compound (Id) can be produced by causing a common reducing agent in a solvent to act on Compound (Ic), and converting carbonyl into hydroxy. Examples of a reducing agent include sodium borohydride, sodium cyanoborohydride, lithium aluminum hydride, and LS-selectride. Compound (Id) can be obtained as a mixture of α-hydroxy and β-hydroxy, and they can be separated from each other by chromatography, recrystallization, or the like.

Among compounds represented by general formula (I) according to the present invention, a compound represented by general formula (If) wherein $R^1$, $R^2$, $R^3$, $R^5$, $R^9$, $R^{10}$, $R^{11}$, and n are as defined in general formula (I); $R^4$ is as defined in general formula (I) or hydrogen, and at least one of m number of $R^4$ groups is hydroxy; —Z— is a crosslinkage having 2 to 5 carbon atoms; and m is an integer from 1 to 3 can also be produced by the method shown in Scheme 4.

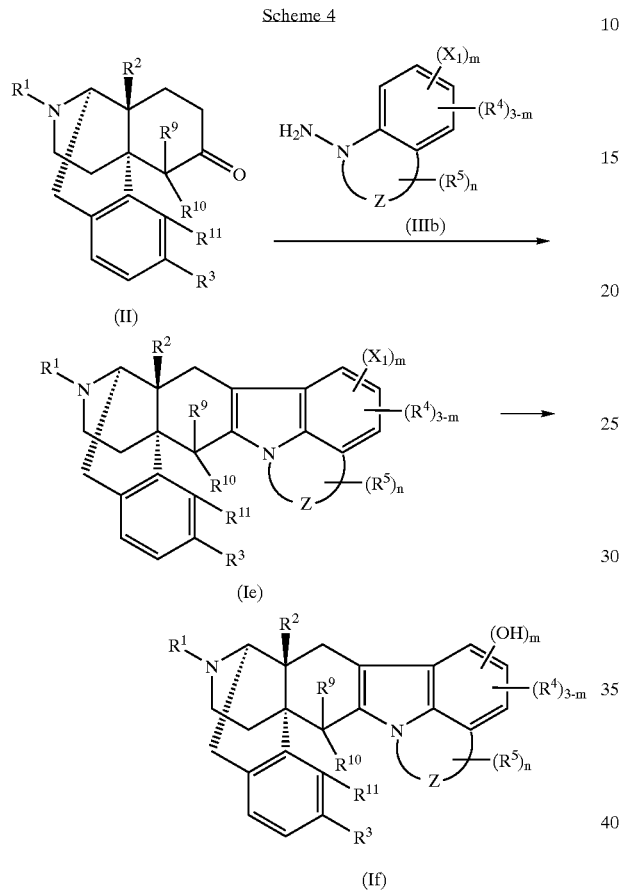

(If)

Specifically, a morphinan derivative represented by general formula (II) wherein $R^1$, $R^2$, $R^3$, $R^9$, $R^{10}$, and $R^{11}$ are as defined above is reacted with a hydrazine derivative represented by general formula (IIIb) wherein —Z—, m, n, $R^4$, and $R^5$ are as defined above; and $X_1$ is methoxy or bromo under the same reaction condition as in Scheme 1 to synthesize a compound represented by general formula (Ie) wherein $R^1$, $R^2$, $R^3$, $R^4$, $R^5$, $R^9$, $R^{10}$, $R^{11}$, m, n, —Z—, and $X_1$ are as defined above. Subsequently, $X_1$ in Compound (Ie) is converted into hydroxy, thereby producing Compound (If). Examples of methods for converting $X_1$ into hydroxy include: when $X_1$ is methoxy, a method that is carried out by causing a base such as $CH_3(CH_2)_2SK$ to act on Compound (Ie) in a solvent such as dimethylformamide, and a method that is carried out by causing acid such as $BBr_3$ in a solvent such as dichloromethane. When $X_1$ is bromo, an example of methods for converting $X_1$ into hydroxy is a method that is carried out by causing an organic lithium compound such as n-butyl lithium to act on Compound (Ie) in a solvent such as THF to convert $X_1$ into lithio, followed by oxidation thereof using nitrobenzene or the like, thereby converting $X_1$ into hydroxy.

Among compounds represented by general formula (I) according to the present invention, a compound represented by general formula (Ig), wherein one $R^5$ group bound to a carbon atom adjacent to a nitrogen atom is hydroxy (wherein $R^1$, $R^2$, $R^3$, $R^4$, $R^5$, $R^9$, $R^{10}$, and $R^{11}$ are as defined in general formula (I); —$Z_4$— is a crosslinkage having 1 to 4 carbon atoms; m is an integer from 0 to 3; and n is an integer from 0 to 8), can be also produced by the method shown in Scheme 5.

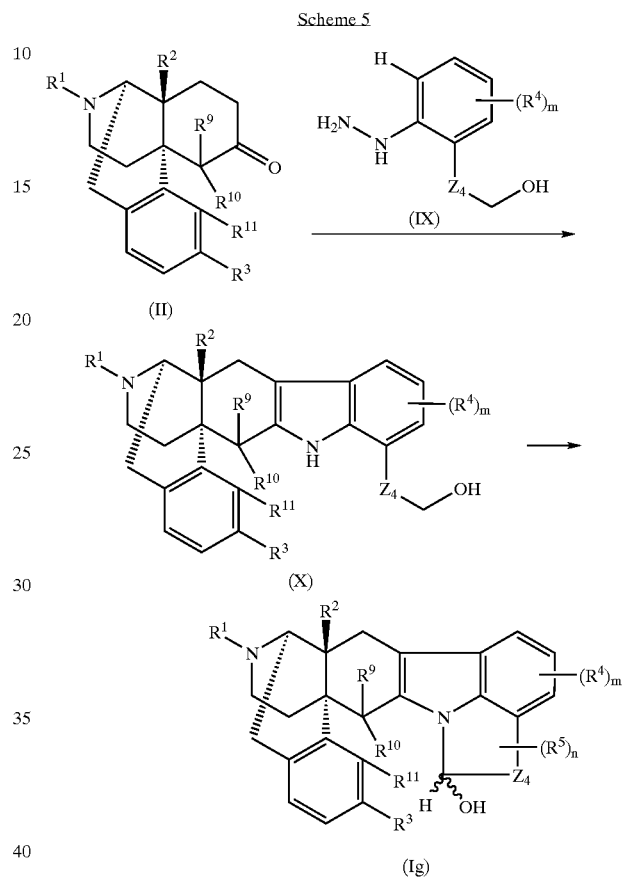

(Ig)

Specifically, a morphinan derivative represented by general formula (II) wherein $R^1$, $R^2$, $R^3$, $R^9$, $R^{10}$, and $R^{11}$ are as defined above is reacted with a hydrazine derivative represented by general formula (IX) wherein m and $R^4$ are as defined above, and —$Z_4$— is a crosslinkage having 1 to 4 carbon atoms that may be optionally substituted with n number of $R^5$ groups under the same reaction condition as in Scheme 1. Thus, a compound represented by general formula (X) wherein $R^1$, $R^2$, $R^3$, $R^4$, $R^5$, $R^9$, $R^{10}$, $R^{11}$, —Z—, m, and n are as defined above can be synthesized. Subsequently, hydroxy in Compound (X) is oxidized to convert into aldehyde. This allows the cyclization to proceed, and thus, Compound (Ig) can be obtained. An example of oxidation that can be preferably used is Swern oxidation. Compound (Ig) can be obtained as a mixture of α-hydroxy and β-hydroxy, and they can be separated from each other by chromatography, recrystallization, or the like.

The indole derivative represented by general formula (I) according to the present invention is useful as a pharmaceutical. Specifically, it can be used as a drug acting on δ opioid receptor, i.e., as a δ opioid receptor agonist or δ opioid receptor antagonist. Since the compound according to the present invention selectively acts on the δ opioid receptor, it can be used as an agent such as an analgesic, antitussive, immunosuppressive agent, or brain-cellprotecting agent that does not exhibit side effect resulting from a μ or κ opioid receptor such as drug dependence, suppression of the CNS, constipation, respiratory depression, drug aversion, or psychotomimetic effects.

When the compound of the present invention is used as an agent such as an analgesic, antitussive, immunosuppressive agent, or brain-cell-protecting agent in clinical practice, the agent may be a free base or its salt per se. Alternatively, an additive such as an excipient, stabilizer, preservative, buffer, solubilizing agent, emulsifier, diluent, or isotonizing agent may be suitably mixed. Examples of dosage forms include: oral preparations such as tablets, capsules, granules, powders, or syrups; parenteral preparations such as injections, suppositories, or liquid drugs; and local administration by ointments, cream pharmaceuticals, patches, or the like. The agents relating to δ opioid receptors such as analgesics, antitussives, immunosuppressive agents, or brain-cell-protecting agents according to the present invention comprise the aforementioned active ingredient in amounts of preferably 0.00001 to 90% by weight, and more preferably 0.0001 to 70% by weight. Amounts used may be suitably selected depending on symptom, age, body weight, medication method, etc. In the case of injections, the amount of active ingredients is 0.1 μg to 1 g and 1 μg to 10 g in the case of oral preparations per day per adult. These preparations can be administered in one dose or several separate doses.

This description includes part or all of the contents as disclosed in the description of Japanese Patent Application No. 2000-356382, which is a priority document of the present application.

BEST MODES FOR CARRYING OUT THE INVENTION

The present invention is hereafter described in more detail with reference to examples. These examples, however, are not intended to limit the technical scope of the present invention.

EXAMPLE 1

17-Cyclopropylmethyl-6,7-didehydro-4,5α-epoxy-8'-fluoro-6'-oxo-5',6'-dihydro-4'H-pyrrolo[3,2,1-ij]quinolino[2',1':6,7]morphinan-3,14β-diol 1.

Naltrexone benzoate (4.33 g, 14.4 mmol) and 1-amino-4-(1,3-dioxolan-2-yl)-6-fluoro-1,2,3,4-tetrahydroquinoline 1a (3.3 g, 1 eq) were mixed in acetic acid (60 mL), and the mixture was stirred at room temperature for 15 hours. After the completion of the reaction, the reaction solution was poured dropwise onto a mixture of chloroform (300 mL) and an aqueous solution of 10% sodium hydroxide (500 mL), which was cooled to 0° C. An organic phase was separated and an aqueous phase was extracted with chloroform (200 mL×5). The organic phase was collected, dried over anhydrous sodium sulfate, and then concentrated. The resulting crude product contained a keto compound from which ketal at the 6'-position had been removed, and this product was purified by column chromatography on silica gel (DM 1020, Fuji Silysia, 60 g; chloroform/methanol=50/1→30/1). Thus, 640 mg of the object product was obtained.

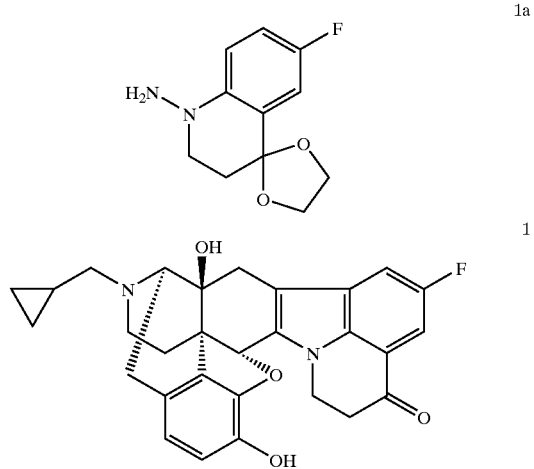

EXAMPLES 2 AND 3

17-Cyclopropylmethyl-6,7-didehydro-4,5α-epoxy-8'-fluoro-5',6'-dihydro-4'H-pyrrolo-[3,2,1-ij]quinolino[2',1':6,7]morphinan-3,6'α,14β-triol 2-benzoate and 17-cyclopropylmethyl-6,7-didehydro-4,5α-epoxy-8'-fluoro-5',6'-dihydro-4'H-pyrrolo[3,2,1-ij]quinolino[2',1':6,7]-morphinan-3,6'β,14β-triol 3-methanesulfonate.

17-Cyclopropylmethyl-4,5α-epoxy-3-methoxy-6-oxomorphinan-14β-ol 2a (17 g, 47.8 mmol), 4-fluorophenylhydrazine hydrochloride (1.8 g, 1 eq), and methanesulfonic acid (4.6 g, 1 eq) were mixed in ethanol (220 mL), and the mixture was heated under reflux for 14 hours. After cooling, an aqueous solution of 10% sodium hydroxide (60 mL) was added, and a precipitate was collected by filtration. The resulting crude product was recrystallized from a mixed solvent of tetrahydrofuran (150 mL) and ethanol (200 mL) for purification. Thus, 17-cyclopropylmethyl-6,7-didehydro-4,5α-epoxy-5'-fluoro-3-methoxy-indolo[2',3':6,7]morphinan-14β-ol 2b was obtained (18 g, yield 90%).

2b (5.5 mg, 12.7 mmol) and 3-bromopropionitrile (3.4 g, 2 eq) were mixed in benzene (80 mL), and sodium hydroxide (13 g, 25 eq) was added thereto in a dissolved state in distilled water (14 g). Tetrabutylammonium chloride (1.8 g, 0.5 eq) was added, and the mixture was heated under reflux for 1 hour. After cooling, distilled water (100 mL) was added, liquid separation was performed, and extraction with chloroform (100 mL×3) was performed. The resultant was dried over anhydrous magnesium sulfate and concentrated. The resulting crude product was recrystallized from methanol for purification. Thus, 1'-(2-cyanoethyl)-17-cyclopropylmethyl-6,7-didehydro-4,5α-epoxy-5'-fluoro-3-methoxy-indolo-[2',3';6,7]morphinan-14β-ol 2c was obtained (5.7 g, yield 91%).

2c (5.7 g) and sodium hydroxide (9.2 g) were mixed in a mixture of tetrahydrofuran (200 mL), ethanol (100 L), and distilled water (50 mL), and the mixture was stirred at 85° C. for 44 hours. After cooling, the reaction solution was poured onto a mixture of ethyl acetate (300 mL) and saturated brine (100 mL), liquid separation was performed, and the organic phase was extracted with ethyl acetate (100 mL×3). The resultant was dried over anhydrous magnesium sulfate and concentrated. Thus, 1'-(2-carboxyethyl)-17-cyclopropylmethyl-6,7-didehydro-4,5α-epoxy-5'-fluoro-3-methoxy-indolo[2',3':6,7]morphinan-14β-ol 2d was obtained (quantitatively).

2d (1 g, 1.64 mmol) was dissolved in anhydrous dichloromethane (10 mL), oxalyl dichloride was slowly added dropwise (0.5 mL, 2.5 eq), and the mixture was stirred at room temperature for 30 minutes. Dimethylformamide (0.01 mL) was added, the mixture was stirred at room temperature for 10 minutes, and the reaction solution was then concentrated. Nitrobenzene (10 mL) and anhydrous aluminum chloride (547 mg, 2.5 eq) were added, and the mixture was stirred for 30 minutes. After the completion of the reaction, distilled water (1 mL) was slowly added dropwise, the reaction solution was poured onto a mixture of chloroform (100 mL) and saturated sodium bicarbonate water (100 mL), liquid separation was performed, and the organic phase was filtered using Celite. Distilled water (100 mL) was added to this solution, liquid separation was performed, and extraction with chloroform (100 mL×3) was performed. After the resultant was concentrated, ethyl acetate (200 mL) and methanesulfonic acid (236 mg) were added, and liquid separation was performed. After the organic phase was extracted with distilled water, ethyl acetate (300 mL) and saturated aqueous sodium bicarbonate were added to alkalize the solution. Liquid separation was performed, and an aqueous phase was extracted with ethyl acetate (100 mL×3). The resultant was dried over anhydrous magnesium sulfate and concentrated to obtain 17-cyclopropylmethyl-6,7-didehydro-4,5α-epoxy-8'-fluoro-3-methoxy-6'-oxo-5',6'-dihydro-4'H-pyrrolo[3,2,1-ij]quinolino[2',1':6,7]morphinan-14β-ol 2e (690 mg, yield 84%).

2e (11.7 g, 23.4 mmol) was dissolved in tetrahydrofuran (50 mL) and methanol (150 mL), and sodium borohydride (2.7 g, 3 eq) was added at 0° C. After stirring for 30 minutes, distilled water (200 mL) and chloroform (400 mL) were added for liquid separation, and extraction with chloroform (200 mL×1) was then performed. The resultant was dried over anhydrous magnesium sulfate and concentrated. The resulting crude product was purified by column chromatography on silica gel (Silica gel 7734, Merck, 600 g; chloroform /methanol=70/1→20/1). Thus, 4.7 g of a low polarity component, 17-cyclopropylmethyl-6,7-didehydro-4,5α-epoxy-8'-fluoro-3-methoxy-5',6'-dihydro-4'H-pyrrolo[3,2,1-ij]quinolino[2',1':6,7]morphinan-6'α,14β-diol 2f, and 2.9 g of a high polarity component, 17-cyclopropylmethyl-6,7-didehydro-4,5α-epoxy-8'-fluoro-3-methoxy-5',6'-dihydro-4'H-pyrrolo[3,2,1-ij]quinolino[2',1':6,7]morphinan-6'β,14β-diol 3f, were obtained.

2f (4.7 g, 9.3 mmol) and n-propanethiol (5.1 mL, 6 eq) were mixed in dimethylformamide (70 mL), potassium t-butoxide (5.7 g, 5 eq) was added thereto, and the mixture was stirred at 135° C. for 2.5 hours. After cooling, the reaction solution was transferred into a mixture of toluene (200 mL) and distilled water (200 mL), methanesulfonic acid (5 g) was added thereto, and the mixture was then stirred. Thereafter, saturated aqueous sodium bicarbonate was added until the aqueous phase became alkalized. Liquid separation was performed, extraction with toluene (200 mL×3) was performed, and the organic phase was washed with distilled water (200 mL×2). The resultant was dried over magnesium sulfate and concentrated. The resulting crude product was purified by recrystallization from THF. Thus, 3.47 g of a free base substance of the object product was obtained. This product was dissolved in ethyl acetate, a solution of benzoic acid (1 eq) in ethyl acetate was added, and the solvent was removed by distillation. The resultant was suspended in ether and collected by filtration, thereby obtaining the object product 2-benzoate. Also, 3f was used as a starting material instead of 2f to obtain 3. This product was converted to methanesulfonate, and the object product 3-methanesulfonate was obtained.

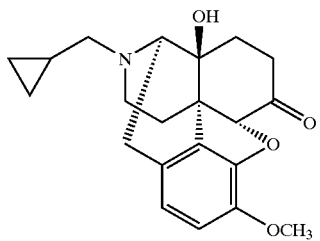

2a

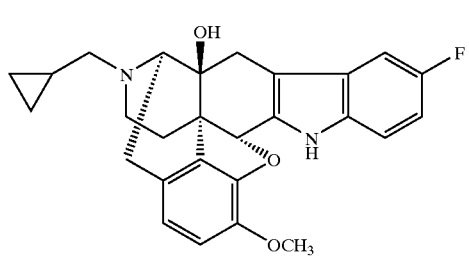

2b

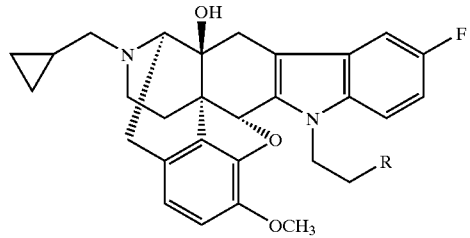

2c (R = CN)
2d (R = CO₂H)

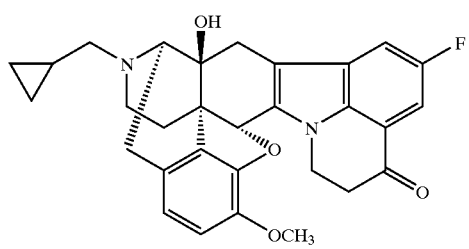

2e

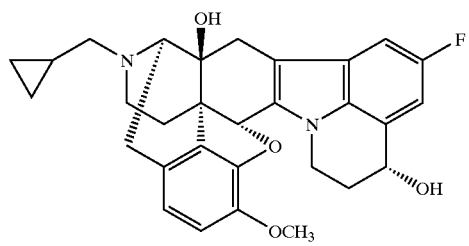

2f

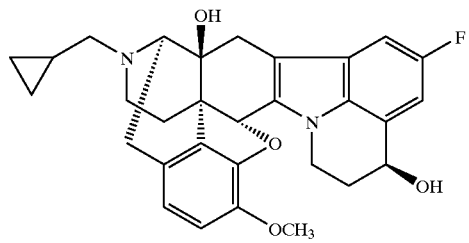

3f

2

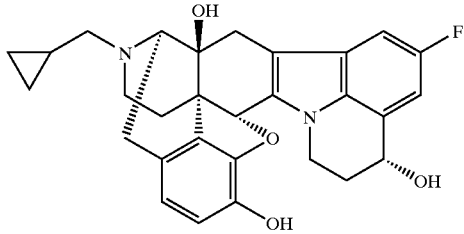

3

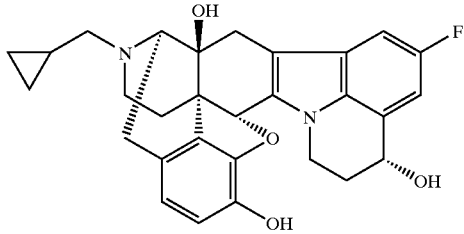

EXAMPLES 4 AND 5

17-Allyl-6,7-didehydro-4,5α-epoxy-8'-fluoro-5',6'-dihydro-4'H-pyrrolo[3,2,1-ij]quinolino-[2',1':6,7]morphinan-3,6'α,14β-triol 4 and 17-allyl-6,7-didehydro-4,5α-epoxy-8'-fluoro-5',6'-dihydro-4'H-pyrrolo[3,2,1-ij]quinolino[2',1':6,7]morphinan-3,6'β,14β-triol 5.

Object products were synthesized in accordance with the method described in Examples 2 and 3. As a starting material, 17-allyl-4,5α-epoxy-3-methoxy-6-oxomorphinan-14β-ol 4a and 4-fluorophenylhydrazine hydrochloride were used to obtain 17-allyl-6,7-didehydro-4,5α-epoxy-5'-fluoro-3-methoxy-indolo[2',3':6,7]morphinan-14β-ol 4b.

4b (17.8 g, 41.2 mmol), ethyl acrylate (10 g, 2 eq), tetrabutylammonium chloride (16 g, 0.5 eq), and potassium carbonate (17 g, 3 eq) were mixed in acetonitrile (450 mL), and the mixture was heated under reflux for 3 hours. After cooling, insoluble matter was separated by filtration, and the filtrate was concentrated. After the concentrate was dissolved in chloroform (350 mL), distilled water (250 mL) was added for liquid separation, and anhydrous magnesium sulfate was added for drying, followed by concentration. Thus, 17-allyl-6,7-didehydro-4,5α-epoxy-1'(ethoxycarbonylethyl)-5'-fluoro-3-methoxy-indolo[2',3':6,7]-morphinan-14β-ol 4c was obtained.

Sodium hydroxide was allowed to act on 4c (2.2 g) for hydrolysis. Thus, 1'-(2-carboxyethyl)-17-allyl-6,7-didehydro-4,5'-epoxy-5'-fluoro-3-methoxy-indolo[2',3':6,7]-morphinan-14β-ol 4d was obtained.

Oxalyl dichloride was allowed to act on 4d and then aluminum chloride was allowed to act thereon. Thus, 17-allyl-6,7-didehydro-4,5α-epoxy-8'-fluoro-6'-oxo-3-methoxy-5',6'-dihydro-4'H-pyrrolo[3,2,1-ij]quinolino[2',1':6,7]morphinan-14β-ol 4e was obtained.

Sodium borohydride was allowed to act on 4e for reduction. Thus, 17-allyl-6,7-didehydro-4,5α-epoxy-8'-fluoro-3-methoxy-5',6'-dihydro-4'H-pyrrolo[3,2,1-ij]-quinolino[2',1':6,7]morphinan-6'α,14β-diol 4f and 17-allyl-6,7-didehydro-4,5α-epoxy-8'-fluoro-3-methoxy-5',6'-dihydro-4'H-pyrrolo[3,2,1-ij]quinolino[2',1':6,7]morphinan-6'β,14β-diol 5f were obtained.

The object product 4 was obtained by allowing n-propanethiol and potassium t-butoxide to act on 4f. Also, the object product 5 was obtained by using 5f instead of 4f as a starting material.

4a

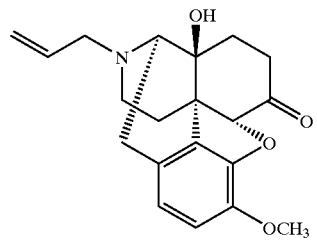

4b

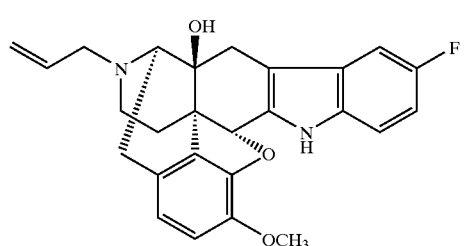

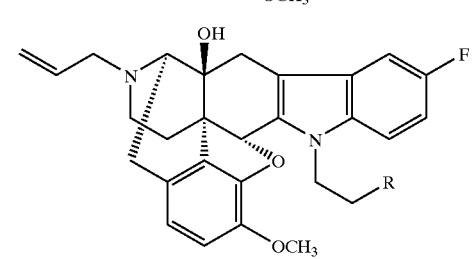

4c(R = CO₂Et)
4d(R = CO₂H)

4e

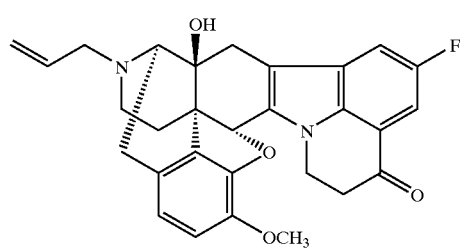

4f

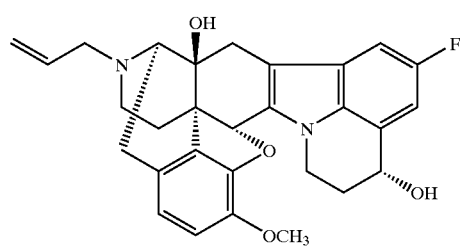

5f

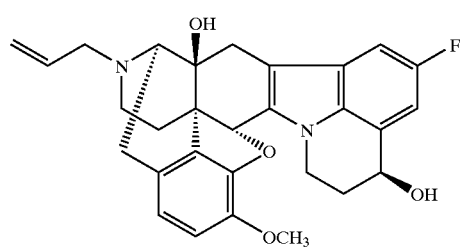

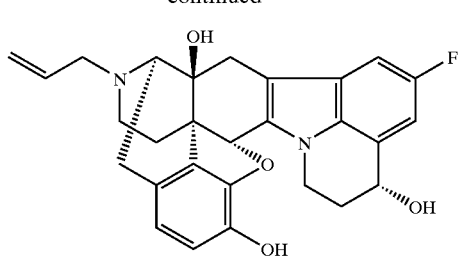

4

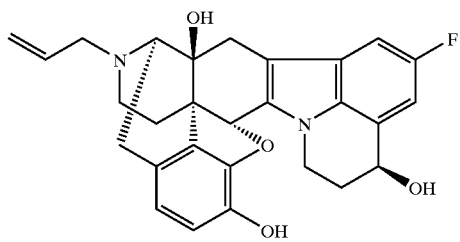

5

EXAMPLES 6 AND 7

6,7-Didehydro-4,5α-epoxy-8'-fluoro-17-methyl-5',6'-dihydro-4'H-pyrrolo[3,2,1-ij]-quinolino[2',1':6,7]morphinan-3,6'α,14β-triol 6-benzoate and 6,7-didehydro-4,5α-epoxy-8'-fluoro-17-methyl-5',6'-dihydro-4'H-pyrrolo[3,2,1-ij]quinolino[2',1';6,7]morphinan-3,6'β,14β-triol 7-benzoate.

Object products were synthesized in accordance with the method described in Examples 4 and 5. As a starting material, 4,5α-epoxy-3-methoxy-17-methyl-6-oxomorphinan-14β-ol was used to obtain 6 and 7. Object products were obtained converting these substances into salts of benzoic acid.

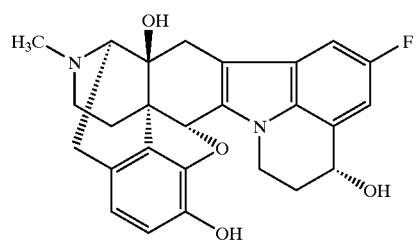

6

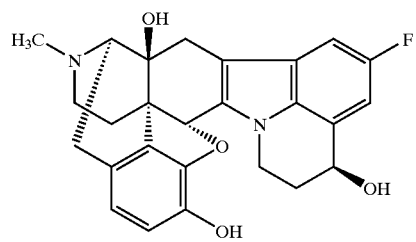

7

EXAMPLES 8 AND 9

6,7-Didehydro-4,5α-epoxy-8'-fluoro-5',6'-dihydro-4'H-pyrrolo[3,2,1-ij]quinolino[2',1':6,7]morphinan-3,6'α,14β-triol 8 and 6,7-didehydro-4,5α-epoxy-8'-fluoro-5',6'-dihydro-4'H-pyrrolo[3,2,1-ij]quinolino[2',1':6,7]morphinan-3,6'β,14β-triol 9.

4 (9.0 g, 19 mmol) and chlorotris(triphenylphosphine)rhodium (5.0 g) were mixed in acetonitrile (300 mL) and distilled water (100 mL), and the mixture was heated under reflux for 4 hours. The reaction solution was concentrated under the reduced pressure, and the concentrate was purified by column chromatography on silica gel (Silica gel NH-DM 1020, Fuji Silysia, 400 g; chloroform/methanol=25/1). The resultant was purified by recrystallization from methanol/chloroform to obtain the object product 8. Also, 5 was used instead of 4 as a starting material to obtain the object product 9.

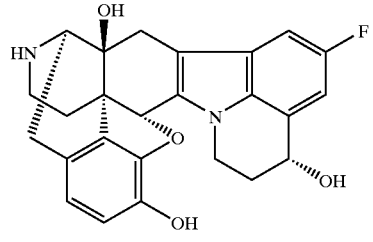

8

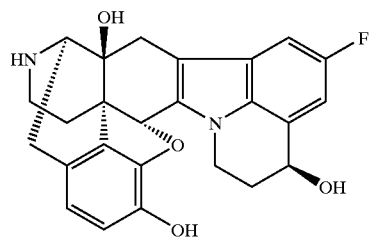

9

EXAMPLES 10 AND 11

6,7-Didehydro-4,5α-epoxy-17-phenethyl-5',6'-dihydro-4'H-pyrrolo[3,2,1-ij]quinolino-[2',1':6,7]morphinan-3,6'α,14β-triol 10-tartrate and 6,7-didehydro-4,5α-epoxy-17-phenethyl-5',6'-dihydro-4'H-pyrrolo[3,2,1-ij]quinolino[2',1':6,7]morphinan-3,6'β,14β-triol 11-tartrate.

In accordance with the method described in Examples 4 and 5, 4a and phenylhydrazine were used as starting materials to obtain 1'-(2-carboxyethyl)-17-allyl-6,7-didehydro-4,5α-epoxy-3-methoxy-indolo[2',3':6,7]morphinan-14β-ol 10a.

10a (2.5 g, 4.9 mmol), 5% palladium/charcoal (water content 50%, 375 mg), and acetic acid (0.6 mL) were mixed in ethanol (60 mL) and distilled water (15 mL), and the mixture was heated under reflux for 24 hours. The reaction solution was filtered using Celite, aqueous sodium bicarbonate and chloroform were added to the filtrate, and liquid separation was performed. After the organic phase was dried over anhydrous sodium sulfate, filtration and concentration were performed. Thus, 1'-(2-carboxyethyl)-6,7-didehydro-4,5α-epoxy-3-methoxy-indolo-[2',3':6,7]morphinan-14β-ol 10b was obtained (quantitatively).

10b (2.3 g, 4.9 mmol), phenylacetaldehyde (50% isopropyl alcohol, 2.3 g), acetic acid (0.33 mL) and sodium triacetoxyborohydride (2.1 g) were mixed in anhydrous THF (50 mL), and the mixture was stirred at room temperature for 1.5 hours. Acetone and aqueous sodium bicarbonate were added to the reaction solution, and extraction with chloroform was performed. The resultant was dried over anhydrous sodium sulfate, and the concentrate was purified by column chromatography on silica gel (Silica gel 7734, Merck, chloroform/methanol=100/1→75/1). Thus, 1'-(2-carboxyethyl)-6,7-didehydro-4,5α-epoxy-17-phenethyl-3-methoxy-indolo[2',3':6,7]-morphinan-14β-ol 10c was obtained.

In accordance with the method described in Examples 4 and 5, 10c was used as a starting material instead of 4c to obtain 6,7-didehydro-4,5α-epoxy-17-phenethyl-3-methoxy-6'-oxo-5',6'-dihydro-4'H-pyrrolo[3,2,1-ij]quinolino[2',1':6,7]morphinan-14β-ol 10d. Further, in accordance with the method described in Examples 4 and 5, 10d was used as a starting material to obtain 10 and 11. These products were converted into salts of tartaric acid, and object products were obtained.

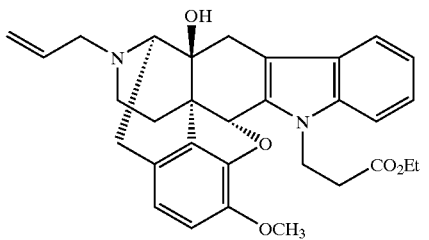

10a

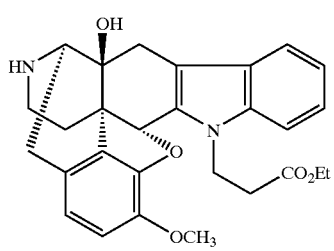

10b

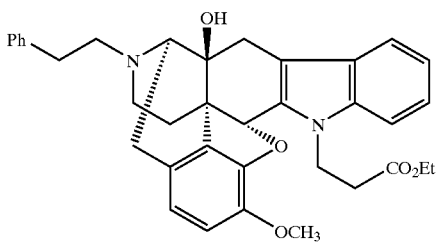

10c

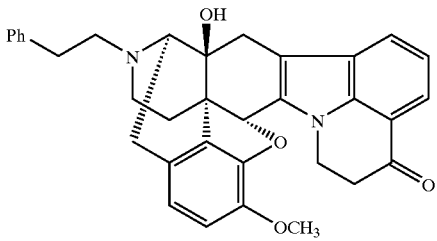

10d

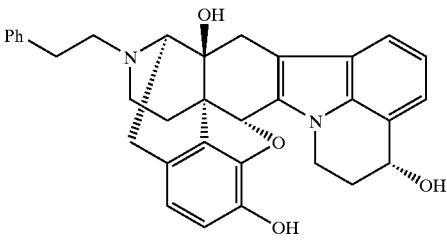

10

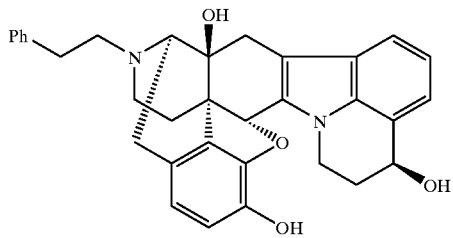

11

EXAMPLE 12

6,7-Didehydro-4,5α-epoxy-17-phenethyl-6'-oxo-5',6'-dihydro-4'H-pyrrolo[3,2,1-ij]-quinolino[2',1':6,7]morphinan-3,14β-diol 12-methanesulfonate.

The intermediate 10d (120 mg, 0.23 mmol) described in Example 10, methyl ortho formate (0.6 mL), and p-toluenesulfonic acid (51 mg) were mixed in methanol (6 mL), and the mixture was stirred at room temperature for 3 hours. Aqueous sodium bicarbonate was added to the reaction solution, and extraction with chloroform was performed. The resultant was dried over anhydrous sodium sulfate and concentrated. Thus, 6,7-didehydro-4,5α-epoxy-17-phenethyl-3,6',6'-trimethoxy-5',6'-dihydro-4'H-pyrrolo[3,2,1-ij]quinolino[2'1':6,7]morphinan-14β-ol 12a was obtained (quantitatively).

12a (99 mg, 0.17 mmol) and n-propanethiol (0.15 mL) were mixed in dimethylformamide (4 mL), potassium t-butoxide (158 mg) was added thereto, and the mixture was stirred at 130° C. for 19 hours. After cooling, 1N hydrochloric acid (2 mL) was added, and the mixture was stirred. Aqueous sodium bicarbonate was added thereto, extraction with toluene was performed, and the organic phase was washed with distilled water. The organic phase was dried over anhydrous magnesium sulfate and concentrated. The resulting crude product was purified by column chromatography on silica gel (Silica gel 7734, Merck, chloroform/methanol=200/1→50/1) to obtain 12. This compound was converted into salt with the methanesulfonic acid to obtain the object product.

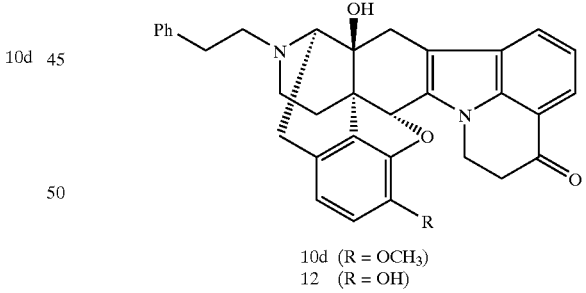

10d (R = OCH₃)
12  (R = OH)

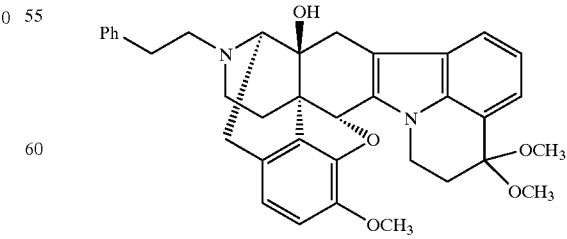

12a

EXAMPLE 13

17-Cyclopropylmethyl-6,7-didehydro-4,5α-epoxy-8'-fluoro-5',6'-dihydro-4'H-pyrrolo-[3,2,1-ij]quinolino[2',1':6,7]morphinan-3,7',14β-triol 13-methanesulfonate.

In accordance with the method of indole synthesis described in Example 1, naltrexone benzoate and 1-amino-6-fluoro-5-methoxy-1,2,3,4-tetrahydroquinoline 13a were used as starting materials to obtain 17-cyclopropylmethyl-6,7-didehydro-4,5α-epoxy-8'-fluoro-7'-methoxy-5',6'-dihydro-4'H-pyrrolo[3,2,1-ij]quinolino[2',1':6,7]morphinan-3,14β-diol 13b.

13b (400 mg, 0.79 mmol) was dissolved in dry dichloromethane (5 mL), a solution of boron tribromide in dichloromethane (1.0 M, 4.9 ml, 4.9 mmol) was added at 0° C., and the mixture was stirred at room temperature for 2.5 hours. After the completion of the reaction, 28% aqueous ammonia (10 mL) was added at 0° C., and the mixture was stirred for 30 minutes. The mixture was transferred into a mixture of chloroform (100 mL) and distilled water (70 mL), and liquid separation was performed. An aqueous phase was extracted with chloroform, and an organic phase was collected, followed by drying and concentration. The resultant was purified by silica gel column to obtain 222 mg of a free base substance of the object product. This product was dissolved in chloroform and methanol, methanesulfonic acid (1 eq) was added, and the solvent was removed by evaporation. The resultant was suspended in ether and collected by filtration, thereby obtaining the object products.

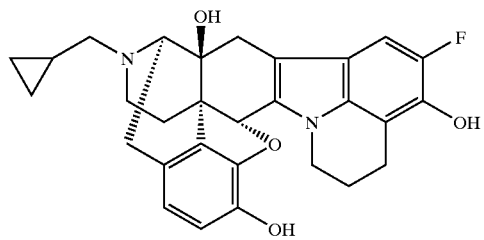

13a

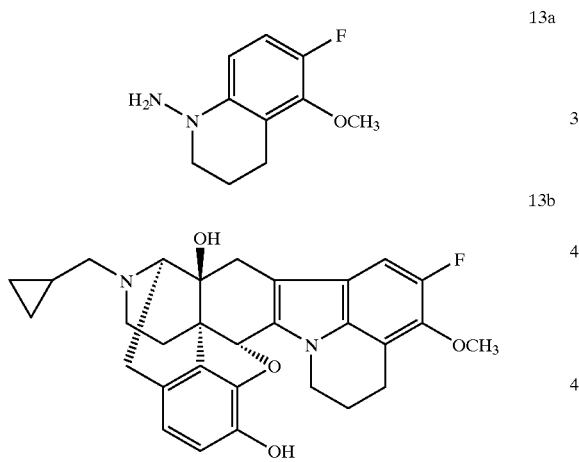

13b

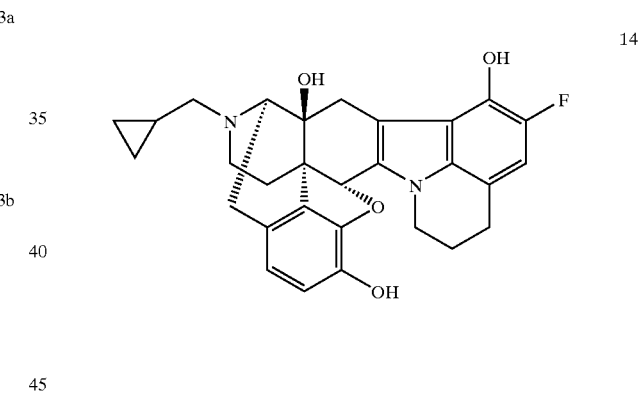

13

EXAMPLE 14

17-Cyclopropylmethyl-6,7-didehydro-4,5α-epoxy-8'-fluoro-5',6'-dihydro-4'H-pyrrolo-[3,2,1-ij]quinolino[2',1':6,7]morphinan-3,9',14β-triol 14-methanesulfonate.

In accordance with the method described in Example 13, the object product was synthesized. As a starting material, 1-amino-6-fluoro-7-methoxy-1,2,3,4-tetrahydroquinoline was used instead of 13a. Thus, the object product was obtained.

14

Physicochemical properties of the compounds according to the present invention listed in Examples above are shown in tables below.

TABLE 26

| | |
|---|---|
| Compound 1 | Yield: 9% |
| | Free base |
| | IR (KBr) cm-1: 3406, 2925, 2833, 1685, 1638, 1493, 1458, 1384, 1211, 1140, 1048, 866. |
| | 1H-NMR (300 MHz, CDCl3)δ: 0.11–0.23(2H, m), 0.50–0.66(2H, m), 0.83–0.96(1H, m), 1.86–1.96(1H, m), 2.24–2.54(4H, m), 2.58–2.68(1H, m), 2.50–3.00(5H, m), 3.14(1H, d, J=19 Hz), 3.38(1H, d, J=6.0 Hz), 4.25–4.45(2H, m), 5.72(1H, s), 6.53(1H, d, J=8.3 Hz), 6.58(1H, d, J=8.0 Hz), 7.23–7.33(2H, m). |
| Compound 2 | Yield: 76% |
| | Benzoate |
| | mp: 170° C. (decomposition) |
| | IR (KBr) cm-1: 3397, 2928, 1596, 1550, 1495, 1383, 723. |
| | 1H-NMR (300 MHz, DMSO-d6)δ: 0.08–0.22(2H, m), 0.43–0.57(2H, m), 0.83–0.95(1H, m), 1.55–1.65(1H, m), 2.08–2.25(3H, m), 2.28–2.55(4H, m), 2.62–2.80(3H, m), 3.08(1H, d, J=19 Hz), 3.29(1H, d, J=6.3 Hz), 4.14–4.26(1H, m), 4.26–4.38(1H, m), 4.92(1H, m), 5.50(1H, br s), 5.74(1H, s), 6.51(2H, m), 6.88(1H, dd, J=2.2, 10 Hz), 7.04(1H, dd, J=2.2, 10 Hz), 7.50(2H, m), 7.62(1H, dd, J=7.1, 7.2 Hz), 7.95(2H, m), 8.95(1H, br s). |
| | MS (Fab): 489[M+H]+. |

TABLE 26-continued

| | |
|---|---|
| | Elementary analysis: C29H29N2O4F1.1.0PhCO2H.0.1AcOEt.0.6H2O<br>Calculated: C 69.36; H 5.92; N 4.44; F 3.01.<br>Found: C 69.44; H 5.94; N 4.50; F 3.15. |
| Compound 3 | Yield: 74%<br>Methanesulfonate<br>mp: 240° C. (decomposition)<br>IR (KBr) cm−1: 3420, 2360, 2340, 1653, 1206, 1048.<br>1H-NMR (300 MHz, DMSO-d6)δ: 0.37–0.55(2H, m), 0.55–0.80(m, 2H), 1.80–1.88(1H, m),<br>2.03–2.20(1H, m), 2.20–2.38(1H, m), 2.31(3H, s), 2.45–2.80(4H, m), 2.82–3.00(1H, m),<br>2.90(1H, d, J=16 Hz), 3.05–3.18(1H, m), 3.18–3.50(4H, m), 4.06(1H, d, J=6.0 Hz),<br>4.19–4.38(2H, m), 4.97–5.02(1H, m), 5.62(1H, br s), 5.90(1H, s), 6.36(1H, br s), 6.60<br>(1H, d, J=8.0 Hz), 6.63(1H, d, J=8.2 Hz), 6.94(1H, dd, J=2.2, 10 Hz), 7.00(1H, dd, J=2.2,<br>10 Hz), 8.95(1H, br s), 9.23(1H, br s).<br>MS (EI): 488[M]⁺ (free base).<br>Elementary analysis: C29H29N2O4F1.1.0MeSO3H.0.16AcOEt.0.50H2O<br>Calculated: C 60.55; H 5.85; N 4.61; S 5.28; F 3.13.<br>Found: C 60.52; H 5.81; N 4.52; S 5.52; F 3.14. |

TABLE 27

| | |
|---|---|
| Compound 4 | Yield: 71%<br>Free base<br>IR (KBr) cm−1: 3387, 2922, 2835, 1626, 1495, 1455, 1367, 1287, 1230, 1136, 1113, 1046, 995,<br>942, 865, 797.<br>1H-NMR (300 MHz, CDCl3)δ: 1.74(1H, d, J=9.0 Hz), 2.24–2.39(4H, m), 2.57–2.66(2H, m),<br>2.71–2.83(1H, m), 3.16–3.24(4H, m), 4.25–4.33(1H, m), 4.37–4.46(1H, m), 4.96–5.00(1H,<br>m), 5.16–5.29(2H, m), 5.71(1H, s), 5.83–5.94(1H, m), 6.51–6.57(2H, m), 6.88(1H, dd,<br>J=8.0, 1.9 Hz), 6.97(1H, dd, J=7.7, 2.2 Hz).<br>MS (EI): 474[M]⁺. |
| Compound 5 | Yield: 81%<br>Free base<br>IR (KBr) cm−1: 3377, 2923, 2840, 1625, 1495, 1456, 1366, 1318, 1288, 1230, 1137, 1113,<br>1059, 994, 967, 908, 863, 797, 750.<br>1H-NMR (300 MHz, CD3OD)δ: 1.73(1H, d, J=11.2 Hz), 2.22–2.40(4H, m), 2.56–2.64(2H,<br>m), 2.69–2.82(2H, m), 3.15–3.23(4H, m), 4.22–4.30(1H, m), 4.40–4.46(1H, m), 4.97–5.01<br>(1H, m), 5.16–5.28(2H, m), 5.70(1H, s), 5.82–5.95(1H, m), 6.53(1H, d, J=8.5 Hz), 6.56<br>(1H, d, J=8.2 Hz), 6.89(1H, dd, J=8.0, 1.6 Hz), 6.95(1H, dd, J=8.0, 2.2 Hz).<br>MS (EI): 474[M]⁺. |
| Compound 6 | Yield: 70%<br>Benzoate<br>mp: 178–182° C.<br>IR (KBr) cm−1: 3388, 1625, 1596, 1550, 1495, 1454, 1384, 1140, 1123, 1110, 939.<br>1H-NMR (300 MHz, DMSO-d6)δ: 1.60(1H, m), 2.03–2.28(3H, m), 2.30–2.54(3H, m), 2.38<br>(3H, s), 2.67(1H, d, J=15 Hz), 2.62–2.77(1H, m), 2.98(1H, d, J=6.0 Hz), 3.16(1H, d,<br>J=19 Hz), 3.35(1H, br s), 4.12–4.27(1H, m), 4.27–4.38(1H, m), 4.90(1H, m), 5.51(1H, br s),<br>5.73(1H, s), 6.52(2H, m), 6.88(1H, dd, J=2.2, 9.6 Hz) 7.01(1H, dd, J=2.0, 10 Hz),<br>7.46–7.54(2H, m), 7.58–7.65(1H, m), 7.92–7.98(2H, m), 8.99(1H, br s).<br>MS (EI): 448[M]⁺ (free base).<br>Elementary analysis: C26H25N2O4F1.1.0PhCO2H.0.8H2O<br>Calculated: C 67.64; H 5.71; N 4.91; F 3.22.<br>Found: C 67.75; H 5.62; N 4.79; F 3.25. |

TABLE 28

| | |
|---|---|
| Compound 7 | Yield: 70%<br>Benzoate<br>mp: 186° C. (decomposition).<br>IR (KBr) cm−1: 3378, 1596, 1550, 1383, 1285, 1110, 862, 723.<br>1H-NMR (300 MHz, DMSO-d6)δ: 1.59(1H, m), 2.02–2.37(6H, m), 2.38(3H, s), 2.66(1H,<br>d, J=15 Hz), 2.62–2.78(1H, m), 2.97(1H, d, J=6.0 Hz), 3.16(1H, d, J=18 Hz), 3.35(1H, br<br>s), 4.15–4.27(1H, m), 4.27–4.40(1H, m), 4.93(1H, m), 5.57(1H, br s), 5.73(1H, s), 6.51<br>(2H, m), 6.89(1H, dd, J=2.0, 10 Hz), 7.01(1H, dd, J=2.5, 10 Hz), 7.45–7.54(2H, m),<br>7.57–7.65(1H, m), 7.92–7.98(2H, m).<br>MS (EI): 448[M]⁺.<br>Elementary analysis: C26H25N2O4F1.0.98PhCO2H.0.21Et2O.0.11.0.40H2O<br>Calculated.: C 68.21; H 5.53; N 5.04; F 3.13.<br>Found: C 68.50; H 5.76; N 4.74; F 3.21. |
| Compound 8 | Yield: 28%<br>Free base<br>mp: 300° C. (decomposition)<br>IR (KBr) cm−1: 3364, 2912, 1631, 1496, 1447, 1272, 1145, 1073, 1049, 982, 948, 866, 797.<br>1H-NMR (300 MHz, DMSO-d6)δ: 1.43(1H, d, J=10 Hz), 2.08–2.27(3h, m), 2.36(1H, d,<br>J=15 Hz), 2.50–2.68(3H, m), 2.91(1H, d, J=18 Hz), 3.05(1H, d, J=6.6 Hz), 3.10(1H, d,<br>J=6.6 Hz), 3.16(1H, d, J=6.3 Hz), 4.15–4.32(2H, m), 4.89(1H, br s), 5.50(1H, d, |

TABLE 28-continued

|  |  |
|---|---|
|  | J=4.9 Hz), 5.61(1H, s), 6.45(1H, d, J=8.2 Hz), 6.49(1H, d, J=8.2 Hz), 6.85(1H, dd, J=7.7, 2.2 Hz), 6.96(1H, dd, J=8.0, 2.2 Hz), 8.91(1H, br s).<br>MS (EI): 434[M]$^+$.<br>Elementary analysis: C25H23N2O4F.1.4H2O<br>Calculated: C 65.32; H 5.66; N 6.09; F 4.13.<br>Found: C 65.59; H 5.29; N 5.89; F 4.17. |
| Compound 9 | Yield: 40%<br>Free base<br>mp: 300° C. (decomposition)<br>IR (KBr) cm−1: 3377, 2922, 1627, 1495, 1450, 1369, 1288, 1227, 1142, 1107, 1052, 949, 871,<br>798.<br>1H-NMR (300 MHz, DMSO-d6)δ: 1.42(1H, d, J=5.2 Hz), 2.05–2.14(1H, m), 2.16–2.28 (2H, m), 2.35(1H, d, J=16 Hz), 2.20–2.68(3H, m), 2.90(1H, d, J=17.9 Hz), 3.03–3.15(3H, m), 4.06(1H, br s), 4.05–4.32(2H, m), 4.85–4.97(1H, m), 5.53(1H, d, J=5.2 Hz), 5.61 (1H, s), 6.45(1H, d, J=8.0 Hz), 6.49(1H, d, J=8.0 Hz), 6.82–6.87(1H, m), 6.93–6.98(1H, m), 8.89(1H, br s).<br>MS (EI): 434[M]$^+$.<br>Elementary analysis: C25H23N2O4F.0.9H2O.0.3MeOH<br>Calculated: C 66.02; H5.69; N 6.09; F 4.13.<br>Found: C 66.26; H 5.64; N 5.80; F 3.99. |

TABLE 29

|  |  |
|---|---|
| Compound 10 | Yield: 38%<br>Tartrate<br>mp: 160° C. (decomposition).<br>IR (KBr) cm−1: 3320, 2926, 1720, 1618, 1406, 1306, 1265, 1214, 1068, 937, 681.<br>1H-NMR (300 MHz, DMSO-d6)δ: 1.62(1H, m), 2.13(2H, m), 2.24–2.50(3H, m), 2.72(1H, d, J=16 Hz), 2.72–3.00(6H, m), 3.10–3.30(2H, m), 4.07–4.25(1H, m), 4.18(2H, s), 4.25–4.38(1H, m), 4.90(1H, m), 5.38(1H, br s), 5.78(1H, s), 6.52(2H, m), 6.92(1H, m), 7.04(1H, m), 7.10–7.37(6H, m), 9.00(1H, br s).<br>MS (ESI):<br>Calculated: 521.2440<br>Found: 521.2442[M+H]$^+$. |
| Compound 11 | Yield: 67%<br>Tartrate<br>mp: 153° C. (decomposition).<br>IR (KBr) cm−1: 3320, 2926, 1720, 1619, 1506, 1406, 1305, 1264, 1214, 1067, 680.<br>1H-NMR (300 MHz, DMSO-d6)δ: 1.62(1H, m), 2.15(2H, m), 2.25–2.47(3H, m), 2.72(1H, d, J=15 Hz), 2.72–3.00(6H, m), 3.10–3.32(2H, m), 4.10–4.37(2H, m), 4.18(2H, s), 4.93 (1H, m), 5.40(1H, br s), 5.76(1H, s), 6.53(2H, m), 6.91(1H, m), 7.05(1H, m), 7.10–7.38 (6H, m), 9.00(1H, br s).<br>MS (ESI):<br>Calculated: 521.2440<br>Found: 521.2421[M+H]$^+$. |
| Compound 12 | Yield: 26%<br>Methanesulfonate<br>mp: 230° C. (decomposition).<br>IR (KBr) cm−1: 3423, 2927, 1676, 1589, 1487, 1457, 1355, 1290, 1196, 1116, 1045, 937.<br>1H-NMR (300 MHz, DMSO-d6)δ: 1.90(1H, m), 2.56–3.40(10H, m), 3.01(1H, d, J=16 Hz), 3.57(1H, m), 4.00(1H, m), 4.42–4.57(1H, m), 4.57–4.70(1H, m), 5.98(1H, s), 6.39(1H, br s), 6.65(2H, m), 7.16(1H, m), 7.25–7.43(6H, m), 7.55(1H, d, J=7.4 Hz), 7.71(1H, d, J=8.0 Hz), 9.19(1H, br s), 9.23(1H, br s).<br>MS (ESI):<br>Calculated: 519.2284<br>Found: 519.2258[M+H]$^+$. |

TABLE 30

|  |  |
|---|---|
| Compound 13 | Yield: 77%<br>Methanesulfonate<br>mp: 180° C. (decomposition)<br>IR (KBr) cm−1: 3434, 1637, 1480, 1459, 1191, 1045.<br>1H-NMR (300 MHz, DMSO-d6)δ: 0.35–0.55(2H, m), 0.55–0.78(2H, m), 1.75–1.85(1H, m), 1.98–2.25(1H, 2H), 2.45–3.00(7H, m), 2.85(1H, d, J=13 Hz), 3.05–3.30(2H, m), 3.32–3.50 (2H, m), 4.03(1H, d, J=6.0 Hz), 4.00–4.15(1H, m), 4.15–4.27(1H, m), 5.83(1H, s), 6.32 (1H, br s), 6.58(1H, d, J=8.2 Hz), 6.63(1H, d, J=8.0 Hz), 6.93(1H, d, J=11 Hz), 8.83–9.06 (2H, m), 9.20(1H, br s).<br>MS (EI): 489[M]$^+$ (free base).<br>Elementary analysis: C29H29N2O4F1.1.15MeSO3H.0.1Et2O.0.4H2O<br>Calculated: C 59.97; H 6.09; N 4.40; S 5.79, F 2.98.<br>Found: C 59.94; H 5.91; N 4.42; S 5.86, F 3.18. |

TABLE 30-continued

Compound 14    Yield: 30%
Methanesulfonate
mp: 280° C. (decomposition)
IR (KBr) cm-1: 3398, 2928, 1638, 1560, 1521, 1508, 1458, 1437, 1380, 1328, 1291, 1194, 1116, 1024, 943, 914, 868, 839, 784.
1H-NMR (300 MHz, DMSO-d6)δ: 0.41–0.45(1H, m), 0.47–0.51(1H, m), 0.60–0.65(1H, m), 0.71–0.76(1H, m), 1.04–1.10(1H, m), 1.82(1H, d, J=11 Hz), 2.06–2.10(1H, m), 2.12–2.17 (1H, m), 2.31(3.9H, s), 2.58(1H, td, J=13.2, 4.6 Hz), 2.63(1H, d, J=18.3 Hz), 2.69–2.75(1H, m), 2.81–2.83(1H, m), 2.89–2.96(1H, m), 3.09(1H, d, J=11 Hz), 3.25(1H, d, J=16 Hz), 3.29 (1H, d, J=7.1 Hz), 3.36–3.46(3H, m), 4.07(1H, d, J=7.1 Hz), 4.08–4.12(1H, m), 4.21–4.25 (1H, m), 5.83(1H, s), 6.30(1H, br s), 6.60(1H, d, J=8.3 Hz), 6.63(1H, d, J=8.1 Hz), 6.70 (1H, d, J=12 Hz), 8.89(1.3H, brs), 9.22(2H, br s).
MS (FAB): 489[M+H]⁺.
Elementary analysis: C29H29N2O4F3.1.3MeSO3H.0.2H2O
Calculated: C 58.97; H 5.65; N 4.52; S 6.76; F 3.08.
Found: C 59.17; H 5.89; N 4.62; S 6.61; F 2.87.

EXAMPLE 15

Opioid Activities

Using mouse vas deferens (MVD), the compounds were examined for antagonism against opioid receptor agonists, i.e., morphine ($\mu$), DPDPE ($\delta$), and U50,488H ($\kappa$).

Male ddy strain mice were used in this experiment. Each of the vas deferens isolated from the mice was hung in a Magnus tube which was maintained at 37° C., filled with a Krebes-Henseleit solution (NaCl 118 mM; KCl 4.7 mM; $CaCl_2$ 2.5 mM; $KH_2PO_4$ 1.1 mM; $NaHCO_3$ 25 mM; glucose 11 mM), and aerated with 5% carbon dioxide and 95% oxygen. Electric stimulation was applied through upper and lower ring-shaped platinum electrodes at 0.1 Hz and 5.0 mS. Tissue contraction was recorded on a polygraph using an Isometric Transducer.

Morphine, DPDPE, and U50,488H were added in a cumulative manner to determine the $IC_{50}$ values (concentration for 50% inhibition of contraction induced by electric stimulation). Next, 10 nM of a sample compound was added to the system beforehand, and 20 minutes later, morphine, DPDPE, and U50,488H were added in a cumulative manner. According to the above procedure, the ratio of the $IC_{50}$ values of morphine, DPDPE, and U50,488H in the presence of the sample compound to that in its absence was determined, and the $pA_2$ values were calculated in accordance with the Schild et al.'s method (Schild, H. O., Br. J. Pharmacol. Chemother. 4, 277 (1949)). The results are shown in the table below.

TABLE 31

Test results on antagonism against opioid receptor

| Compound | pA2 | | |
|---|---|---|---|
| | $\mu$ | $\delta$ | $\kappa$ |
| 3 | N.D. | 8.4 | N.D. |

N.D.: the pA2 value is indeterminable because the compound does not antagonize.

All publications, patents, and patent applications cited herein are incorporated herein by reference in their entirety.

Industrial Applicability

The compound of the present invention acts selectively on the δ opioid receptor with high affinity. Thus, it can be used as an agent such as an analgesic, antitussive, immunosuppressive agent, or brain-cell-protecting agent which does not exhibit any side effect such as drug dependence, suppression of the CNS, constipation, respiratory depression, drug aversion, or psychotomimetic effects.

What is claimed is:

1. An indole derivative represented by general formula (I) or a pharmaceutically acceptable salt thereof:

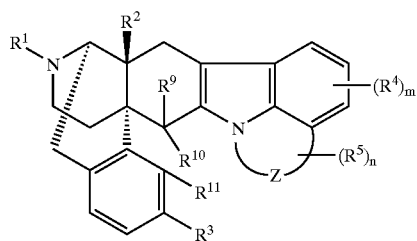

(I)

wherein $R^1$ is hydrogen, $C_{1-5}$ alkyl, $C_{4-7}$ cycloalkylalkyl, $C_{5-7}$ cycloalkenylalkyl, $C_{6-12}$ aryl, $C_{7-13}$ aralkyl, $C_{3-7}$ alkenyl, furan-2-yl-alkyl (wherein the alkyl moiety is $C_{1-5}$), or thiophen-2-yl-alkyl (wherein the alkyl moiety is $C_{1-5}$);

$R^2$ is hydrogen, hydroxy, $C_{1-5}$ alkoxy, or $C_{1-5}$ aliphatic acyloxy;

$R^3$ is hydrogen, hydroxy, $C_{2-5}$ alkoxy, $C_{1-5}$ aliphatic acyloxy, or $C_{7-13}$ aralkyloxy;

—Z— is a crosslinkage having 2 to 5 carbon atoms;

m is an integer from 0 to 3;

n is an integer from 0 to 10;

m number of $R^4$ groups and n number of $R^5$ groups are independently fluoro, chloro, bromo, iodo, nitro, $C_{1-5}$ alkyl, hydroxy, $C_{1-5}$ alkoxy, trifluoromethyl, trifluoromethoxy, cyano, phenyl, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH_2)_pN(R^7)COR^8$ (wherein p is an integer from 0 to 5; $R^6$ is hydrogen or $C_{1-5}$ alkyl; and $R^7$ and $R^8$ are independently hydrogen, $C_{1-5}$ alkyl, or $C_{4-7}$ cycloalkylalkyl), among n number of $R^5$ groups, two $R^5$ groups bound to the same carbon atom become an oxygen atom to form oxo, or among m number of $R^4$ groups and n number of $R^5$ groups, two adjacent $R^4$ groups, two adjacent $R^5$ groups, or $R^4$ and $R^5$ may be bound to each other to form a benzene, pyridine, cyclopentane, cyclohexane, or cycloheptane fused ring, with the proviso that both m and n cannot be 0 simultaneously and furthermore, at least one of $R^4$ and $R^5$ groups represents hydroxy, or two $R^5$ groups bound to the same carbon atom form oxo;

$R^9$ is hydrogen, $C_{1-5}$ alkyl, $C_{2-5}$ alkenyl, $C_{7-13}$ aralkyl, $C_{1-3}$ hydroxyalkyl, $(CH_2)_pOR^6$, or $(CH_2)_pCO_2R^6$, wherein p and $R^6$ are as defined above; and $R^{10}$ and $R^{11}$ are bound to each other to form —O—, —S—, or —CH$_2$—, or $R^{10}$ is hydrogen while $R^{11}$ is hydrogen, hydroxy, C$_{1-5}$ alkoxy, or C$_{1-5}$ aliphatic acyloxy.

2. The indole derivative according to claim 1, which is represented by general formula (I) wherein $R^3$ is hydrogen, hydroxy, or acetoxy, or a pharmaceutically acceptable salt thereof.

3. The indole derivative according to claim 1, which is represented by general formula (I) wherein $R^3$ is hydroxy, or a pharmaceutically acceptable salt thereof.

4. The indole derivative according to claim 1, which is represented by general formula (I) wherein $R^1$ is C$_{4-7}$ cycloalkylalkyl or C$_{3-7}$ alkenyl, or a pharmaceutically acceptable salt thereof.

5. The indole derivative according to claim 4, which is represented by general formula (I) wherein $R^1$ is cyclopropylmethyl, or a pharmaceutically acceptable salt thereof.

6. The indole derivative according to claim 1, which is represented by general formula (I) wherein $R^1$ is hydrogen, C$_{1-5}$ alkyl, C$_{7-13}$ aralkyl, furan-2-yl-alkyl (wherein the alkyl moiety is C$_{1-5}$), or thiophen-2-yl-alkyl (wherein the alkyl moiety is C$_{1-5}$), or a pharmaceutically acceptable salt thereof.

7. The indole derivative according to claim 6, which is represented by general formula (I) wherein $R^1$ is hydrogen, methyl, phenethyl, furan-2-ylethyl, or thiophen-2-ylethyl, or a pharmaceutically acceptable salt thereof.

8. The indole derivative according to claim 1, which is represented by general formula (I) wherein two $R^5$ groups bound to the same carbon atom become an oxygen atom to form oxo, or a pharmaceutically acceptable salt thereof.

9. The indole derivative according to claim 1, which is represented by general formula (I) wherein at least one of m number of $R^4$ groups is hydroxy, or a pharmaceutically acceptable salt thereof.

10. The indole derivative according to claim 1, which is represented by general formula (I) wherein at least one of n number of $R^5$ groups is hydroxy or a pharmaceutically acceptable salt thereof.

11. A pharmaceutical composition comprising the indole derivative or a pharmaceutically acceptable salt thereof according to claim 1.

12. A method of inhibiting δ opioid receptor in a mammal comprising administering to said mammal a therapeutically effective amount of the indole derivative or a pharmaceutically acceptable salt thereof according to claim 1.

13. A δ opioid receptor agonist comprising the indole derivative or a pharmaceutically acceptable salt thereof according to claim 1.

14. A δ opioid receptor antagonist comprising the indole derivative or a pharmaceutically acceptable salt thereof according to claim 1.

* * * * *